US012797578B2

(12) United States Patent
Franklin et al.

(10) Patent No.: US 12,797,578 B2
(45) Date of Patent: Nov. 17, 2026

(54) OCCLUSION CATHETER SYSTEM FOR PARTIAL OCCLUSION OR FULL OCCLUSION

(71) Applicant: Prytime Medical Devices, Inc., Boerne, TX (US)

(72) Inventors: Curtis J. Franklin, Boerne, TX (US); David Spencer, Boerne, TX (US); Todd J. Krummenacher, Boerne, TX (US)

(73) Assignee: PRYTIME MEDICAL DEVICES, INC., Boerne, TX (US)

(*) Notice: Subject to any disclaimer, the term of this patent is extended or adjusted under 35 U.S.C. 154(b) by 0 days.

(21) Appl. No.: 19/356,360

(22) Filed: Oct. 13, 2025

(65) Prior Publication Data

US 2026/0091199 A1 Apr. 2, 2026

Related U.S. Application Data

(63) Continuation of application No. 17/563,629, filed on Dec. 28, 2021, which is a continuation of application
(Continued)

(51) Int. Cl.
*A61M 25/00* (2006.01)
*A61B 17/12* (2006.01)
(Continued)

(52) U.S. Cl.
CPC ... *A61M 25/0068* (2013.01); *A61B 17/12036* (2013.01); *A61M 25/0074* (2013.01);
(Continued)

(58) Field of Classification Search
CPC .......... A61M 25/0068; A61M 25/0074; A61M 25/008; A61M 25/1002; A61M 25/1006;
(Continued)

(56) References Cited

U.S. PATENT DOCUMENTS

| | | | |
|---|---|---|---|
| 2,156,289 | A | 5/1939 | Hoy |
| 3,467,101 | A | 9/1969 | Raible et al. |

(Continued)

FOREIGN PATENT DOCUMENTS

| | | |
|---|---|---|
| CN | 306763167 | 8/2021 |
| EP | 0368523 A2 | 5/1990 |

(Continued)

OTHER PUBLICATIONS

Final Written Decision PGR 2024-00028, mailed Oct. 1, 2025.

(Continued)

*Primary Examiner* — James D Ponton
*Assistant Examiner* — John A Doubrava
(74) *Attorney, Agent, or Firm* — Panitch Schwarze Belisario & Nadel LLP

(57) ABSTRACT

An occlusion catheter system is provided for at least partial occlusion of a vessel. The occlusion catheter system includes a proximal hub having an inflation connection port and an inflation pathway. An inflation catheter member is fluidly connected to the proximal hub. An occlusion balloon has a proximal balloon end and a distal balloon end, the proximal balloon end being fluidly connected to the inflation catheter member. A distal catheter member is connected to the distal balloon end and includes an atraumatic tip on a distal end thereof, the atraumatic tip having a substantially circular profile in one configuration. The occlusion balloon, the inflation catheter member and the distal catheter member have a greatest outer diameter of less than 7 Fr in an uninflated condition.

25 Claims, 33 Drawing Sheets

Related U.S. Application Data

No. 16/133,193, filed on Sep. 17, 2018, now Pat. No. 11,672,951, which is a continuation of application No. 15/551,504, filed as application No. PCT/US2016/023223 on Mar. 18, 2016, now Pat. No. 10,149,962.

(60) Provisional application No. 62/204,804, filed on Aug. 13, 2015, provisional application No. 62/136,571, filed on Mar. 22, 2015, provisional application No. 62/136,180, filed on Mar. 20, 2015, provisional application No. 62/136,370, filed on Mar. 20, 2015, provisional application No. 62/136,152, filed on Mar. 20, 2015, provisional application No. 62/136,123, filed on Mar. 20, 2015, provisional application No. 62/136,326, filed on Mar. 20, 2015, provisional application No. 62/136,390, filed on Mar. 20, 2015, provisional application No. 62/136,230, filed on Mar. 20, 2015, provisional application No. 62/135,576, filed on Mar. 19, 2015, provisional application No. 62/135,552, filed on Mar. 19, 2015, provisional application No. 62/135,609, filed on Mar. 19, 2015, provisional application No. 62/135,528, filed on Mar. 19, 2015, provisional application No. 62/135,603, filed on Mar. 19, 2015.

(51) Int. Cl.
*A61M 25/10* (2013.01)
*A61B 17/00* (2006.01)

(52) U.S. Cl.
CPC ...... *A61M 25/008* (2013.01); *A61M 25/1002* (2013.01); *A61M 25/1006* (2013.01); *A61M 25/10182* (2013.11); *A61M 25/104* (2013.01); *A61B 2017/00017* (2013.01); *A61B 17/12045* (2013.01); *A61B 17/12109* (2013.01); *A61M 2025/0002* (2013.01); *A61M 25/007* (2013.01); *A61M 2025/1052* (2013.01); *A61M 2025/1059* (2013.01); *A61M 2025/1081* (2013.01); *A61M 2025/1084* (2013.01); *A61M 2025/1086* (2013.01); *A61M 2025/1093* (2013.01)

(58) Field of Classification Search
CPC .......... A61M 25/10182; A61M 25/104; A61M 25/007; A61M 2025/0002; A61M 2025/1052; A61M 2025/1059; A61M 2025/1081; A61M 2025/1084; A61M 2025/1086; A61M 2025/1093; A61B 17/12036; A61B 17/12045; A61B 17/12109; A61B 2017/00017
See application file for complete search history.

(56) References Cited

U.S. PATENT DOCUMENTS 3,585,983 A 6/1971 Kantrowitz et al.
3,791,374 A 2/1974 Guarino
4,276,874 A * 7/1981 Wolvek ............ A61M 25/0054 604/914
4,439,185 A 3/1984 Lundquist
4,464,172 A 8/1984 Lichtenstein
4,573,470 A 3/1986 Samson et al.
4,582,181 A 4/1986 Samson
4,616,653 A 10/1986 Samson et al.
4,646,719 A 3/1987 Neuman et al.
4,713,888 A 12/1987 Broselow
4,777,951 A 10/1988 Cribier et al.
4,823,469 A 4/1989 Broselow
4,838,268 A 6/1989 Keith et al.
4,838,269 A 6/1989 Robinson et al.
4,846,174 A 7/1989 Willard et al.
4,865,549 A 9/1989 Sonsteby
4,906,241 A 3/1990 Noddin et al.
4,926,885 A 5/1990 Hinkle
4,983,166 A 1/1991 Yamawaki
5,032,113 A 7/1991 Burns
5,042,985 A 8/1991 Elliott et al.
5,047,045 A 9/1991 Arney et al.
5,087,246 A * 2/1992 Smith .............. A61M 25/1002 604/103
5,116,305 A * 5/1992 Milder ............... A61M 60/531 604/914
5,135,494 A 8/1992 Engelson et al.
5,158,529 A * 10/1992 Kanai ................ A61M 60/554 604/914
5,169,386 A 12/1992 Becker et al.
5,250,070 A 10/1993 Parodi
5,282,479 A 2/1994 Havran
5,295,995 A 3/1994 Kleiman
5,320,605 A 6/1994 Sahota
5,364,352 A 11/1994 Cimino et al.
5,380,284 A 1/1995 Don Michael
5,383,856 A 1/1995 Bersin
5,387,225 A 2/1995 Euteneuer et al.
5,423,764 A 6/1995 Fry
5,425,711 A 6/1995 Ressemann et al.
5,447,503 A 9/1995 Miller
5,464,394 A * 11/1995 Miller ................ A61M 25/005 604/524
5,496,275 A 3/1996 Sirhan et al.
5,505,702 A 4/1996 Arney
5,522,400 A 6/1996 Williams
5,554,121 A 9/1996 Ainsworth et al.
5,558,644 A 9/1996 Boyd et al.
5,569,184 A 10/1996 Crocker et al.
5,571,093 A 11/1996 Cruz et al.
5,607,394 A 3/1997 Andersen et al.
5,609,606 A 3/1997 O'Boyle
5,716,373 A * 2/1998 Wolvek .............. A61M 60/139 606/191
5,718,678 A 2/1998 Fleming, III
5,738,652 A 4/1998 Boyd et al.
5,779,731 A 7/1998 Leavitt
5,911,702 A 6/1999 Romley et al.
6,007,517 A 12/1999 Anderson
6,011,988 A 1/2000 Lynch et al.
6,013,019 A 1/2000 Fischell et al.
6,013,055 A 1/2000 Bampos et al.
6,102,930 A 8/2000 Simmons, Jr.
6,113,579 A 9/2000 Eidenschink et al.
6,129,737 A 10/2000 Hamilton et al.
6,146,370 A 11/2000 Barbut
6,161,547 A 12/2000 Barbut
6,165,199 A 12/2000 Barbut
6,190,356 B1 2/2001 Bersin
6,231,572 B1 5/2001 Hart et al.
6,248,121 B1 6/2001 Nobles
6,280,434 B1 8/2001 Kinoshita et al.
6,368,301 B1 4/2002 Hamilton et al.
6,423,031 B1 7/2002 Donlon
6,453,572 B2 9/2002 Cross et al.
6,575,932 B1 6/2003 O'Brien et al.
6,579,221 B1 6/2003 Peterson
6,602,270 B2 8/2003 Leschinsky et al.
6,656,153 B1 12/2003 Sakai et al.
6,666,814 B2 12/2003 Downey et al.
6,669,679 B1 12/2003 Savage et al.
6,679,860 B2 1/2004 Stiger
6,695,811 B2 2/2004 Samson et al.
6,719,270 B2 4/2004 Ozawa
6,719,720 B1 4/2004 Voelker et al.
6,733,513 B2 5/2004 Boyle et al.
6,735,532 B2 5/2004 Freed et al.
6,736,790 B2 5/2004 Barbut et al.
6,746,462 B1 6/2004 Selmon et al.
6,796,959 B2 9/2004 Davis et al.
6,936,056 B2 8/2005 Nash et al.
6,979,318 B1 12/2005 McDonald et al.

(56) References Cited

U.S. PATENT DOCUMENTS 7,341,571 B1 3/2008 Harris et al.
7,434,326 B2 10/2008 Gifford
7,468,027 B2 12/2008 Barbut et al.
7,503,904 B2 3/2009 Choi
7,503,909 B2 3/2009 Kusu et al.
7,763,043 B2 7/2010 Goodin et al.
7,892,469 B2 2/2011 Lim et al.
7,909,810 B2 3/2011 Noone
7,951,186 B2 5/2011 Eidenschink et al.
7,951,819 B2 5/2011 Niculescu-Duvaz et al.
7,959,644 B2 6/2011 Shriver
7,993,366 B2 8/2011 Yassinzadeh et al.
8,021,330 B2 9/2011 McAndrew
8,066,667 B2 11/2011 Hayman et al.
8,088,103 B2 1/2012 Teeslink et al.
8,088,121 B2 1/2012 Nishide et al.
8,162,879 B2 4/2012 Hattangadi et al.
8,241,241 B2 8/2012 Evans et al.
8,262,611 B2 9/2012 Teeslink et al.
8,267,871 B2 9/2012 Eberhardt et al.
8,419,648 B2 4/2013 Corl et al.
8,430,899 B2 4/2013 Dae et al.
8,486,046 B2 7/2013 Hayman et al.
8,491,648 B2 7/2013 Hassan et al.
8,499,681 B2 8/2013 Kanner et al.
8,545,382 B2 10/2013 Suzuki et al.
8,655,798 B2 2/2014 Humphrey et al.
8,672,868 B2 3/2014 Simons
8,747,358 B2 6/2014 Trombley, III et al.
8,814,900 B2 8/2014 Fleming, III
8,888,740 B2 11/2014 Barbut et al.
8,900,214 B2 12/2014 Nance et al.
8,948,848 B2 2/2015 Merhi
8,951,565 B2 2/2015 McCarthy
9,131,874 B2 9/2015 Eliason et al.
9,211,396 B2 12/2015 Aboytes
D748,257 S 1/2016 Franklin
9,414,843 B2 8/2016 Pavcnik et al.
9,474,882 B2 10/2016 Franklin
9,498,225 B2 11/2016 Zhadkevich
9,687,333 B2 6/2017 Angel et al.
9,731,099 B2 8/2017 Krolik et al.
10,004,622 B2 6/2018 Sanati et al.
10,111,669 B2 10/2018 Eliason et al.
10,143,789 B2 12/2018 Frost
10,279,094 B2 5/2019 Williams et al.
10,368,872 B2 8/2019 Franklin et al.
10,449,337 B2 10/2019 Kassab et al.
D967,408 S 10/2022 Tanaka et al.
2001/0038807 A1 11/2001 Barbut et al.
2002/0007146 A1 1/2002 Omaleki et al.
2002/0062119 A1 5/2002 Zadno-Azizi
2002/0072647 A1 6/2002 Schock et al.
2002/0081406 A1 6/2002 Wang et al.
2002/0169413 A1 11/2002 Keren et al.
2002/0193735 A1 12/2002 Stiger
2003/0032974 A1* 2/2003 Leschinsky ........... A61M 25/10 606/192
2003/0083579 A1 5/2003 Aita et al.
2003/0083617 A1 5/2003 St. Germain et al.
2003/0167038 A1 9/2003 Yozu et al.
2003/0208255 A1 11/2003 O'Shaughnessy et al.
2004/0039332 A1* 2/2004 Kantor .............. A61M 25/0023 604/528
2004/0073162 A1 4/2004 Bleam et al.
2004/0082935 A1 4/2004 Lee et al.
2004/0220521 A1 11/2004 Barbut
2004/0254528 A1 12/2004 Adams et al.
2005/0015048 A1 1/2005 Chiu et al.
2005/0015108 A1 1/2005 Williams et al.
2005/0059931 A1 3/2005 Garrison et al.
2005/0148812 A1 7/2005 Nigroni et al.
2005/0148997 A1 7/2005 Valley et al.
2005/0261725 A1 11/2005 Crawford et al.
2006/0030814 A1* 2/2006 Valencia ............... A61M 25/00 604/93.01
2006/0064059 A1 3/2006 Gelfand et al.
2006/0100639 A1 5/2006 Levin et al.
2007/0043307 A1 2/2007 Raulerson et al.
2007/0043409 A1 2/2007 Brian et al.
2007/0129466 A1 6/2007 Kagawa et al.
2007/0135830 A1 6/2007 Schaeffer
2007/0167972 A1 7/2007 Euteneuer et al.
2007/0219466 A1 9/2007 Tremulis et al.
2007/0219488 A1 9/2007 Francescatti
2008/0027356 A1 1/2008 Chen et al.
2008/0082046 A1 4/2008 Kato et al.
2008/0082119 A1 4/2008 Vitullo
2008/0097300 A1 4/2008 Eskaros et al.
2008/0171977 A1 7/2008 Blix
2008/0178882 A1 7/2008 Christopher et al.
2008/0188803 A1 8/2008 Jang
2008/0200839 A1 8/2008 Bunch et al.
2008/0243067 A1 10/2008 Rottenberg et al.
2008/0243221 A1 10/2008 Arcand
2008/0262477 A1 10/2008 Djaladat
2008/0287786 A1 11/2008 Lentz
2009/0018500 A1 1/2009 Carter et al.
2009/0026595 A1 1/2009 Kadoi
2009/0062666 A1 3/2009 Roteliuk
2009/0171272 A1 7/2009 Tegg et al.
2009/0171293 A1 7/2009 Yang et al.
2009/0265951 A1 10/2009 Black
2009/0275919 A1 11/2009 Todd et al.
2009/0287079 A1 11/2009 Shriver
2009/0312807 A1 12/2009 Boudreault et al.
2010/0016735 A1 1/2010 Harpas et al.
2010/0041984 A1 2/2010 Shapland et al.
2010/0113939 A1 5/2010 Mashimo et al.
2010/0130810 A1 5/2010 Mohl
2010/0204712 A1* 8/2010 Mallaby ................ A61B 17/22 606/128
2010/0234915 A1 9/2010 Herlich et al.
2010/0241008 A1 9/2010 Belleville et al.
2010/0262076 A1 10/2010 Rowe et al.
2010/0268017 A1 10/2010 Siess
2010/0280451 A1 11/2010 Teeslink et al.
2010/0318114 A1 12/2010 Pranevicius et al.
2011/0034986 A1 2/2011 Chou et al.
2011/0144742 A1 6/2011 Madrid et al.
2011/0172696 A1 7/2011 Jeffrey et al.
2011/0196412 A1 8/2011 Levit et al.
2011/0202084 A1 8/2011 Hoem et al.
2011/0295177 A1 12/2011 Mohl
2011/0295301 A1 12/2011 Hoem et al.
2011/0295302 A1 12/2011 Mohl
2011/0301630 A1 12/2011 Hendriksen et al.
2012/0101413 A1 4/2012 Beetel et al.
2012/0108979 A1 5/2012 Franklin et al.
2012/0109057 A1 5/2012 Krolik et al.
2012/0116352 A1 5/2012 Rangi
2012/0130359 A1 5/2012 Turovskiy
2012/0172911 A1 7/2012 Welch
2012/0209176 A1 8/2012 Anderson
2012/0215166 A1 8/2012 Barki
2012/0271231 A1 10/2012 Agrawal
2012/0302994 A1 11/2012 Wilson et al.
2013/0053770 A1 2/2013 Aggerholm et al.
2013/0060316 A1 3/2013 Sanati et al.
2013/0102926 A1 4/2013 Eliason et al.
2013/0102929 A1 4/2013 Haight et al.
2013/0172786 A1 7/2013 Olson et al.
2013/0190619 A1 7/2013 Nudel
2013/0253467 A1 9/2013 Gianotti et al.
2013/0281869 A1 10/2013 Barbut et al.
2013/0289607 A1 10/2013 Pedersen et al.
2013/0338637 A1 12/2013 Fischer, Jr. et al.
2014/0221898 A1 8/2014 Kurrus et al.
2014/0243873 A1 8/2014 Franklin
2014/0249504 A1 9/2014 Franklin et al.
2014/0316012 A1 10/2014 Freyman et al.
2014/0364835 A1 12/2014 Allen et al.
2014/0378869 A1 12/2014 Sela et al.

(56) References Cited

U.S. PATENT DOCUMENTS

| | | | |
|---|---|---|---|
| 2015/0012031 | A1 | 1/2015 | Rago et al. |
| 2015/0039012 | A1 | 2/2015 | Solar et al. |
| 2015/0065826 | A1 | 3/2015 | Mulligan et al. |
| 2015/0133892 | A1 | 5/2015 | Joe et al. |
| 2015/0157326 | A1 | 6/2015 | Schiemanck et al. |
| 2015/0165174 | A1 | 6/2015 | Helkowski et al. |
| 2015/0272732 | A1 | 10/2015 | Tilson et al. |
| 2015/0335860 | A1 | 11/2015 | Klocke et al. |
| 2015/0367098 | A1 | 12/2015 | Aggerholm et al. |
| 2016/0000446 | A1 | 1/2016 | Eliason et al. |
| 2016/0051386 | A1 | 2/2016 | Haarmann-Thiemann |
| 2016/0213893 | A1 | 7/2016 | Franklin |
| 2016/0250444 | A1 | 9/2016 | Lampropoulos et al. |
| 2016/0375230 | A1 | 12/2016 | Lee et al. |
| 2017/0296779 | A1 | 10/2017 | Purdy et al. |
| 2019/0076152 | A1 | 3/2019 | Franklin et al. |
| 2019/0366046 | A1* | 12/2019 | Klocke .............. A61M 25/1011 |
| 2020/0022587 | A1 | 1/2020 | Glover et al. |
| 2020/0046364 | A1 | 2/2020 | Johnson et al. |
| 2021/0138187 | A1 | 5/2021 | Tilson et al. |
| 2021/0282759 | A1 | 9/2021 | Layman et al. |
| 2022/0000486 | A1 | 1/2022 | Williams et al. |
| 2023/0010482 | A1 | 1/2023 | Kornhaber et al. |
| 2023/0099085 | A1 | 3/2023 | Kim |

FOREIGN PATENT DOCUMENTS

| | | | |
|---|---|---|---|
| EP | 0492361 | A1 | 7/1992 |
| EP | 1094861 | B1 | 4/2005 |
| EP | 1658808 | A1 | 5/2006 |
| EP | 1911484 | A2 | 4/2008 |
| EP | 2389974 | A1 | 11/2011 |
| EP | 2716323 | A1 | 4/2014 |
| EP | 2837402 | A2 | 2/2015 |
| GB | 2297259 | A | 7/1996 |
| JP | H 03198868 | A | 8/1991 |
| JP | H03280962 | A | 12/1991 |
| JP | H 09-164208 | A | 6/1997 |
| JP | H1080497 | A | 3/1998 |
| JP | 2000217922 | A | 8/2000 |
| JP | 2002505165 | A | 2/2002 |
| JP | 2003535652 | A | 12/2003 |
| JP | 200714820 | A | 1/2007 |
| JP | D1341169 | | 10/2008 |
| JP | 2008546471 | A | 12/2008 |
| JP | 2011245300 | A | 12/2011 |
| JP | D1503910 | | 8/2014 |
| JP | D1676431 | | 1/2021 |
| WO | 9220398 | A1 | 11/1992 |
| WO | 9713542 | A1 | 4/1997 |
| WO | 9725093 | A1 | 7/1997 |
| WO | 9834670 | A2 | 8/1998 |
| WO | 1999/24105 | A2 | 5/1999 |
| WO | 9925417 | A1 | 5/1999 |
| WO | 9944666 | A2 | 9/1999 |
| WO | 0197743 | A2 | 12/2001 |
| WO | 2004049970 | A2 | 6/2004 |
| WO | 2006014631 | A1 | 2/2006 |
| WO | 2006115904 | A2 | 11/2006 |
| WO | 2006135853 | A2 | 12/2006 |
| WO | 2007001701 | A1 | 1/2007 |
| WO | 2007022592 | A1 | 3/2007 |
| WO | 2008013441 | A1 | 1/2008 |
| WO | 2010070685 | A1 | 6/2010 |
| WO | 2011133736 | A2 | 10/2011 |
| WO | 2014/003809 | A1 | 1/2014 |
| WO | 2014036530 | A1 | 3/2014 |
| WO | 2014134215 | A1 | 9/2014 |
| WO | 2014152191 | A1 | 9/2014 |
| WO | 2015006828 | A1 | 1/2015 |
| WO | 2015035393 | A1 | 3/2015 |
| WO | 2015191685 | A1 | 12/2015 |
| WO | 2016149653 | A2 | 9/2016 |
| WO | 2017210584 | A1 | 12/2017 |
| WO | 2019095049 | A1 | 5/2019 |
| WO | 2020033372 | A1 | 2/2020 |

OTHER PUBLICATIONS

Holcomb et al., “Causes of death in US Special Operations Forces in the global war on terrorism: 2001-2004,” Annals of Surgery, vol. 245, No. 6, pp. 986-991 (2007).
Sohn et al., “Demographics, Treatment, and Early Outcomes in Penetrating Vascular Combat Trauma,” Arch Surg, vol. 143, No. 8, pp. 783-787 (2008).
White et al., “The Epidemiology of Vascular Injury in the Wars in Iraq and Afghanistan,” Annals of Surgery, vol. 253, No. 6, pp. 1184-1189 (2011).
Fenton et al., “Comparing risks of alternative medical diagnosis using Bayesian arguments,” J. Biomed. Inf., vol. 43, pp. 485-495 (2010).
Patel et al., “Bayesian Designs for Device Clinical Trials,” MDG Forum, Waltham, MA., Nov. 3, 2010, downloaded from web page: <http://www.cytel.com/pdfs/Patel_Bayes_Devices_Slides_11.18.10.pdf>.
Guidance for the Use of Bayesian Statistics in Medical Device Clinical Trials, U.S. Department of Health and Human Services, Food and Drug Administration, Center for Devices and Radiological Health, Division of Biostatistics, Office of Surveillance and Biometrics, Feb. 5, 2010.
Int’l Preliminary Report on Patentability issued Sep. 11, 2015 in Int’l Application No. PCT/US2014/018779.
Int’l Search Report and Written Opinion issued Jun. 8, 2014 in Int’l Application No. PCT/US2014/018779.
Int’l Search Report and Written Opinion issued Oct. 14, 2011 in Int’l Application No. PCT/US2011/033368.
Sandgren et al., “The Diameter of the Common Femoral Artery in Healthy Human: Influence of Sex, Age, and Body Size,” Journal of Vascular Surgery, vol. 29, No. 3, pp. 503-510 (1999).
Sam II et al., “Blunt Traumatic Aortic Transection: Endoluminal Repair with Commercially Available Aortic Cuffs,” Journal of Vascular Surgery, vol. 38, No. 5, pp. 1132-1135 (2003).
Peterson et al., “Percutaneous endovascular repair of blunt thoracic aortic transection,” Journal of Trauma, vol. 59, No. 5, pp. 1062-1065 (2005).
Office Action issued Oct. 28, 2014 in U.S. Appl. No. 13/642,465, by Eliason.
Office Action issued Apr. 6, 2015 in U.S. Appl. No. 13/642,465, by Eliason.
Stannard et al., “Resuscitative Endovascular Balloon Occlusion of the Aorta (REBOA) as an Adjunct for Hemorrhagic Shock,” J. Trauma, vol. 71, pp. 1869-1872 (2011).
Ledgerwood et al., “The Role of Thoracic Aortic Occlusion for Massive Hemoperitoneum,” J Trauma, vol. 16, No. 8, pp. 610-615 (1976).
Detrano et al. “Bayesian Probability Analysis: a Prospective Demonstration of its Clinical Utility in Diagnosing Coronary Disease,” Circulation, vol. 69, No. 3, pp. 541-547 (1984).
Int’l Search Report and Written Opinion issued Jan. 28, 2015 in Int’l Application No. PCT/US2014/054802.
Int’l Preliminary Report on Patentability issued Mar. 24, 2016 in Int’l Application No. PCT/US2014/054802.
Int’l Preliminary Report on Patentability issued Nov. 1, 2012 in Int’l Application No. PCT/US2011/033368.
Langewouters et al., “The static elastic properties of 45 human thoracic and 20 abdominal aortas in vitra and the parameters of a new model,” Journal of Biometrics, vol. 17, No. 6, pp. 425-435 (1984).
Hughes, “Use of an Intra-Aortic Balloon Catheter Tamponade for Controlling Intra-Abdominal Hemorrhage in Man,” Surgery, vol. 36, pp. 65-68 (1954).
Office Action issued Aug. 23, 2016 in AU Application No. 2015274743.
Extended European Search Report issued Oct. 5, 2016 in Europe Application No. EP 14 75 6640.

(56) References Cited

OTHER PUBLICATIONS

Supplemental Search Report issued Dec. 19, 2016 in EP Application No. 15806534.
Int'l Preliminary Report issued Dec. 22, 2016 in Int'l Application No. PCT/US2015/035061.
Int'l Search Report and Written Opinion issued Sep. 4, 2015 in Int'l Application No. PCT/US2014/035061.
Extended Search Report issued Mar. 24, 2017 in EP Application No. 14842370.
Int'l Search Report and Written Opinion issued Apr. 21, 2017 in Int'l Application No. PCT/US2016/023223.
Extended Search Report issued Mar. 21, 2017 in EP Application No. 15806534.
Office Action issued Apr. 11, 2017 in JP Application No. 2016-546035.
Office Action issued Mar. 20, 2017 in CA Application No. 2,797,237.
Extended European Search Report issued Jun. 26, 2017 in EP Application No. 14842370.
Int'l Preliminary Report issued Jul. 17, 2017 in Int'l Application No. PCT/US2016/023223.
Int'l Search Report and Written Opinioin issued Sep. 28, 2017 in Int'l Application No. PCT/US2017/035729.
Office Action issued Sep. 19, 2017 in JP Application No. 2015-559309.
Office Action issued Sep. 12, 2017 in JP Application No. 2016-546035.
Office Action issued Oct. 12, 2017 in CA Application No. 2,980,018.
Chen et al., "The Renal Length Nomogram: A Multivariable Approach," The Journal of Urology, vol. 168, pp. 2149-2152 (Nov. 2002).
Office Action issued Aug. 27, 2018 in U.S. Appl. No. 14/917,286, by Franklin.
Int'l Search Report and Written Opinion issued Oct. 18, 2019 in Int'l Application No. PCT/US19/45252.
Int'l Search Report and Written Opinion issued Jun. 8, 2022 in Int'l Application No. PCT/US2022/020704.
European Search Report Issued May 31, 2022 in European Application No. 19846055.2.
Office Action issued Jan. 9, 2023 in U.S. Appl. No. 16/133,193.
Int'l Search Report and Written Opinioin issued Apr. 16, 1997 in Int'l Application No. PCT/US96/20302.
Notice of Allowance issued Apr. 20, 2023 in U.S. Appl. No. 16/133,193.
M. Austin Johnson et al. (published on May 27, 2016). Partial Resuscitative Balloon Occlusion of the Aorta (P-REBOA): Clinical Technique and Rationale, J Trauma Acute Care Surg, 81(5) Suppl 1:S133-S137.
Rachel M. Russo et al. (presented at the Military Surgical Symposium, Nashville, TN in Apr. 2015, published on Apr. 29, 2016). Partial Resuscitative Endovascular Balloon Occlusion of the Aorta in Swine Model of Hemorrhagic Shock, J Am Coll Surg, 223:359-368.
Rachel M. Russo et al. (published on Dec. 14, 2015. Extending the Golden Hour: Partial Resuscitative Endovascular Balloon Occlusion of the Aorta in a Highly Lethal Swine Liver Injury Model, J Trauma Acute Care Surg (80)3:372-380.
Extended Search Report issued May 10, 2023 in European Application No. 22743436.2.
Office Action issued Jun. 20, 2023 in U.S. Appl. No. 17/563,669.
Office Action issued Mar. 25, 2024 in U.S. Appl. No. 17/563,629.
Office Action issued Mar. 26, 2024 in U.S. Appl. No. 17/717,624.
Office Action issued May 29, 2024 in U.S. Appl. No. 17/563,629.
Office Action issued Aug. 28, 2024 in U.S. Appl. No. 17/563,629.
Office Action issued Oct. 2, 2024 in U.S. Appl. No. 29/824,018.
Bridge occlusion balloon submitted for FDA-Cardiac Rhythm News, posted Dec 9, 2015 [retrueved online May 10, 2024]. Retrieved from internet, https://cardiacrhythmnews.com/bridge-occlusion-balloon-submitted-for-fed-210k-premarket-notification-for-lead-extraction-procedu (Year: 2015).
Gore Molding & Occlusion Balloon—Gore Medical, posted date unavailable [retrieved online Oct. 5, 2024]. Retrieved from internet, <https://wwww.goremedical.com/products/mob> (Year: 2024).
NC Emerge PTCA Dilation Catheter—Boston Scientific, posted date unavailable [retrieved online May 10, 2024]. Retrieved from internet, <https://www.bostonscientificcom/en-EU/products/catheters-balloon/nc-emerge-balloon-catheter.html> (Year 2024).
Philips-Bridge Occlusion balloon, posted date unavailable [retrieved online May 10, 2024]. Retrieved from internet, <https://www.usa.philipscom/healthcare/product/HCIGTDBOB/bridge-occlusion-balloon> (Year: 2024).
pREBOA-PRO-Get Ready-Prytime Medical, posted date unavailable [retrieved online May 10, 2024]. Retrieved from internet, https://prytimemedical.com/getready/#panel2 (Year: 2024).
TransForm—Stryker, posted date unavailable [retrieved online May 10, 2024]. Retrieved from internet, <https://www.stryker.com/us/en/neurovascular/products/transform-occlusion-balloon-catheter.html> (Year: 2024).
Scott et al., A novel fluoroscopy-free, resuscitative endovascular aortic balloon occlusion system in a model of hemorrhagic shock, The Journal of Trauma and Acute Care Surgery, vol. 75, Issue 1 (Jul. 2013).
Park et al., Resuscitative Endovascular Balloon Occlusion of the Aorta (REBOA): Comparison With Immediate Transfusion Following Massive Hemorrhage in Swine, WTA 2015 Plenary Paper, J. Trauma Acute Care Surg, vol. 79, No. 6 (Feb. 27, 2015).
Neuzil et al., Balloon technology for catheter ablation of atrial fibrillation, Cor et Vasa 54, E401-E407 (2012).
Spiotta et al., Balloon remodeling for aneurysm coil embolization with the coaxial lumen Scepter C balloon catheter: initial experience at a high volume center, J. NeuroIntervent Surg 2013, 5:582-585 (Nov. 7, 2012).
Tokai Medical Products Co., TMP Lock Balloon Catheter Set Product Insert (Oct. 18, 2013).
Gerstenfeld et al., Pulmonary vein isolation using a compliant endoscopic, Springer Science+Business Media, LLC (2010).
Deaton, Image-Guided Thrombectomy in Vascular Surgery, Endovascular Today (Jul. 2005).
Mathis, et al., Physicalcharacteristics of Balloon Catheter Systems Used in Temporary Cerebral Artery Occlusion, Amercian Society of Neuroradiology (Nov. 1994).
Gu et al., A New Technique for Sizing of Atrial Septal Defects, Catheterization and Cardiovascular Interventions, Jan. (1999).
Saab, Applications of High-Pressure Balloons in the Medical Device Industry , Medical Device & Diagnostic Industry Magazine, Sep. 2000.
Chengod, et al., Selective Left Bronchial Intubation and Left-Lung Isolation in Inffants and Toddlers: Analysis of a New Technique, Department of Anesthesiology and Intensive Care, Division of Cardiothoracic and Vascular Anesthesiology and Intensive Care, Amrita Institute of Medical Sciences and Research Center, Kerala, India, . of Cardiothoracic and Vascular Anesthesia, vol. 19, No. 5, at 636-41 (Oct. 2005).
Gal et al., First Dutch experience with the endoscopic laser balloon ablation system for the treatment of atrial fibrillation, Neth Heart J (2015) 23 :96-99 (Nov. 12, 2014).
Metzner et al., One-year clinical outcome after pulmonary vein isolation using the novel endoscopic ablation system in patients with paroxysmal atrial fibrillation, Heart Rhythm, vol. 8, No. 7 (Jul. 2011).
Phillips et al., Anatomic Location of Pulmonary Vein Electrical Disconnection with Balloon-Based Catheter Ablation, Journal of Cardiovascular Electrophysiology, vol. 19, No. 1 (Jan. 2008).
Office Action issued Nov. 14, 2024 in U.S. Appl. No. 17/563,629.
Office Action issued Feb. 25, 2025 in U.S. Appl. No. 17/717,624.
Tohyama O, et al.: "A fiber-optic pressure microsensor for biomedical applications", Sensors and Actuators A: Physical, Elsevier BV, NL, vol. 66, No. 1-3, Apr. 1, 1998 (Apr. 1, 1998), pp. 150-154, XP004143984, ISSN: 0924-4247, DOI: 10.1016/S0924-4247 (97) 01764-0.
Office Action issued May 19, 2025 in U.S. Appl. No. 17/563,629.
Office Action issued Aug. 26, 2025 in U.S. Appl. No. 17/717,624.
Office Action issued Aug. 28, 2025 in U.S. Appl. No. 17/563,629.

(56) References Cited

OTHER PUBLICATIONS

Handbook of Endovascular Peripheral Interventions (C.D. Owens & Y. Yeghiazarians eds., Springer 2012).
Patent Owner Prytime Medical Inc. "Leadership" web page (available at https://prytimemedical.com/prytime-medical/leadership/) (last visited May 1, 2024).
Definition of "Secure," Webster's New Universal Unabridged Dictionary (1996).
Printout of http://www.jcvaonline.com/ (Apr. 9, 2025).
Printout of http://evtoday.com/about (Apr. 9, 2025).
Printout of https://journals.lww.com/jtrauma/pages/aboutthejournal.aspx (Apr. 9, 2025).
Printout of https://www.jscai.org/content/aims (Apr. 9, 2025).
Printout of https://scai.org/publications/jscai-editorial-board (Apr. 9, 2025).
Office Action issued Mar. 19, 2026 in U.S. Appl. No. 17/563,629.

* cited by examiner

OCCLUSION CATHETER SYSTEM FOR PARTIAL OCCLUSION OR FULL OCCLUSION

CROSS-REFERENCE TO RELATED APPLICATIONS

The present application is a continuation of U.S. patent application Ser. No. 17/563,629, filed Dec. 28, 2021, which is a continuation of U.S. patent application Ser. No. 16/133,193, filed Sep. 17, 2018 and titled, "System and Method for Low-Profile Occlusion Balloon Catheter," and issued as U.S. Pat. No. 11,672,951 on Jun. 13, 2023, which is a continuation of U.S. patent application Ser. No. 15/551,504, filed Aug. 16, 2017 and titled, "System and Method for Low-Profile Occlusion Balloon Catheter," and issued as U.S. Pat. No. 10,149,962 on Dec. 11, 2018, which is a Section 371 of International Patent Application No. PCT/US2016/023223, filed Mar. 18, 2016, which was published in English on Sep. 22, 2016 as International Publication No. WO 2016/149653 and claims the benefit of U.S. Provisional Patent Application Nos. 62/135,552, filed Mar. 19, 2015 and titled, "Anti-Hypertensive Vascular Occlusion Catheter and Method," 62/135,528, filed on Mar. 19, 2015 and titled, "Anti-Hypertensive Vascular Occlusion Catheter with Electromechanical Actuation and Method," 62/135,576, filed Mar. 19, 2015 and titled, "Anti-Hypertensive Vascular Occlusion Catheter and Method," 62/135,603, filed Mar. 19, 2015 and titled, "Anti-Hypotensive Vascular Occlusion Catheter with Electromechanical Actuation Method," 62/135,609, filed Mar. 19, 2015 and titled, "Control Processing System for Regulating Vascular Occlusion and Method," 62/136,123, filed Mar. 20, 2015 and titled, "System and Apparatus for Vascular Pre-Conditioning and Method," 62/136,152, filed Mar. 20, 2015 and titled, "Vascular Pre-Conditioning Occlusion Catheter and Method," 62/136,180, filed Mar. 20, 2015 and titled, "Vascular Occlusion Catheter with Infusion Capability and Method," 62/136,230, filed Mar. 20, 2015 and titled, "Vascular Occlusion-Perfusion Catheter and Method," 62/136,326, filed Mar. 20, 2015 and titled, "Vascular Occlusion Catheter with Variable Perfusion Flow and Method," 62/136,370, filed Mar. 20, 2015 and titled, "Vascular Occlusion-Perfusion Catheter with Plural Occlusion Members and Method," 62/136,390, filed Mar. 20, 2015 and titled, "Vascular Occlusion-Perfusion Catheter with Mechanically Actuated Variable Occlusion-Perfusion Properties and Method," 62/136,571, filed Mar. 22, 2015 and titled, "Low Profile Sensing Vascular Occlusion Catheter and Method of Vascular Occlusion," and 62/204,804, filed Aug. 13, 2015 and titled, "System and Method for Low-Profile Occlusion Balloon Catheter," the entire contents of each of which are incorporated by reference herein in their entireties.

STATEMENT REGARDING FEDERALLY SPONSORED RESEARCH OR DEVELOPMENT

This invention was made with government support under Contract No. W911QY-15-C-0099 and grant title "Resuscitative Endovascular Balloon Occlusion of the Aorta (REBOA) Research", awarded by U.S. Army Medical Materiel Agency. The government has certain rights in the invention.

BACKGROUND OF THE INVENTION

The present invention pertains generally to vascular occlusion catheters and methods of vascular pre-conditioning while controlling occlusion and perfusion during an occlusion procedure. Pre-conditioning is employed to mitigate ischemia before, during and/or after a vascular occlusion procedure, as well as used to reduce or ameliorate the onset of hypertension during or reduce or ameliorate the onset of hypotension after a vascular occlusion procedure. Vascular occlusions may be indicated in either the venous system and/or the arterial system. Endoarterial occlusion is a procedure in which a blood vessel is at least partially occluded in order to restrict blood flow upstream or downstream the occlusion site for purposes of a vascular procedure or repair. It is known that transient hypertension is a risk factor in arterial occlusion, particularly aortic occlusion. Transient hypertension occurs when the blood pressure upstream the occlusion site rises to a potentially unsafe level during the time duration of the occlusion. Upon completion of a procedure requiring arterial occlusion, particularly aortic occlusion, care must be taken during the process of reestablishing blood flow to reduce or ameliorate the onset of hypotension. Thus, arterial occlusion carries with it two twin risks, hypertension during the occlusion and hypotension as the occlusion is withdrawn and blood flow restored, that must be managed.

Temporary aortic occlusion as an operative method to increase proximal or central perfusion to the heart and brain in the setting of shock due to major trauma is generally known. Despite potential advantages over thoracotomy with aortic clamping, resuscitative endovascular balloon occlusion of the aorta ("REBOA") for trauma has not been widely adopted.

Many attempts have been made at developing technologies to control non-compressible abdominal hemorrhage. For example, non-occlusive, abdominal tamponade procedures have been developed to address the problem of non-compressible hemorrhage, such as providing introducing an expandable biocompatible foam into the abdominal cavity to apply pressure to the abdominal organs and vasculature. Pharmacological efforts have also been developed to address the problem of non-compressible hemorrhage. Conventional REBOA procedures are typically performed in an operating room and with the aid of fluoroscopy of other imaging.

Devices that automate inflation and deflation of a balloon are known. Intra-aortic balloon counterpulsation catheters for blood pressure augmentation coordinated with electrocardiography signals are also known. Over inflation safety devices are also known, such as a pressure-relief valve coupled to an inflation lumen that opens when pressure within the inflation lumen exceeds a threshold pressure, but is still that relative pressure within the balloon necessary to maintain occlusion of the blood vessel.

It would be desirable to design, develop and implement a system that intermittently and automatically releases an occlusion by releasing apposition of an occlusive member against the vascular wall and allowing perfusion past the occlusion member in response to a physiological parameter, then re-establishing occlusion in response to potential changes in the physiological parameter, either during a vascular repair procedure to control hypertension or post-repair procedure to control hypotension.

BRIEF SUMMARY OF THE INVENTION

In accordance with a preferred embodiment of the present invention, there is provided an arterial occlusion catheter system including an occluding member carried at a distal aspect of a catheter, an atraumatic guiding tip forming a distal end of the catheter and a pressure accumulator communicating with the occluding member. The atraumatic guiding tip alleviates the need for a guide wire, and, therefore for initial guide wire placement, allowing the preferred arterial occlusion catheter to be used in field operations and without the necessity of fluoroscopy or other imaging modality.

In accordance with another preferred embodiment of the present invention, there is provided an arterial occlusion catheter system including an occluding member carried at a distal aspect of a catheter, an atraumatic guiding tip forming a distal end of the catheter, a pressure valve communicating with the occluding member that release expansive force applied to the occluding member to allow perfusion past the occluding member when hypertension is present, and a means for re-applying the expansive force to re-establish occlusion when the arterial pressure is normalized.

In accordance with still another preferred embodiment of the present invention, there is provided an arterial occlusion catheter system having a computer hardware and software control over the physiological parameter set points at which automatic computer controlled occlusion or release of occlusion occur, including, without limitation, set points for systolic and/or diastolic arterial blood pressure, heart rate, heart rhythm (including, without limitation, the P, Q, R, S, T and U peaks, their size, timing and duration), blood oxygenation, tissue oxygenation or the presence or absence of metabolic blood products.

In accordance with yet still another preferred embodiment of the present invention, there is provided an arterial occlusion catheter system having computer hardware and software control monitoring physiological parameter set points for systolic and/or diastolic arterial blood pressure, heart rate, heart rhythm (including, without limitation, the P, Q, R, S, T and U peaks, their size, timing and duration), blood oxygenation, tissue oxygenation or the presence or absence of metabolic blood products and which provides visual, auditory or tactile feedback to a medical practitioner as signals for the medical practitioner to take certain recommended actions based upon the monitored physiological parameter set points.

In accordance with still yet another preferred embodiment of the present invention, there is provided an arterial occlusion system and method in which fluids, such as blood, plasma, saline, blood products or blood substitutes, are infused proximal and/or distal the occlusion site.

In accordance with another preferred embodiment of the present invention, there is provided an arterial occlusion system and method in which the occlusion member has a geometric conformation such that at different degrees of deployment it assumes different transverse geometric profiles that yield different degrees of arterial occlusion and permit perfusion past the occlusion member. The occlusion member may have a torroidal shape when fully deployed and a fluted or corrugated shape with longitudinally oriented flutes or corrugations and valleys between adjacent flutes or corrugations when in its partially deployed state. Alternatively, the occlusion member may have a helical shape when either fully or partially deployed, such that fluid flow around the occlusion member is maintained while at least partially occluding the artery. Further, the occlusion member may have a torroidal shape with vanes, the vanes being either longitudinally oriented or helically oriented, the vanes being sufficiently pliant so that they deflect and fold against the occlusion member when the occlusion member is in full apposition with the vascular luminal wall surface, but pliantly recover to project from the occlusion member and define fluid flow pathways between adjacent vanes and past the occlusion member.

In accordance with yet another preferred embodiment of the present invention, there is provided an arterial occlusion system and method having a catheter with at least one occlusion member at a distal end thereof, a plurality of fluid flow ports communicating with a common fluid flow lumen within the catheter and an luminal occluding member that is movable within the common fluid flow lumen to open or close one or more of the plurality of fluid flow ports, thereby controlling the volume and rate of perfusion fluid flow past the at least one occlusion member.

While in all preferred embodiments of the present invention, the occluding member is preferably a balloon, the occluding member may also consist of a woven or non-woven shape memory metal membrane, a superelastic metal membrane, an elastic metal membrane, a woven or non-woven polymer material or a shape memory polymer and that the occluding member may or may not be supported by an expansive or reinforcing frame.

As noted above, arterial hypertension is a frequent result of arterial occlusion for any clinically significant period of time, particularly, in aortic occlusion situations. A need has been recognized to provide a catheter system in which clinically significant hypertension is alleviated automatically and without medical practitioner intervention or control, concurrently with the arterial pressure exceeding a pre-determined level upstream in the blood flow from the occlusion member.

The preferred present invention generally relates to endovascular arterial occlusion catheters that are particularly well suited to emergency or trauma use for REBOA procedures to occlude non-compressible hemorrhage either in the field, on the battlefield or in emergency room environments where guidance imaging is typically not available. More particularly, the preferred present invention pertains to an arterial occlusion catheter that has an atraumatic guiding tip made of a generally flexible material, elastic material, shape memory material or superelastic material. The atraumatic guiding tip may be formed at least in part of elastomeric polymer that permits guide wire and fluoroscopy free guidance of the arterial occlusion catheter to the site requiring occlusion. Still more particular, the present invention relates to a low profile aortic occlusion catheter having an atraumatic guiding tip formed of polymer, metal or polymer reinforced with an elastic, shape memory or superelastic material and having a lumen for introducing or withdrawing fluids from a body into which the catheter is placed and/or for introducing sensors, adjunctive medical devices or other diagnostic or therapeutic modalities, to determine and evaluate a condition within the body, such as arterial pressure or flow rate, to diagnose a condition in the body and/or to treat a condition in the body.

Balloon catheters generally comprise an elongated catheter shaft with a deflated balloon on the distal end of the shaft, and are used in a number of different medical procedures, including, for example, angioplasty, stent placement, occlusion, drug delivery, etc. The catheter is introduced through a percutaneous sheath and maneuvered into the patient's blood vessels until the balloon is properly positioned across the stenotic area to be dilated. Once properly in position, the balloon is inflated with liquid one or more times to a predetermined size and pressure to widen the coronary passageway and increase blood flow.

It is desirable for balloon catheters to attain very low profiles in order to facilitate passage of the balloon across severe and remote vascular obstructions. High strength materials are commonly required in the design of balloon catheter components to prevent shaft buckling when the balloon is inflated. Additionally, high strength materials are required so that torque applied to the proximal end of the catheter results in rotation of the distal tip of the catheter. High flexibility materials are also commonly required in the design of balloon catheter components to maintain a low-profile and avoid trauma or perforation of the blood vessels while the catheter is maneuvered through the patient's tortuous vasculature.

However, conventional balloon catheters, particularly those designed for aortic occlusion, generally do not properly balance the need for proximal segment stiffness with the need for a low profile, flexible distal segment and trackability through the tortious vascular pathway without entry into collateral vessels. A low profile balloon catheter with a high strength and relatively stiff proximal segment and a flexible distal segment with an atraumatic tip having a design that restricts tracking and entry into collateral vessels, which is employed by preferred embodiments of the present invention.

In one preferred embodiment, the devices comprise an elongate catheter having a proximal and a distal region. The catheter may also have a lumen extending between the proximal and distal regions. An expandable occlusion member, e.g., a balloon, a membrane with or without an expandable frame or an expandable section of the catheter itself, is carried at the distal region of the catheter. The catheter in certain preferred embodiments may include plural expandable occlusion members, i.e., second, third, fourth, etc. expandable occlusion members, at the distal region of the catheter, proximal and/or distal the first expandable occlusion member.

In certain preferred embodiments, the catheter will also include means for measuring physiological parameters distal and/or proximal one or more of the expandable occlusion members, including, for example blood pressure sensors, heart rate sensors, flow sensors, chemical sensors, temperature sensors, oxygenation sensors, ischemia sensors, biological sensors, imaging sensors or the like.

In use, the catheter having one expandable device is located in the descending aorta so that the expandable device is suprarenal or infrarenal. The expandable device is then expanded to partially or completely obstruct the descending aorta. Cerebral blood flow and cerebral blood pressure rises and is maintained at an increased level, as desired. Cephalic blood pressure and/or cerebral blood flow may be monitored, and the expandable device adjusted as needed. Therapeutic instruments may be deployed through the lumen (when present) of the occlusion catheter systems.

In another preferred embodiment, the occlusion member, when expanded, has a maximum periphery that conforms to the inner wall of the vessel, thereby providing a sealed contact between it and the vessel wall. The occlusion catheter system may have a blood flow or other fluid flow conduit allowing blood flow from a location upstream to a location downstream. The preferred devices further include a variable flow mechanism in operative association with the blood conduit, thereby allowing blood flow through the conduit to be adjusted and controlled. The preferred devices can optionally include a manometer and/or pressure limiter to provide feedback to the variable flow mechanism for precise control of the upstream and downstream blood pressure.

In certain preferred embodiments of the invention, the arterial occlusion catheter system includes an additional access lumen that allows access and passage of other medical devices or adjunctive therapies. Devices, such as flow wires, imaging catheters or devices, infusion, atherectomy, angioplasty, hypothermia catheters or devices, or electrophysiologic study (EPS) catheters, can be introduced through the additional access lumen to access a position in the blood vessel to provide diagnostic or therapeutic interventions. Hypothermia is one example of an adjunctive therapy that may be delivered using the additional access lumen of the preferred arterial occlusion catheter. Where cerebral cooling is desired the additional access lumen may be used to introduce cooled blood or other cooled fluids, a cooling wire, or other type of heat exchanger, such as a cooling catheter.

In still another preferred embodiment, the occlusion member comprises a first balloon mounted to a distal end of the catheter, and a second balloon mounted on the distal end of the catheter and proximal the first balloon, with a region of the catheter being intermediate the first and the second balloons. The first balloon has a first balloon inflation chamber and the second balloon has a second balloon inflation chamber, the first balloon inflation chamber and the second balloon inflation chamber may communicate with a common inflation lumen or, alternatively, may communicate with separate inflation lumens, termed herein, first inflation lumen and second inflation lumen, such that the first and second balloons are either concurrently or separately inflatable. A perfusion lumen may also be provided in the catheter and communicates with perfusion openings passing through the wall of the catheter to permit fluids, including blood and blood products to be introduced through the catheter. The perfusion openings are preferably located distal the first balloon (first perfusion openings), proximal the first balloon and intermediate the first balloon and the second balloon (second perfusion openings), and/or proximal the second balloon (third perfusion openings), or in any combination thereof, such that fluid flow may be established either concurrently or selectively through all of or only some of the perfusion openings. Selective fluid flow through the perfusion openings may be accomplished in a number of alternative manners. For example, a plurality of perfusion lumens may be provided in the catheter. A first perfusion lumen communicating with the perfusion openings distal the first balloon, a second perfusion lumen communicating with the perfusion openings proximal the first balloon and intermediate the second balloon and the first balloon, and a third perfusion lumen communicating with the perfusion openings proximal the proximal balloon. Alternatively, a single common perfusion lumen may communicate with all of the perfusion openings, and a selector member is disposed within the perfusion lumen and movable within the perfusion lumen to selectively expose only those perfusion lumens in the catheter regions through which perfusion is desired. A non-limiting example of a selector member comprises a tubular hypotube having non-fenestrated wall surfaces that is longitudinally movable within the perfusion lumen to select either the first perfusion openings, the second perfusion openings or the third perfusion openings, or portions thereof. The hypotube may, itself, have fenestrations or openings passing through its wall surfaces, wherein rotational movement of the fenestrated hypotube within the perfusion lumen will align the hypotube fenestrations with one or more of the perfusion openings to permit fluid flow from the lumen of the hypotube and through the aligned fenestrations and perfusion openings and into the vascular structure.

It will be understood that there are many advantages in using the partial aortic occlusion devices and methods disclosed herein. For example, the devices can be used (1) to provide variable partial occlusion of a vessel; (2) to augment and maintain cerebral perfusion in patients suffering from global or focal ischemia; (3) to condition the brain or spinal cord to secrete neuroprotective agents prior to a major surgery which will necessitate reduced cerebral or spinal perfusion; (4) to prolong the therapeutic window in global or focal ischemia; (5) to accommodate other medical devices, such as an atherectomy catheter; (6) prophylactically by an interventional radiologist, neuroradiologist, or cardiologist in an angiogram or fluoroscopy suite; (7) for prevention of cerebral ischemia in patients undergoing procedures, such as coronary catheterization or surgery, where cardiac output might fall as a result of arrhythmia, myocardial infarction or failure; (8) to treat shock, thereby eliminating or reducing the use of systemic vasoconstrictors; (9) to prevent hypotensive neurologic damage during carotid stenting, and (10) to rescue vasospasm induced by hemorrhage or interventional procedures.

Provided herein are systems, methods and compositions for an occlusion balloon catheter system comprising: a first catheter member having a first lumen extending longitudinally through the first catheter member and open at a distal end of the first catheter member; a second catheter member having a second lumen extending longitudinally through the second catheter member and open at a distal end of the second catheter member, the second catheter member is positioned over and in spaced apart relationship relative to a proximal section of the first catheter member forming an annular space between the second catheter member and the first catheter member, the proximal section of the first catheter member resides within the second lumen of the second catheter member and the first catheter member extends beyond the distal end of the second catheter member, a third catheter member that may comprised a proximal shaft of an atraumatic tip having a third lumen extending longitudinally and partially through the third catheter member; the third catheter member is positioned over a distal section of the first catheter member, the third catheter member having a distal section that extends distally from a distal end of the first catheter member such that the first lumen and the third lumen are in fluid flow communication, whereby the second and third catheter are spaced apart from each other along a longitudinal axis of the first catheter member with the first catheter member extending therebetween; an atraumatic tip member having a proximal section co-axially coupled to a distal end of the third catheter member; and a balloon coupled at its proximal end to the second catheter member and at its distal end to the third catheter member and in fluid flow communication with the second catheter member; the balloon being positioned such that the space between the second catheter member and the third catheter member is within the balloon.

REBOA is preferably performed, as follows:

Step 1: Arterial Access and Positioning of Initial Sheath

Access to the arterial circulation for REBOA for trauma is obtained through the femoral artery. After femoral artery access is obtained, a ten to fifteen centimeter (10-15 cm) long sheath is positioned in the femoral and external iliac artery. Access to the femoral artery can be obtained using several techniques, including: percutaneous, open exposure (i.e., cut down), or exchange over a guide wire from an existing femoral arterial line. Percutaneous access is commonly accomplished under ultrasound guidance. Ultrasound or direct surgical identification of the femoral artery lateral to the vein is preferred in the hypotensive patient without a palpable pulse. Once identified, the artery should be entered at a forty-five degree (45°) angle with a hollow eighteen gauge (18-gauge) needle through which a thirty-five thousandths inch (0.035") wire or similarly sized wire can be passed. After the wire has been passed into the artery, the needle is removed and a small incision made at the interface of the wire and the skin. Next the sheath is placed over the wire into the artery. Any time a sheath is passed over a wire into the arterial system, the sheath's internal dilator is preferably firmly in place to allow a smooth reverse taper from the wire to the diameter of the sheath. Once the dilator and sheath have been advanced over the wire through the skin into the artery, the dilator is removed leaving the sheath as a working port through which other maneuvers can be accomplished.

Step 2: Selection and Positioning of the Balloon

Selection of a Balloon: A balloon inflated inside the aorta to occlude flow should be compliant and of large diameter. Stiff or noncompliant balloons pose a risk of arterial damage.

Positioning of the Balloon (Zones of the Aorta): Balloon selection should be made in view of the aortic zone to be occluded. Aortic zones can be considered I, II, and III spanning from cranial or proximal to caudal or distal. Zone I is preferably considered the descending thoracic aorta between the origin of the left subclavian and celiac arteries. Zone II preferably represents the para-visceral aorta between the celiac and the lowest renal artery and zone III preferably represents the infrarenal abdominal aorta between the lowest renal artery and the aortic bifurcation, depending on patient anatomy. In most instances of shock and pending cardiovascular collapse, the aim is to position the occlusive balloon to occlude zone I. In this case, a larger diameter balloon and a longer sheath are advanced into the thoracic aorta. REBOA in zone I typically requires a longer sheath, such as a sheath having a forty-five to sixty centimeter (45-60 cm) length, to be positioned in the descending thoracic aorta to support or hold the balloon against aortic pulsation once it is inflated. Inflation of a compliant balloon in aortic zone III may provide specific utility in cases of pelvic or junctional femoral hemorrhage. In this instance, a relatively smaller diameter balloon may be sufficient. Because the aortic bifurcation will support or hold the inflated balloon against pulsation, this maneuver can potentially be accomplished using a large diameter but shorter sheath, such as ten to fifteen centimeters (10-15 cm).

Wire Control and Positioning of the Large Sheath and Balloon: Positioning of the balloon in the aorta preferably takes place over a thirty-five thousands inch (0.035") wire, but is not so limited, and through an appropriately sized sheath that takes the place of the initial sheath previously described. Re-sheathing may be accomplished by inserting a two hundred sixty centimeter (260 cm) long, thirty-five thousands inch (0.035") stiff wire (e.g., Amplatz Stiff Wire Guide; Cook Medical) through the initial sheath in the femoral artery. The stiff wire is preferably advanced under fluoroscopic guidance or visualization such that the floppy tip is in the distal aortic arch. The extent of the wire outside of the sheath at this point should be noted and marked so that the wire is not advanced or withdrawn significantly, such as by more than five centimeters (>5 cm). Failure to maintain control of the wire's insertion depth during this and subsequent maneuvers may result in inadvertent injury to coronary or cerebral vessels if it is advanced too far or an inability to advance the balloon to the occlusion zone if it is withdrawn.

The initial sheath may be removed and backed off of the wire with pressure held proximally over the femoral artery for hemostasis. The larger sheath is then advanced over the wire, preferably lead by its internal dilator, through the skin opening and into the femoral and iliac artery. In this manner, the wire acts as a rail over which the large sheath or balloon catheter can be advanced or withdrawn as the operator focuses on the fluoroscopic image.

To occlude zone I, the larger, longer sheath is preferably advanced over the stiff wire under fluoroscopic guidance into the thoracic aorta to the desired location of occlusion. Fluoroscopically, zone I can be estimated to exist above the twelfth ($12^{th}$) rib and below the medial head of the clavicle. Next, the internal dilator is preferably removed from the sheath and the back end of the extended wire. The balloon is next preferably loaded on and advanced over the stationary wire into and through the sheath. Under fluoroscopic visualization, after the balloon advances from the end of the sheath, it is ready to be inflated. To occlude zone III typically requires a large diameter but shorter sheath, such as ten to twenty-five centimeters (10-25 cm), to allow passage of the balloon into the terminal aorta under fluoroscopic visualization. The concept in this scenario is that once the balloon is inflated, any aortic pulsation will push the balloon to the terminal aorta and its bifurcation.

Step 3: Inflation of the Balloon and Securing of the Apparatus

Balloon Inflation: Similar to step 2, inflation of the balloon is preferably accomplished under fluoroscopic guidance. A large-volume syringe, usually thirty to sixty milliliters (30-60 mL) is filled with a half and half solution of sterile saline and iodinated contrast. This mixture allows visualization of the balloon inflation as well as more rapid inflation and deflation times by reducing viscosity. Preferably with fluoroscopy, the balloon is inflated until the outer edges of the balloon change from convex to parallel as the balloon takes on the contour of the aortic wall. One may notice that during systole, the balloon changes shape and creates a "mushroom cap" as it is pulsed inferiorly. In zone I occlusion, the previously positioned long sheath can then support the balloon and maintain its position within the aorta. When inflation appears adequate to gain aortic wall apposition and augment central blood pressure, the three-way stopcock on shaft of the balloon should be turned off toward the balloon to maintain inflation and occlusion while other maneuvers are undertaken.

Securing the Inflated Balloon, Sheath, and Wire Apparatus: It is next preferred to hold the balloon, sheath, and wire securely so that none generally change position as the central aortic pressure returns pushing the balloon caudal. Although the balloon, sheath, and wire can be secured with sutures or an occlusive dressing that pin the apparatus to the patient, these are preferably observed continuously to limit downward or caudal migration.

Step 4: Deflation of the Balloon

Once a decision to attempt deflation is made, care is preferably taken to deflate the balloon slowly as this step can be anticipated to result in a decrease in afterload and hypotension. After prolonged balloon inflation or in situations where incomplete resuscitation has occurred, deflation of the balloon can potentially result in reperfusion, washout of metabolic byproducts, and acidosis. As such, intermittent balloon inflation and deflation is preferred until some hemodynamic stability is restored.

Step 5: Removal of the Balloon and Sheath

After REBOA is no longer required, the deflated balloon and wire are preferably removed from the large sheath which is preferably flushed with heparinized saline, such as one hundred milliliters (100 mL) of saline or one thousand (1,000) units of heparin. The relatively large diameter sheaths used to deploy currently available compliant balloons are best removed with open surgical exposure of the femoral artery. This can be accomplished using a longitudinal or transverse groin incision with dissection through the soft tissues overlying the femoral sheath. The femoral artery proximal and distal to the sheath entry site should be exposed to allow control. Proximally, this often requires dissection for two to three centimeters (2-3 cm) underneath the inguinal ligament as an assistant uses a narrow handheld retractor (e.g., short Wylie renal vein retractor) to lift the inguinal ligament off of the femoral sheath. During this maneuver, the surgeon preferably considers the circumflex iliac veins, which course over the top of the distal external iliac and proximal common femoral artery. Exposure distal to the sheath entry site preferably includes identification and control of both the superficial and profunda femoris arteries.

Once proximal and distal exposure and control have been accomplished, the sheath may be removed. The resulting arteriotomy should be closely examined and closed. Restoration of flow through the arterial segment is preferably confirmed using manual palpation for pulses and use of continuous wave Doppler of both the artery and more distal extremity. Closure of the femoral artery exposure is preferably accomplished in layers using absorbable suture in the soft tissues and skin.

REBOA can be considered in the following five steps, each with specific procedural considerations: 1. Arterial access, 2. Balloon selection and positioning, 3. Balloon inflation, 4. Balloon deflation, and 5. Sheath removal. REBOA procedures may be conducted under fluoroscopy or other suitable imaging modality.

There is a need for a device that permits medical practitioners to conduct REBOA procedures without the conventional necessity of using fluoroscopy or other imaging modality together with the suitability of using the device and techniques for field applications outside the hospital or in hospital emergency room settings. In trauma situations where a patient is undergoing severe central torso hemorrhaging, particularly when not in a hospital setting, such as on a battlefield or on a public street or highway, imaging capability is simply not available to emergency responders or field medical practitioners. In such situations, it is preferred to temporarily occlude a central torso hemorrhage so that the patient may be stabilized in the field and transported to a hospital or other facility in which repair of the traumatic injury may be conducted.

Injuries in modern warfare are often caused by explosion and related high-velocity penetrating shrapnel leading to non-compressible bleeding. Non-compressible bleeding accounts for approximately eighty-five percent (85%) of preventable deaths on the battlefield, eighty percent (80%) of which include acute hemorrhage within the abdomen/torso. Abdominal hemorrhage involves injury to the spleen, liver, or retroperitoneal vasculature, and is typically non-compressible, meaning that it cannot be treated by external compression or the application of tourniquets or topical dressings.

Emergency surgical intervention is currently the only available method for treating non-compressible abdominal hemorrhage. Battlefield or other major trauma generally occurs in an austere, resource constrained environment, often with extended evacuation time due to persisting tactical threats or environmental constraints. Transport time to reach a hospital where surgery can take place varies, but is estimated to average one hour (1 hr). The majority of preventable deaths due to abdominal hemorrhage is nearly fifty percent (50%) and can be attributed to delays in hemorrhage control during transportation, highlighting the need for rapid, far-forward hemorrhage treatments.

Systems, methods and compositions for an occlusion balloon catheter system comprising: a first catheter member having a first and second lumens extending along a longitudinal axis thereof that forms a proximal section of the catheter system, a second catheter member having a third lumen forming a distal section of the catheter system and coupled to a distal end of the first catheter member, an inflatable balloon coupled at its proximal end to a distal end of the first catheter member and at its distal end to a proximal end of the second catheter member, a first lumen of the first catheter member terminating within the inflatable balloon to communicate an inflation fluid to an area within the inflatable balloon and a second lumen of the first catheter member being in fluid flow communication with the third lumen of the second catheter member; an atraumatic guiding tip coupled to a distal end of the third lumen of the second catheter member; and a third catheter member having at least one lumen passing longitudinally therethrough, the third catheter member being disposed within each of the second lumen of the first catheter member and the third lumen of the second catheter member and passing therethrough.

Preferred embodiments of the present invention have been actively conceptualized, modeled, iterated and working prototypes produced of multiple REBOA related devices. The concepts are responses to the following lists of clinical needs, including (1) Pushing back the ischemic injury envelope, (2) Reperfusion mitigation/prevention, (3) Ischemia mitigation/prevention, (4) Hypertension mitigation/prevention, (5) Traumatic brain injury ("TBI") mitigation/prevention, (6) Pre-hospital use, (7) Rapid deployment, (8) Field specific packaging, (9) Easier to use, and (10) Lower profile.

Preferred embodiments of the present invention may also include:

Infusion Catheter

The infusion catheter or occlusion catheter system is a preferably multi-purpose, low profile, such as approximately five French (5 Fr) catheter, although the preferred system is not limited to catheters having this size. The preferred systems may be used independently or in conjunction with a REBOA catheter from the contralateral leg to administer fluids (i.e. reperfusion mitigation/ischemia prevention) or gas/fluid angiography below the REBOA occlusion balloon. The combination of the P-tip and hybrid shaft design preferably allow for proper placement in large vessels without needing to be inserted over a guidewire. The infusion catheter of the preferred embodiments may be compatible with power injection.

Smart REBOA

Smart REBOA is a REBOA accessory that can preferably be connected to and used with any REBOA catheter. Smart REBOA preferably controls the occlusion balloon inflation volume and inflation/deflation rate, using the patient's own vital signs as feedback. A validated algorithm is capable of using feedback from a variety of vital signs (i.e. heart rate, respiration rate, pulse oxygenation, blood pressure, etc.) to modulate the inflation volume of the balloon for an optimized REBOA procedure.

Decision Support REBOA (DS REBOA)

DS REBOA builds upon the preferred Smart REBOA concept. DS REBOA preferably combines the real time monitoring and feedback of the Smart REBOA device with a historical and constantly updated database of known REBOA cases and outcomes to provide forward looking possible diagnoses and other decision support information (collectively called 'prognostics') through sophisticated statistical means. The DS REBOA also preferably provides a patient specific, real time step through clinical practice guide and other decision support mechanisms to assist the clinician.

Power Injection Capable REBOA (PIC REBOA)

PIC REBOA is preferably a REBOA Catheter that is approximately seven French (7 Fr) compatible and offers the same or similar features as the ER-REBOA Catheter (balloon occlusion, built-in arterial line, guidewire and fluoroscopy-free), but preferably adds the ability to perform power injections. The PIC REBOA is not limited to being seven French (7 Fr) compatible.

REBOA With Above & Below Balloon Lumens (ABBL REBOA)

ABBL REBOA is a REBOA Catheter that preferably offers the same or similar features as the ER-REBOA Catheter, but contains an additional lumen below the balloon for fluid/gas injections/sampling. ABBL REBOA is preferably compatible with power injectors for either above or below the balloon angiography.

REBOA With a Partial Occlusion Balloon (POB REBOA)

POB REBOA is a REBOA Catheter that preferably provides the clinician the ability to selectively control the degree of occlusion. Balloon design preferably permits minimal occlusion, such as ten percent (10%), up to total or near total occlusion, such as one hundred percent (100%).

REBOA With Large Bore Lumen for High Flow Rate Infusions (LBL REBOA)

LBL REBOA is a REBOA Catheter that preferably includes the same or similar features as the ER-REBOA Catheter (balloon occlusion, built-in arterial line, guidewire and fluoroscopy-free), but has a larger diameter central lumen that provides the ability to perform high flow rate infusions (i.e. selective aortic arch perfusion (SAAP)).

ECMO/Cryogenic/CRRT Adjuncts

Extra Corporeal Membrane Oxygenation ("ECMO") continues to become more clinically widespread. ECMO is preferably used in cases where the patient's lungs have been damaged or temporarily compromised, by bypassing the patient's lungs through the use of catheters to shunt the blood away from the damaged organs and through an ECMO device instead. Recent advances have reduced the size, weight and cost of ECMO, while improving its efficacy. Combining the REBOA technology with various ECMO catheters to provide a "one stop" solution for patients with lung or other major organ compromise in the setting of hemorrhage may become a clinically preferred method. Similar combinations with existing and proposed cryogenic devices and Continuous Renal Replacement Therapy (CRRT) systems also are contemplated.

REBOA With Anti-Hypertension Feature (A-HYPER REBOA)

A-HYPER REBOA is a REBOA accessory that uses the patient's own supra-occlusion blood pressure to control the inflation/deflation of the REBOA balloon is contemplated. Should the patient's supra occlusion blood pressure rise dangerously high, potentially increasing the risk of hemorrhagic stroke, the system preferably automatically and temporarily deflates the REBOA balloon until the blood pressure drops to a safer level.

REBOA With Anti-Hypotension Feature (A-HYPO REBOA)

A-HYPO REBOA is a REBOA accessory that uses the patient's own blood pressure to control balloon deflation during the removal of the REBOA balloon is contemplated. If the patient's blood pressure should drop dangerously low during the deflation of the REBOA balloon, the system may automatically re-inflate the balloon to restore adequate pressure to the vital organs. The system will then preferably begin a pre-programmed cycle of deflation/repeat inflations until the patient can be weaned completely off occlusion.

Inflation Safety Device (ISD)

The ISD is a REBOA accessory that can preferably be used with the ER-REBOA Catheter to decrease the risk of over-inflating the balloon during fluoroscopy-free balloon inflation (i.e. field use). The ISD is preferably connected in line between the ER-REBOA Catheter and the inflation syringe. The user advances the syringe plunger, pausing occasionally to read the pressure gauge. When the pressure gauge needle comes to rest in the 'blue zone' or a preferred marked zone of the pressure gauge, proper occlusion has generally been achieved.

Infection Control Sleeve (ICS)

The infection control sleeve ("ICS") is a REBOA accessory that is preferably pre-loaded on the ER-REBOA Catheter to minimize the risk of infection when the device is deployed in austere environments. The ER-REBOA Catheter with the ICS preferably remains compatible with seven French 7 Fr components and has the same or similar features (balloon occlusion, built-in arterial line, guidewire and fluoroscopy-free) to other preferred REBOA systems and catheters.

Ruggedized, Low Volume (cube) Packaging (REBOA w/ LV PKG)

REBOA w/ LV PKG is a modified ER-REBOA Catheter and redesigned, ruggedized, low volume package (approximately twenty-five percent (25%) of the current ER-REBOA package volume) specific configured for field use. The ER-REBOA Catheter preferably remains compatible with seven French (7 Fr) components and has the same or similar features (balloon occlusion, built-in arterial line, guidewire and fluoroscopy-free) to other preferred REBOA systems.

Zone 3 REBOA (Z3 REBOA)

The Z3 REBOA is a REBOA Catheter preferably designed for Zone 3 placement relative to the aorta. The Z3 REBOA is preferably six French (6 Fr) compatible that has a shorter shaft length and an optimized balloon for generally less cumbersome Zone 3 placements.

Ultra-Low Profile REBOA (ULP REBOA)

The ULP REBOA is a preferred REBOA system that is compatible with six French or less (≤6 Fr) components. The ULP REBOA is preferably designed and configured for faster placement and improved ease-of-use. The balloon is filled with carbon dioxide ($CO_2$), preferably using a pressure regulated system that preferably inflates the balloon to a set pressure, regardless of the diameter of the aorta. The use of the carbon dioxide ($CO_2$) also enables the catheter shaft to be ultra-low profile, such as less than or equal to six French (≤6 Fr) compatible. An electronic, catheter-based pressure sensor typically requires no priming/flushing, so arterial line measurements can preferably be taken as soon as the device is inserted.

REBOA Gas Balloon Inflator (GBI)

The GBI is a REBOA accessory that is preferably used with the ER-REBOA Catheter to provide rapid balloon inflation/deflation. The GBI preferably fills the balloon with carbon dioxide ($CO_2$) gas to a set pressure, regardless of the vessel diameter, preferably making pre-hospital balloon inflation less technique dependent.

Guidewire Compatible REBOA (GWC REBOA)

The GWC REBOA is a preferred REBOA Catheter that can be used with a guidewire but doesn't require one and is preferably compatible with seven French (7 Fr) components. The preferred GWC REBOA allows the user to leave behind a guidewire when finished with REBOA for additional procedures. The GWC REBOA Catheter preferably, but not necessarily, remains seven French (7 Fr) compatible and has the same or similar features (balloon occlusion, built-in arterial line, guidewire and fluoroscopy-free) to other preferred REBOA systems.

When a fluid is used as the pressure source to activate the occlusion member, such as to fill an occlusion balloon, that fluid may be a liquid, including water, saline, contrast medium or any combination thereof, or may be a gas, including carbon dioxide, helium, air or oxygen.

It would be desirable to develop a system that intermittently and automatically releases an occlusion by releasing apposition of an occlusive member against the vascular wall and allowing perfusion past the occlusion member in response to a physiological parameter, then reestablishing occlusion in response to the same physiological parameter.

The methods, systems, and apparatus are set forth in part in the description which follows or can be learned by practice of the methods, apparatus, and systems. The advantages of the methods, apparatus, and systems will be realized and attained by means of the elements and combinations particularly pointed out in the appended claims and the below description. It is to be understood that both the foregoing general description and the following detailed description are exemplary and explanatory only and are not restrictive of the methods, apparatus, and systems, as claimed or described.

BRIEF DESCRIPTION OF SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
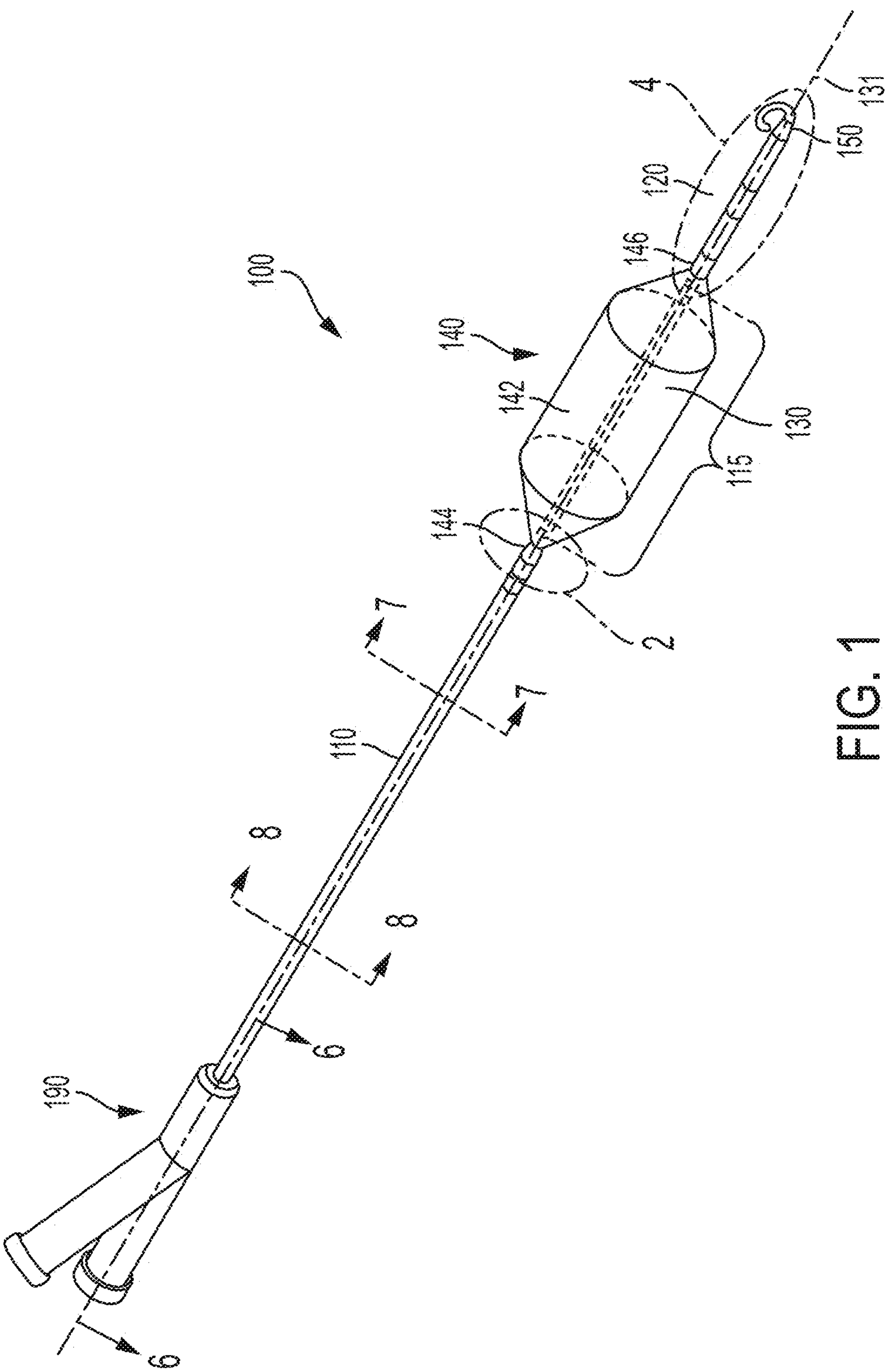
FIG. 1 is a top perspective view of a first preferred embodiment of an occlusion catheter system in accordance with the present invention.
Figure 2:
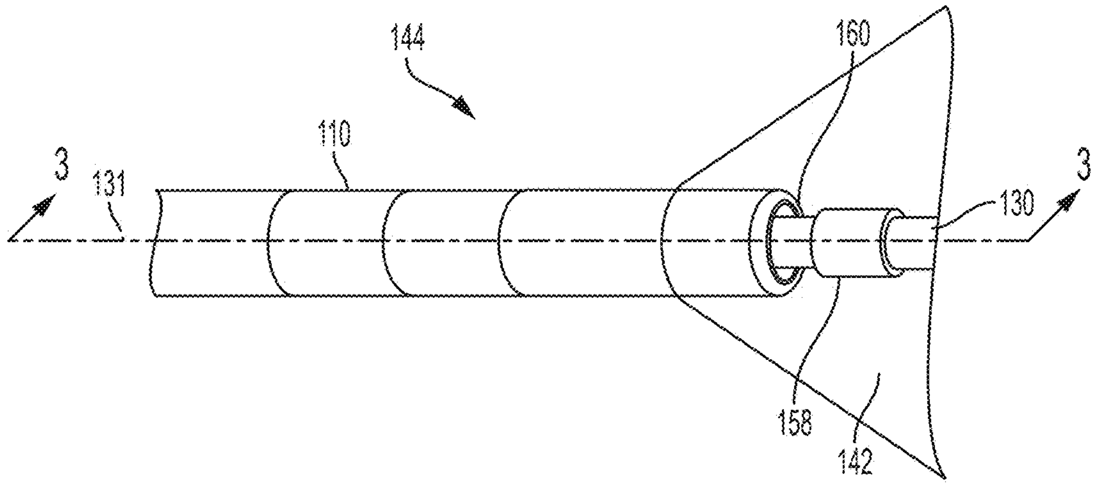
FIG. 2 is an enlarged perspective view of the occlusion catheter system of FIG. 1 taken from within circle 2 of FIG. 1 with a transparent occlusion balloon.
Figure 3:
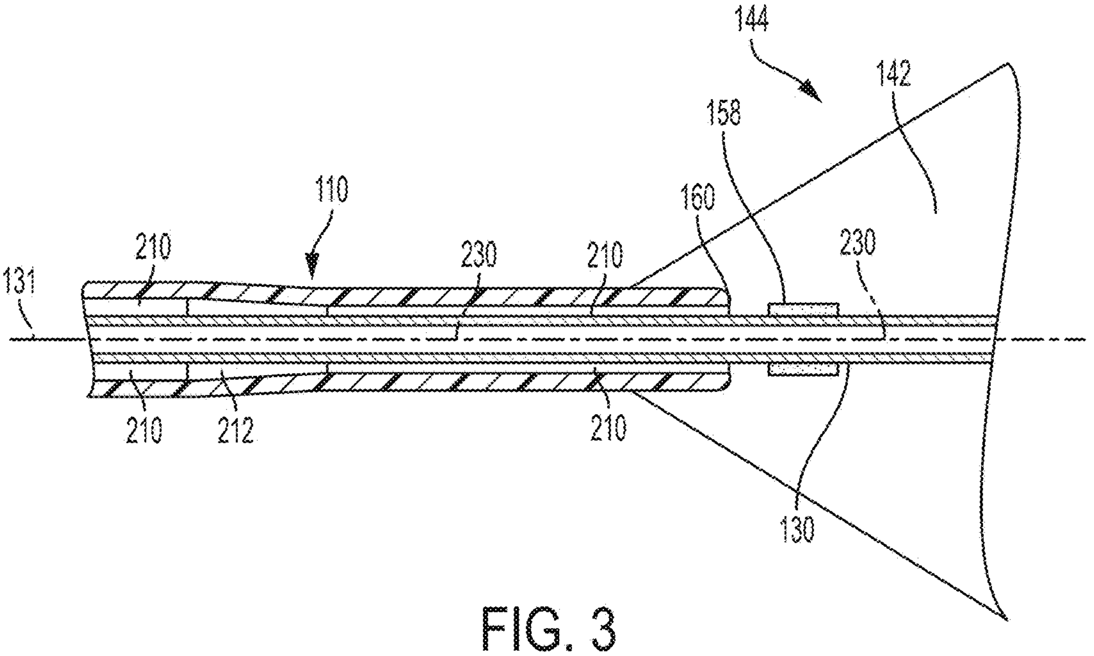
FIG. 3 is a cross-sectional view the occlusion catheter system of FIG. 1, taken along line 2-2 of FIG. 2.

The foregoing and other features and advantages of the invention will become more apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Certain terminology is used in the following description for convenience only and is not limiting. Unless specifically set forth herein, the terms “a”, “an” and “the” are not limited to one element but instead should be read as meaning “at least one”. The words “right”, “left”, “lower” and “upper” designate directions in the drawings to which reference is made. The words “inwardly” or “distally” and “outwardly” or “proximally” refer to directions toward and away from, respectively, the patient’s body, or the geometric center of the preferred occlusion balloon catheter and related parts thereof. The words, “anterior”, “posterior”, “superior,” “inferior”, “lateral” and related words and/or phrases designate preferred positions, directions and/or orientations in the human body to which reference is made and are not meant to be limiting. The terminology includes the above-listed words, derivatives thereof and words of similar import.

It should also be understood that the terms “about,” “approximately,” “generally,” “substantially” and like terms, used herein when referring to a dimension or characteristic of a component of the invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

Certain terminology is used in the following description for convenience only and is not limiting. The words “lower,” “bottom,” “upper” and “top” designate directions in the drawings to which reference is made. The words “inwardly,” “outwardly,” “upwardly” and “downwardly” refer to directions toward and away from, respectively, the geometric center of the vascular occlusion catheter system, and designated parts thereof, in accordance with the present disclosure. Unless specifically set forth herein, the terms “a,” “an” and “the” are not limited to one element, but instead should be read as meaning “at least one.” The terminology includes the words noted above, derivatives thereof and words of similar import.

It should also be understood that the terms “about,” “approximately,” “generally,” “substantially” and like terms, used herein when referring to a dimension or characteristic of a component of the invention, indicate that the described dimension/characteristic is not a strict boundary or parameter and does not exclude minor variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Vascular Occlusion Systems

Furthermore, while the invention is described as a balloon catheter occlusion system, it will be understood that the described variants of the preferred balloon catheter system may be used clinically for a variety of different therapeutic or diagnostic indications involving vascular interventions, including, for example and without limitation, arterial occlusion, angioplasty, stent delivery, atherectomy, drug delivery, imaging or the like. In accordance with an exemplary and preferred embodiment, the preferred balloon catheter system is well suited for use as an arterial occlusion balloon catheter, and in particular an aortic occlusion balloon catheter. Applications making advantageous use of embodiments of the invention may use any suitable access site for vascular intervention. For example, applications of the catheter system may involve access at the femoral artery, the brachial artery, the subclavian artery, or any other blood vessel suitable for use as an access site for catheterization, including venous vessels.

Moreover, it will be understood that while a balloon is referred to herein as an example of occlusion member, other types of occlusion members are contemplated as being expressly within the scope of the present invention. In addition to balloons, the occlusion members may include stents, coils, grafts, sheaths, cages, plugs, supported or unsupported membranes, or the like. The occlusion member, including the occlusion balloons, may be fabricated of biocompatible polymer or biocompatible metal, or combinations thereof, and may be woven or non-woven in structure. Biocompatible metals include, but are not limited to, stainless steel, titanium, nitinol, cobalt, vanadium, aluminum, nickel, tantalum, zirconium, chromium, silver, gold, silicon, magnesium, niobium, scandium, platinum, cobalt, palladium, manganese, molybdenum and alloys thereof, such as cobalt-chromium-molybdenum or zirconium-titanium-tantalum alloys. The metals and/or the polymers may be elastic, shape memory or superelastic. More recent advanced materials may also be used, including carbon fibers, carbon nanotubes or carbon composites, such as carbon/polyetheretherketone (PEEK). In the present application, when the term “balloon” is used it is intended to mean a fluid fillable member capable of expanding from a first smaller diameter to a second larger diameter under the influence of fluid introduced into the balloon. Unless otherwise stated, a balloon is not limited in size, shape, geometry, material or construction. When used in this application, the term “occlusion member” is intended to be inclusive of balloons and other structures, including stents, coils, grafts, sheaths, cages, plugs or supported or unsupported membranes.

In one aspect of the invention, a pressure relief apparatus for a balloon catheter is provided. The balloon catheter includes a shaft having a balloon attached to the distal end of the shaft, an inflation/deflation lumen for inflating and deflating the balloon and a pressure relief port. The pressure relief port may alternatively be formed through the wall of the inflation/deflation lumen, through the wall of the proximal hub, or may be part of the fluid pathway that couples to the proximal hub. A pressure relief member is secured either across or within the pressure relief port to form a fluid tight seal. The fluid tight seal is configured to open or fail (e.g. open, burst, rupture, tear or leak) at a predetermined pressure to release pressure from the inflation/deflation lumen through the pressure relief port. The predetermined pressure may be less than or equal to the rated burst pressure of the balloon.

In one variation, the pressure relief port comprises a first outwardly opening passage and a second passage in fluid communication with the first passage. The second passage extends inwardly from the first passage and opens into the inflation/deflation lumen. In this variation, the cross-sectional area of the first passage may be larger than the cross-sectional area of the second passage.

In one embodiment, a wall extends radially between an inside end of the first passage of the pressure relief port and an outside end of the second passage of the pressure relief port. The pressure relief member maybe disposed adjacent the wall and across the outside end of the second passage of the pressure relief port to block the pressure relief port and form a fluid tight seal. The pressure relief member may be a plastic film, a thin metallic film, a pop-off valve or other similar biased valve. The bias of the pressure relief member is less than or equal to a predetermined pressure known to protect the device from overpressure and burst and to protect the patent from injury.

In another aspect, a pressure relief apparatus for a balloon catheter having a balloon with a rated burst pressure includes a proximal hub adapted for connection to a proximal end portion of a balloon catheter shaft wherein a pressure relief port is formed in the proximal hub. In one embodiment, the proximal hub may comprise a plastic body that defines an inflation/deflation lumen and a may or may not include guide wire lumen or a working lumen.

The proximal hub may be formed from a substantially rigid material and includes a wall defining the inflation/deflation lumen for directing a fluid into and from an inflation/deflation lumen of the catheter shaft. In this alternative embodiment, the proximal hub includes a pressure relief port formed through the wall of the hub and a pressure relief member disposed across or in the pressure relief port, forming a fluid tight seal across the pressure relief port. The pressure relief member is configured to open or fail, (e.g. open, rupture, tear, burst or leak), at a predetermined pressure to release pressure from the inflation/deflation lumen through the pressure relief port.

In the case of an occlusion balloon, it is preferable that the balloon be of a compliant or partially compliant balloon material and typically formed relatively distensible plastic or polymer material. The balloons may also be constructed of substantially compliant or partially compliant polymeric, biocompatible materials, such as PBAX or other related polymers. The balloon may alternatively be constructed of a non-compliant material, which will typically expand less than about ten percent (10%), and more typically less than about five percent (5%), when pressurized from their rated operating pressure to the balloon's rated burst pressure.

Where an occlusion balloon is the occlusion member, the proximal and distal ends of the balloon may be attached to the catheter shaft using techniques known in the art, for example, with an adhesive such as a medical grade epoxy adhesive or may be reflowed to become an integral part of the catheter shaft wall.

In the following description, when reference is made to the terms "proximal" or "proximally" it is intended to mean a portion or component of the preferred vascular occlusion catheter system that is oriented away from the body into which the system is or is intended to be placed. Conversely, when reference is made to the terms "distal" or "distally" it is intended to mean a portion or component of the preferred balloon catheter system that is oriented toward the body into which the system is or is intended to be placed. Thus, for example, the guiding atraumatic tip described hereinafter is located at a distal end of the balloon catheter system, while the proximal hub is located at a proximal end of the balloon catheter system.

As shown in the accompanying figures, the vascular occlusion catheter system 100 generally includes a catheter assembly having a first catheter member 130 having a first lumen 230, a second catheter member 110 having a second lumen 210, a third catheter member 120 having a third lumen 220, an occlusion member 140, a proximal hub 190 and a guiding atraumatic tip 150. The first lumen 230 of the first catheter member 130 extends longitudinally through the first catheter member and is coupled at its proximal end to the proximal hub 190 and at its distal end to a proximal section of the third catheter member 120 and in communication with the third lumen 220 of the third catheter member. The second lumen 210 of the second catheter member 110 also extends longitudinally through the second catheter member 110, and terminates in a first port 160 distal to a proximal end of and within a space 142 at least partially bounded by the occlusion member 140, best seen in FIGS. 9 and 9A. Where the occlusion member 140 is a balloon, the second lumen 210 is in communication with the space 142 bounded by the balloon 140 and conveys inflation fluid to and from the balloon 140 from a source external to the balloon catheter system 100. The third catheter member 120 is coupled at a proximal end thereof to a distal end of the first catheter member 130 such that the third lumen 220 of the third catheter member 120 is in communication with the first lumen 230 of the first catheter member 130. As best seen in FIG. 1, the second catheter member 110 and the third catheter member 120 are positioned in longitudinal co-axial spaced apart relationship from one and other along a longitudinal axis 131 of the first catheter member 130 thereby defining an intermediate region 115 of the first catheter member 130 within the space 142 that is not covered by either the second catheter member 110 or the third catheter member 120.

When a balloon is the occlusion member 140, balloon 140 is attached, at its proximal end 144 to a distal end of the second catheter member 110 and at its distal end 146 to a proximal end of the third catheter member 120. Referring to FIGS. 2-5, a proximal radio opaque marker 158 may be affixed to the first catheter member 130 at or near the first port 160, which is near the attachment position of the inflatable balloon at the proximal end 144 of the balloon 140. A distal radio opaque marker 159 may be affixed to the first catheter member 130 near the attachment position on the distal end 146 of the balloon 140. The proximal and distal radio opaque markers 158, 159 may be implemented as bands made of a radio opaque material. In one example, the radio opaque material is a metal that is radio opaque such as stainless steel, or an alloy, such as a platinum iridium alloy. In another example, the proximal and distal radio opaque markers 158, 159 may be sections of the catheters that have been impregnated with radio opaque material such as for example stainless steel or a suitable alloy. In another example, the proximal and distal radio opaque markers 158, 159 may be implemented as bands or sections of plastic or a polymer such as PEBAX that has been mixed with barium sulfate. The implementation of the proximal and distal radio opaque markers 158, 159 on the catheter system would aid in visualization of the balloon position within the vasculature using fluoroscopy or x-ray.

When a balloon is used as the occlusion member 140, in operation, balloon 140 is inflated by introducing an inflation fluid, such as saline, from an external source, such as a syringe, coupled to the proximal hub 190, into and through the second lumen 210, out of the first port 160 and into the space 142 within the balloon 140. As is known in the art, the inflation fluid is introduced until the balloon 140 is inflated to a desired diameter or a desired fluid pressure of the inflation fluid is achieved, or both. Deflation of the balloon 140 is simply the reverse process of withdrawing the inflation fluid from the space 142 of the inflation balloon 140. In its deflated or collapsed state, the inflation balloon 140 will be positioned either within or adjacent to the intermediate region 115 of the first catheter member 130, thereby providing a lower profile to the entire balloon catheter system 100.

When a fluid is used as the pressure source to activate the occlusion member, such as to fill an occlusion balloon, that fluid may be a liquid, including water, saline, contrast medium or any combination thereof, or may be a gas, including carbon dioxide, helium, air or oxygen. Catheter balloons may be inflated with gas, rather than liquid, because the balloon can be inflated and deflated more quickly than a comparable volume of saline or other liquid inflation media. Although air is relatively easy to load into an inflation device, air is not an ideal inflation medium, because air does not rapidly dissolve in blood. In the event that the balloon bursts or leaks, bubbles could be formed in the arterial blood, impeding blood flow. In addition, as nitrogen is a chief component of air, nitrogen has thrombogenic properties that may present clinical risks in the event the balloon bursts. Accordingly, it is desirable to use a gas other than air and to prevent air contamination of the gas used. A preferable gas used for balloon inflation is either carbon dioxide or helium.

As will be described in more detail hereinafter, with exemplary reference to FIGS. 19-22, the present invention also includes alternative embodiments of occlusion control systems that regulate the position of the occlusion member 140 and the apposition of the occlusion member 140 against a vascular wall surface. It is understood that when the occlusion member 140 is at least partially in non-apposition with the vascular wall surface, that fluid flow or perfusion pas the occlusion member may or will occur. This fluid flow or perfusion may be of circulatory blood, or may be of fluids introduced through the preferred vascular occlusion catheter system, or through another fluid introduction system, such as a catheter.

Figure 4:
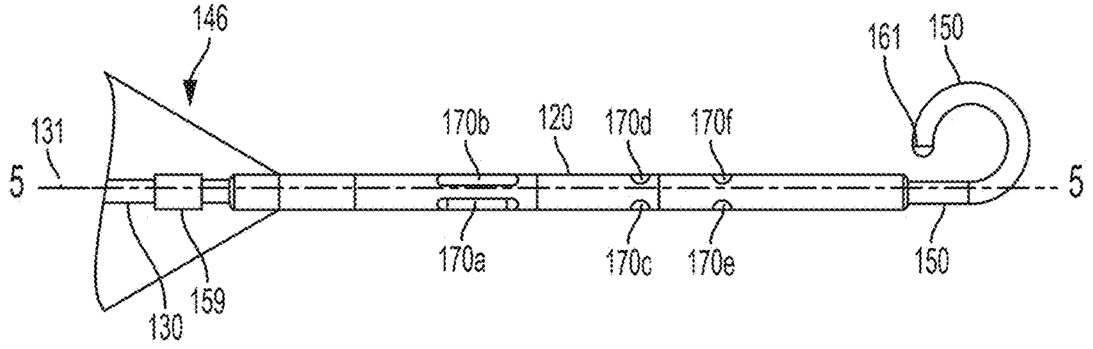
FIG. 4 is an enlarged perspective view of the occlusion catheter system of FIG. 1, taken from within circle 4 of FIG. 1 with a transparent occlusion balloon.
Figure 5:
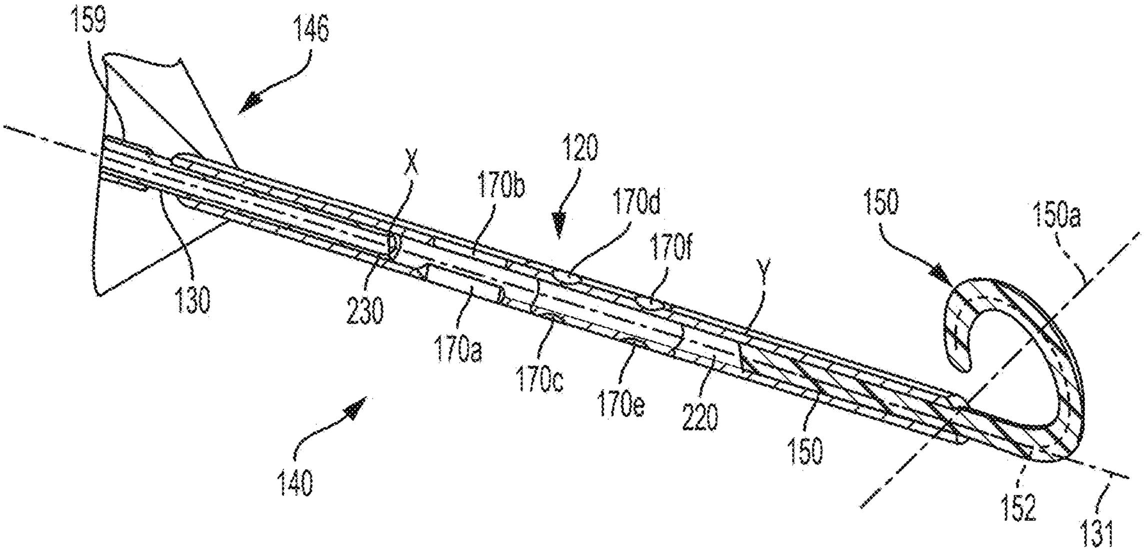
FIG. 5 is a cross-sectional view the occlusion catheter system of FIG. 1, taken along line 5-5 of FIG. 2 directly into the page of FIG. 2.

The third catheter member 120 is depicted more particularly in FIGS. 4-5. The third catheter member 120 is coupled at its proximal end concentrically about a distal end of the first catheter member 130. A plurality of side ports 170 pass through a side wall of the third catheter member 120 and provides fluid communication between the third lumen 220 and external environments proximate the external surface of the third catheter member 130, such as the inside of the patient's major vessel when inserted into the patient. The distal end of the first catheter member 130 is preferably positioned within the third lumen 220 and does not occlude the plurality of side ports 170, but terminates proximal to the plurality of side ports 170 such that fluid may be freely communicated between the first lumen 230, the third lumen 220 and the plurality of side ports 170 to either introduce fluid or withdraw fluid through the plurality of side ports 170. The plurality of side ports 170 may also be utilized for power injection of a contrast medium into the major vessel of the patient distally relative to the occlusion member 140, as will be described in further detail herein. It will also be understood by those skilled in the art that maintaining fluid communication between the first lumen 230, the second lumen 220 and the plurality of side ports 170 also permits introduction of tethered sensors, such as flow sensing wires, pressure sensing wires, ischemia sensors or the like to the distal end of the balloon catheter system 100.

Finally, a guiding atraumatic tip 150 is coupled to a distal end section of the third catheter member 120. The guiding atraumatic tip 150 may be made of an elastic, shape memory and/or superelastic material, such as a metal or polymer. A reinforcing member 152 (depicted in phantom) may optionally be included either within the guiding atraumatic tip 150 or wound about an external surface of the guiding atraumatic tip 150 to offer additional reinforcement to the tip 150. A proximal end of the guiding atraumatic tip 150 is coupled to a distal end of the third lumen 220 of the third catheter member 120 and a distal end of the guiding atraumatic tip 150 projects distally from the third catheter member 120 and preferably has a generally circular profile when viewed from the side in a relaxed configuration. The atraumatic tip 150 preferably curves proximally from the longitudinal axis 131 upwardly and then back toward the central longitudinal axis 131 of the balloon catheter system 100, but leaves an unconnected end 161 of the distal end of the guiding atraumatic tip 150 as it returns to a position proximate the longitudinal axis 131. The atraumatic tip 150 is designed and configured to permit the tip 150 to assume a linear or delivery configuration co-axial with the central longitudinal axis 131 of the balloon catheter system 100 for delivery and introduction into the patient's vessel through a catheter. Once the atraumatic tip 150 is introduced into the vessel and emerges from the introduction catheter, the atraumatic tip 150 preferably returns to the relaxed configuration to inhibit introduction of the catheter system 100 into smaller vessels as it moves into the patient.

In the first embodiment of the preferred balloon catheter system 100 illustrated in FIGS. 1-8, the balloon catheter system 100, when the inflatable balloon 140 is in an uninflated condition, is of sufficiently small cross-segmental dimension to pass through a 6 to 8 French (2-2.67 mm) percutaneous sheath, such as, for example 7 French (2.33 mm). Thus, the balloon catheter system 100 has a greatest outer diameter, when the inflatable balloon 140 is uninflated, of less than 2-2.67 mm. It will be understood by those skilled in the art that the balloon catheter system 100 is not limited to a dimension sufficient to pass through a 2-2.67 mm (6 to 8 French) percutaneous sheath, but that such lower profile or smaller is generally considered desirable to enable passage of a balloon catheter system 100 through tortuous vasculature and to a desired position within the body for purposes of arterial occlusion. The balloon catheter system 100 is, therefore, not intended to be limited to this dimensional size, but may be made of smaller or larger dimension as desired or needed.

In one embodiment of the invention, the first catheter member 130 is formed of stainless steel metal and is radio opaque, in accordance with another embodiment of the invention, it is constructed of nitinol and in accordance with still another embodiment of the invention it is formed of biocompatible polymers. The first catheter member 130 lends columnar strength to the balloon catheter system 100 and provides a functional backbone for carrying the second catheter member 110, the third catheter member 120 and the inflatable balloon.

Figure 7:
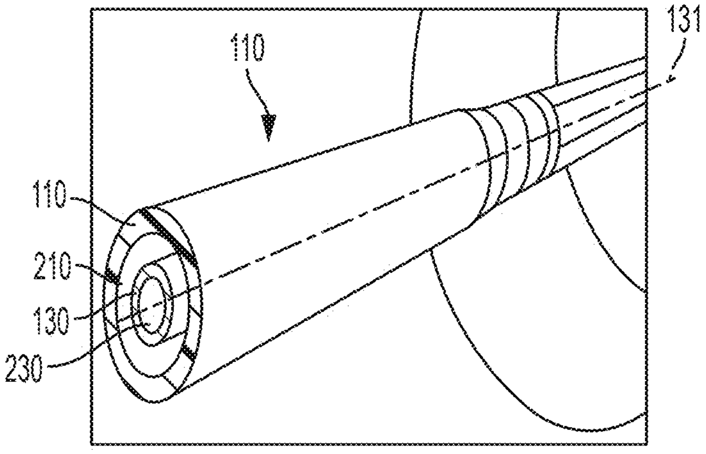
FIG. 7 is a combination partial cross-sectional view of the occlusion catheter system taken along line 7-7 of FIG. 1 and a magnified top perspective view of the occlusion catheter system near a proximal end of the occlusion balloon of the occlusion catheter system of FIG. 1.
Figure 8:
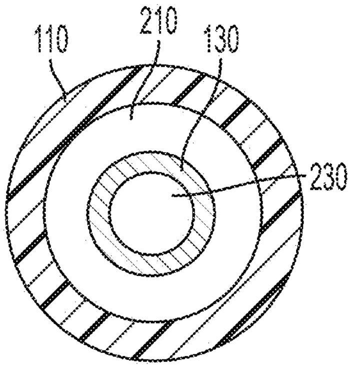
FIG. 8 is a cross-sectional view of the occlusion catheter system of FIG. 1, taken along line 8-8 of FIG. 1.

The outer diameter of the first catheter member 130 is smaller than the inner diameter of the second lumen 210 of the second catheter member 110, thereby forming an annular space 212 between the outer surface of the first catheter member 130 and the inner surface of the second catheter member 110, as best shown in FIG. 7.

In one embodiment of the invention, the distal end of the second catheter member 110 may have a tapering or narrowing diameter of the outside surface and/or the second lumen 210 diameter. Preferably, there is a minimal amount of narrowing on the second catheter member 110 and the proximal lumen 210 to allow the annular space 212 to remain sufficiently large down the length of the second catheter member 110 to permit adequate flow of the inflation fluid through the annular space 212.

Turning now to FIGS. 4-5, the distal portion of the balloon catheter system 100 is illustrated. The first lumen 230 of the first catheter member 130 may be used as a pressure monitoring line, such as by using a fluid column therein to sense pressures through the plurality of side ports 170. The first lumen 230 may alternatively be used to introduce or withdraw fluids, such as drugs, contrast media or blood through the plurality of side ports 170. Referring to FIG. 5, the outer surface of the first catheter member 130 is coupled to at least a portion of the inner surface of the distal lumen 220, such that there is no annular space between the outer surface of the first catheter member 130 and the inner surface of the second lumen 220. In one embodiment, the portion of the inner surface of the distal lumen 220 may be the length of the second lumen 220. Referring now to FIG. 4, the third catheter member 120 or the proximal shaft of the atraumatic tip 150 may include a plurality of segments of distally decreasing durometer polymer to provide a step-down transition to the guiding atraumatic tip 150. The number of step down durometer segments may be between one (1) and six (6) and may step down in decreasing fashion by regular or irregular increments, such, for example 75 D, 63 D, 55 D, 40 D, etc. Alternatively, the third catheter member 120 may be made of a single durometer polymer, but having distally tapering wall thicknesses to impart a flexibility gradient to the third catheter member 120. The plurality of segments of decreasing durometer plastic may be abutted and be bonded together or may be manufactured from a single extrusion including decreasing durometer hardness.

Referring now to FIG. 5, the guiding atraumatic tip 150 is shown in its unstrained and undeformed state as it would assume when in the body. The guiding atraumatic tip 150 is used to minimize trauma to or perforation of the vasculature as the balloon catheter system 100 is advanced through the patient's tortuous anatomy, and to prevent departure from an intended vessel path, such as diversion into an undesired branch vessel. The size, shape and material of the distal section of the tip 150 are such that it will not pass into collateral vessels during delivery. The guiding atraumatic tip 150 has a constrained state when passing through an introducer sheath in which the distal section of the tip 150 is substantially linear and co-axial with the longitudinal axis 131 of the balloon catheter system 100, and a relaxed state, as depicted, which is assumed upon exiting the introducer sheath and entering a blood vessel. In one embodiment, the guiding atraumatic tip 150 may be formed of an elastomeric, shape memory or superelastic material, including metals and polymer. In another embodiment, the guiding atraumatic tip 150 may have a reinforcing elastic, shape memory or superelastic core 152 which aids in transition between the unstressed state and the stressed state of the guiding atraumatic tip 150. In accordance with an exemplary embodiment of the tip 150, the outer diameter of the guiding atraumatic tip 150 (in the relaxed state) may be between 1-7 mm, preferably between 2-6 mm and most preferably between 4-6 mm.

Figure 6:
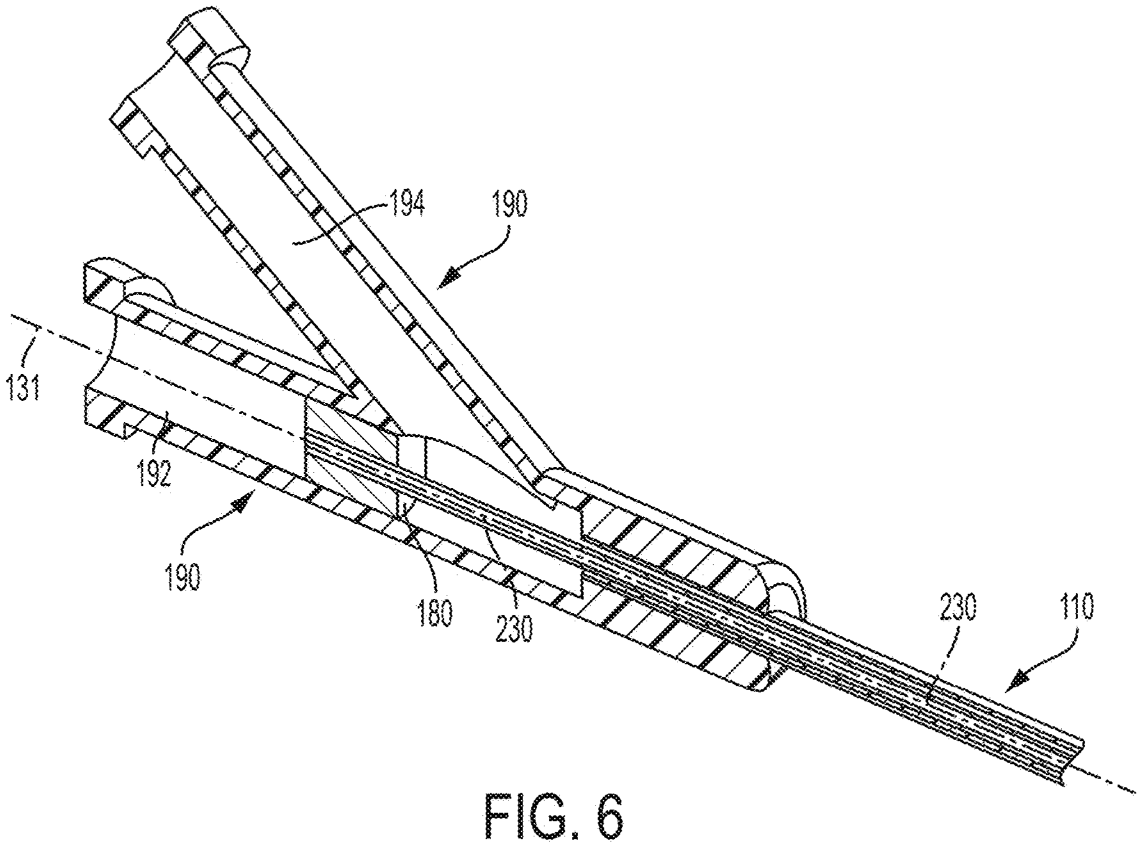
FIG. 6 is a cross-sectional view of the occlusion catheter system of FIG. 1, taken along line 6-6 of FIG. 1.

Turning now to FIG. 6, the proximal portion of the balloon catheter system 100 is illustrated. The second catheter member 110 is coupled to the proximal hub 190 and the distal end of the first catheter member 130 may be operably coupled to the proximal hub 190 at a proximal bonding site using an adhesive 180 to bond an inner wall surface of the proximal hub 190 to an outer wall surface of the first catheter member 130. As illustrated, the proximal hub 190 has two fluid pathways 192 and 194. A first fluid pathway 192 communicates with the first lumen 230 of the first catheter member and a second fluid pathway 194 communicates with the second lumen 210 of the second catheter member 120. It will be understood that the proximal hub 190 may be configured to have more than two fluid pathways, with each fluid pathway communicating with a different lumen in the balloon catheter system 100. The first fluid pathway 192 of the proximal hub 190 may be connected to an external pressure sensor, which would transduce pressure from a fluid column within the first lumen 230 and through the plurality of side port 170 (FIG. 5).

Referring to FIGS. 1-5, in the first preferred embodiment, the balloon catheter system or occlusion catheter system 100 also includes the plurality of side ports 170 positioned between the occlusion member 140 and the atraumatic tip 150 in the third catheter member 120, the proximal shaft of the atraumatic tip 150 and/or the first catheter member 130. The plurality of side ports 170 preferably facilitates power injection of a contrast medium into the patient's major vessel distally relative to the occlusion member 140 during use. Such power injection may be utilized for procedures such as angiography or arteriography. In the first preferred embodiment, the plurality of side ports 170 include a first side port 170*a*, a second side port 170*b*, a third side port 170*c*, a fourth side port 170*d*, a fifth side port 170*e* and a sixth side port 170*f*. The plurality of side ports 170 is not limited to including six (6) side ports 170*a*, 170*b*, 170*c*, 170*d*, 170*e*, 170*f* and the occlusion catheter system 100 may include more or less side ports 170*a*, 170*b*, 170*c*, 170*d*, 170*e*, 170*f* and the plurality of side ports 170 may be sized and configured in nearly any manner desired by the designer and/or medical technician for pressure sensing, power injection or other related procedures utilizing the plurality of side ports 170.

Turning now to FIGS. 9 and 9A-9D, an alternative or second preferred embodiment of the balloon catheter system 300 is illustrated. The balloon catheter system 300 includes generally a catheter assembly including a first catheter member 310 having at least two lumens 210, 330 passing longitudinally through the first catheter member 310, a second catheter member 320 having a single lumen 230 passing longitudinally through the second catheter member 320 and an inflatable balloon 140. The first catheter member 310 is coupled at its proximal end to a proximal hub 190 (not shown) and at a distal end thereof to a proximal end of the inflatable balloon 140. The second catheter member 320 is coupled at its distal end to a proximal end of the first catheter member 310 such that one of the first lumen 210 or the second lumen 330 is in fluid flow communication with the second catheter member 320. The other of the first lumen 210 or the second lumen 230 terminates at the distal end of the first catheter member 310. For purposes of illustration only and for clarity in the following description, it will be assumed that second lumen 330 terminates at the distal end of the first catheter member 310 and has a distal port opening 160, it will also be assumed that the first lumen 210 is in fluid flow communication with the second catheter member 320. As with the first embodiment of the balloon catheter system 100 described above, the second embodiment of the balloon catheter system 300, when the inflation balloon 140 is in an uninflated condition, is of a sufficiently small cross-sectional diameter to pass through a 6-8 French (2-2.67 mm) percutaneous sheath, such as, for example, 7 French (2.33 mm). Thus, the balloon catheter system 300 has a greatest outer diameter, when the inflatable balloon 140 is uninflated, that is less than 2-2.67 mm. It will be understood by those skilled in the art that the balloon catheter system 100 is not limited to a dimension sufficient to pass through a 2-2.67 mm (6 to 8 French) percutaneous sheath, but that such lower profile or smaller is generally considered desirable to enable passage of a balloon catheter system 300 through tortuous vasculature and to a desired position within the body for purposes of arterial occlusion. The balloon catheter system 300 is, therefore, not intended to be limited to this dimensional size, but may be made of smaller or larger dimension as desired or needed.

Figure 9:
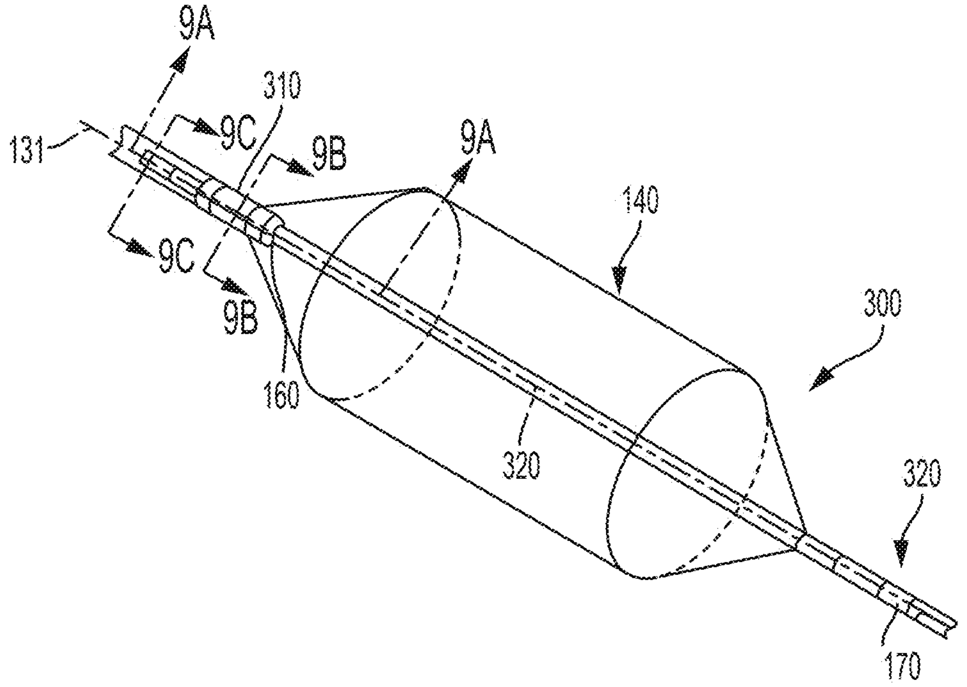
FIG. 9 is a magnified top perspective view of a portion of a second preferred embodiment of the occlusion catheter system proximate a occlusion balloon of the second preferred occlusion catheter system of the present invention.
Figure 9A:
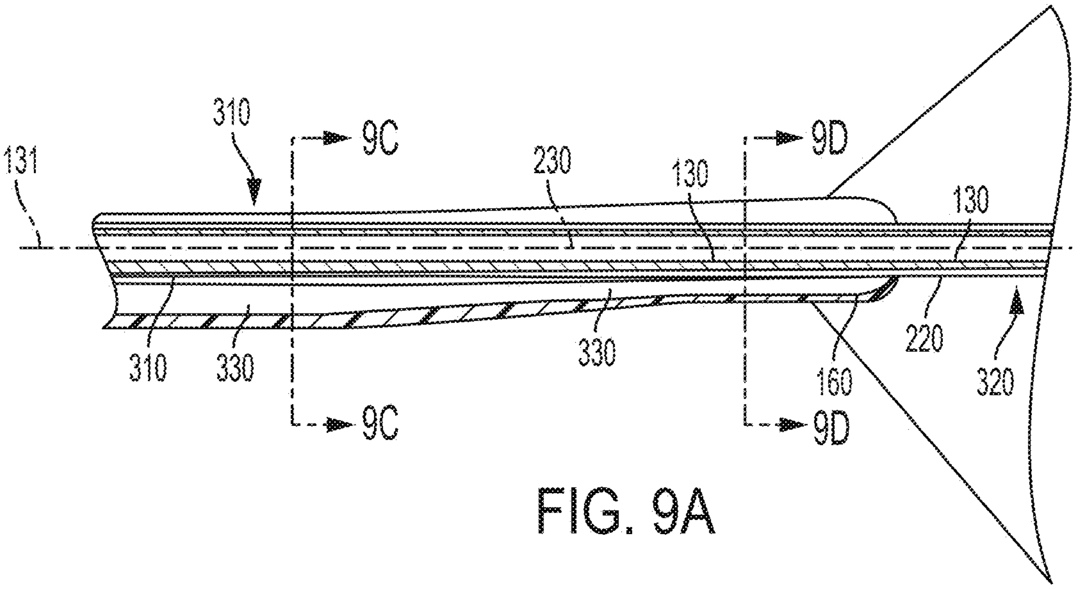
FIG. 9A is a cross-sectional view of the occlusion catheter system of FIG. 9, taken along line 9A-9A of FIG. 9.
Figure 9B:
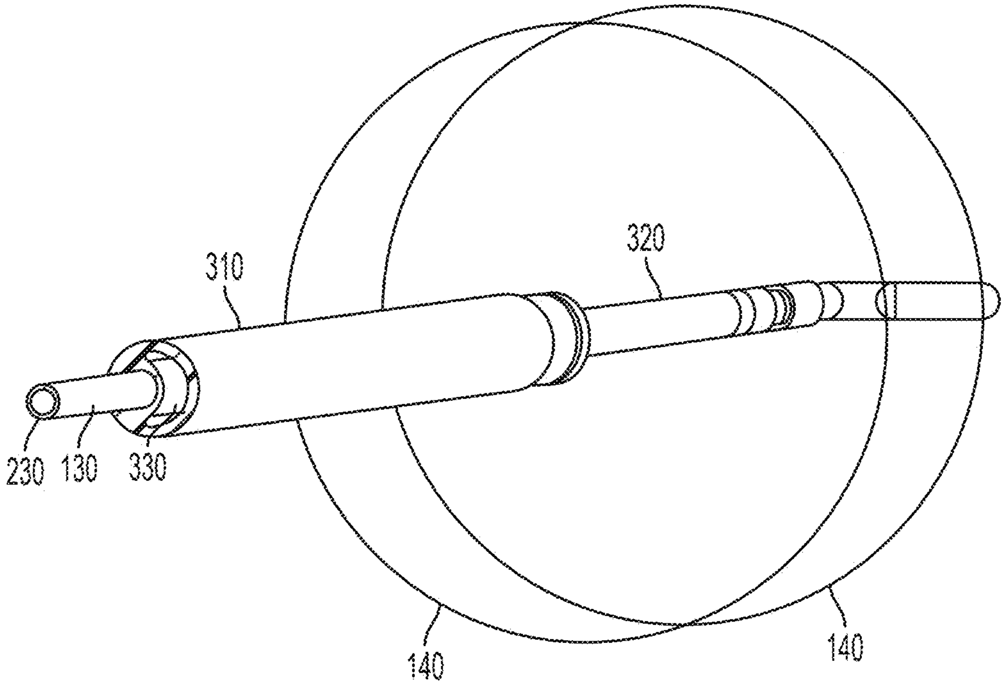
FIG. 9B a combination partial cross-sectional view of the occlusion catheter system taken along line 9B-9B of FIG. 9 and a magnified top perspective view of the occlusion catheter system near a proximal end of the occlusion balloon of the occlusion catheter system of FIG. 9.

Referring now to FIG. 9A, the first catheter member 310 includes first lumen 330 and a second lumen 210. The second catheter member 320 includes a first lumen 220. The first catheter member 310 terminates at its distal end within the space defined under the balloon 140, where it is both coupled to the second catheter member 320 and terminates with an open port 160 in fluid communication with lumen 330, permitting fluid to be delivered to and from the balloon 140 for inflation and/or deflation. In accordance with an alternative embodiment, the distal end of the first catheter member 310 may, optionally, be tapered, such as by narrowing the wall thickness of the catheter member 310 or by crimping the first catheter member 310 to a smaller diameter, thereby compressing and reducing the open area of the first lumen 330 and the second lumen 210. If the first catheter member 310 is crimped to a tapered diameter, it is preferable that the extent of the crimping does not compress the open area of the first lumen 330 and the second lumen 210 in a manner that significantly reduces fluid flow there through of fluid flow pressures therein, particularly with the second lumen 330 when it is used for the inflation fluid for the inflation balloon 140.

Figure 9C:
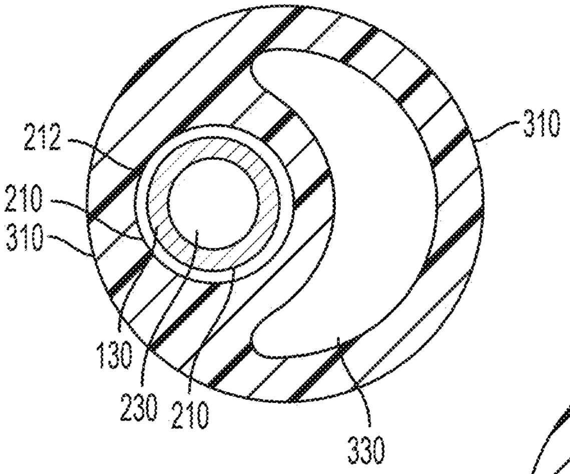
FIG. 9C is a cross-sectional view of the occlusion catheter system of FIG. 9, taken along line 9C-9C of FIG. 9.

The third catheter member 130 is positioned within one of the first lumen 210 or the second lumen 330 of the first catheter member 310. As depicted in the figures, this arrangement is illustrated with the third catheter member 130 being positioned within the first lumen 210 of the first catheter member 310 and also within the first lumen 220 of the second catheter member 320. The outer diameter of the third catheter member 130 is less than the inner diameter of the first lumen 210 of the first catheter member 310 as well as smaller than the inner diameter of the first lumen 210 of the second catheter member 320, such that an annular space 212 is formed therebetween as depicted in FIG. 9C. In the more distal region of the first catheter member 310, within the region of the distal taper discussed above, the annular space 212 is compressed and either closes or is substantially closed to fluid flow, thereby effectively sealing the distal end of the first lumen 210 near the transition to the proximal attachment point of the inflatable balloon 140, as depicted in FIG. 9A.

The third catheter member 130 passes longitudinally into the first lumen 230 of the second catheter member 320 and has a first lumen 230 passing longitudinally through the third catheter member 130. As with the first catheter member 130 of the first alternative embodiment described above, the first lumen 230 of the third catheter member 130 permits monitoring of conditions within the body, such as arterial pressure monitoring by hydrostatic pressure within a fluid column within the first lumen 230, or allows for the introduction of tethered sensors, such as flow sensing wires, pressure sensing wires or the like to the distal end of the balloon catheter system 300. First lumen 230 may also be used to deliver drugs, contrast media, or permit the introduction or withdrawal of fluids to and from the body.

Figure 9D:
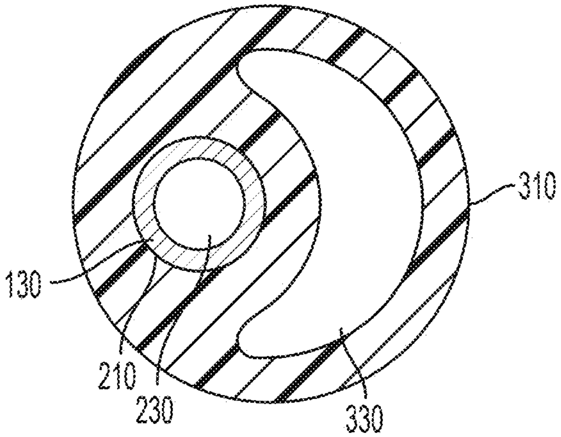
FIG. 9D is a cross-sectional view of the occlusion catheter system of FIG. 9, taken along line 9D-9D of FIG. 9, wherein the lumens and catheters are sized differently than the embodiment of FIG. 9C.

As with the alternative embodiment discussed above with reference to FIGS. 1-8, the embodiment depicted in FIGS. 9-9D may, optionally, include the second catheter member 320 being constructed of plural segments having distally increasing flexibility, such as by making the segments of distally decreasing durometer polymer or fashioning the second catheter member 320 to have a distally tapering wall thickness. The second catheter member 320 may be formed of discrete segments abutted and coupled together to form an elongated second catheter member 320 with either distally decreasing durometer or distally tapering wall thicknesses. Alternatively, the second catheter member 320 may be made by extrusion or molding polymers of distally decreasing durometer or distally tapering wall thicknesses.

As with the alternative embodiment of the balloon catheter system 100, the second catheter member 320 includes an open port 170 that is in fluid flow communication with the first lumen 230 of the third catheter member. Similarly, as with the balloon catheter system 100, the balloon catheter system 300 of the second preferred embodiment includes a guiding atraumatic tip (not shown in FIGS. 9-9D) as described above with reference to guiding atraumatic tip 150 of the first preferred embodiment, which is coupled to a distal end of the second catheter member 320.

Figure 10:
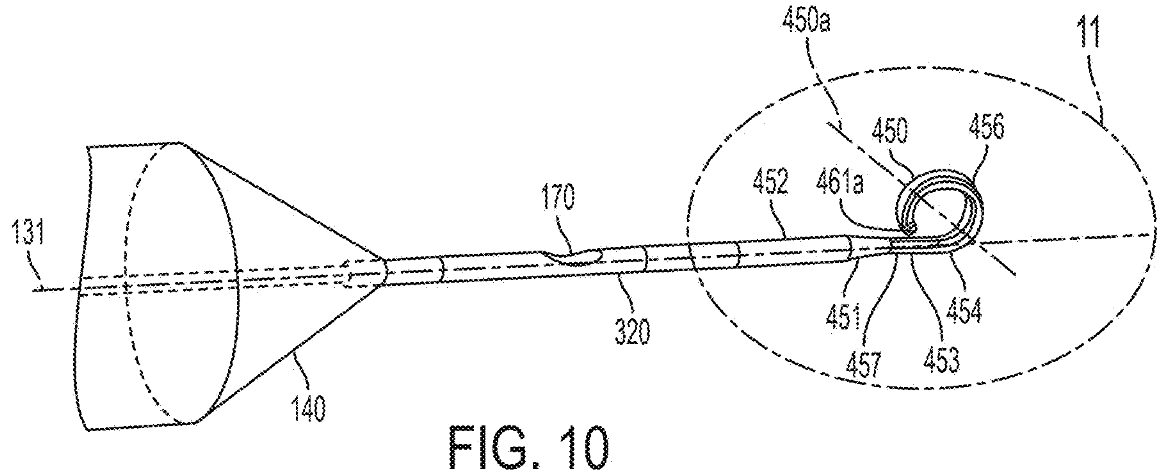
FIG. 10 is a magnified top perspective view of an alternative embodiment of a distal portion of the occlusion catheter system of FIG. 9.
Figure 11:
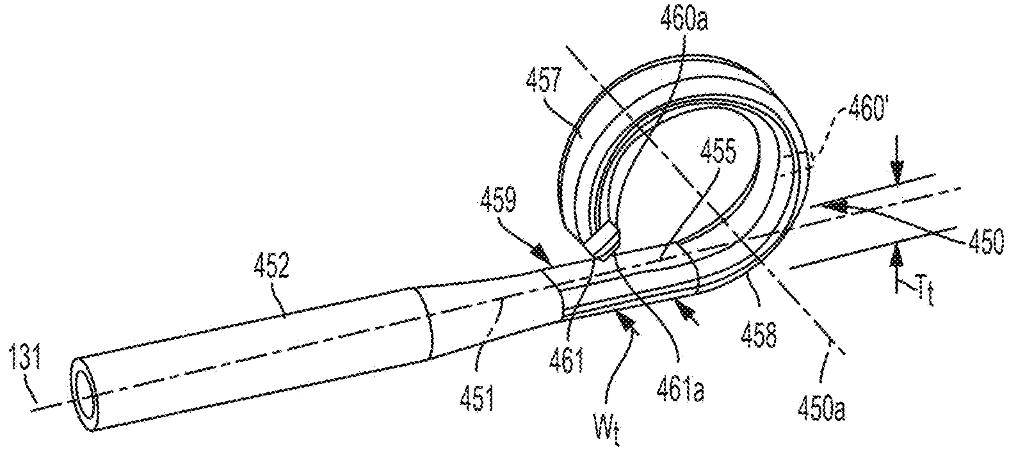
FIG. 11 is a magnified top perspective view an atraumatic tip of the occlusion catheter system of FIG. 10, taken from within shape 11 of FIG. 10.
Figure 13:
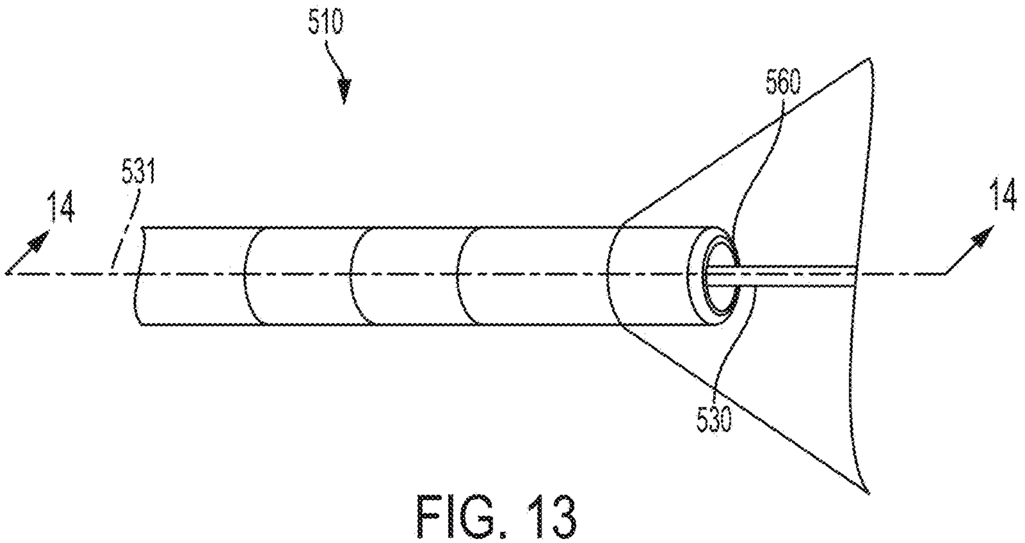
FIG. 13 is an enlarged top perspective view of the occlusion catheter system of FIG. 12, taken from within shape 13 of FIG. 12.
Figure 12:
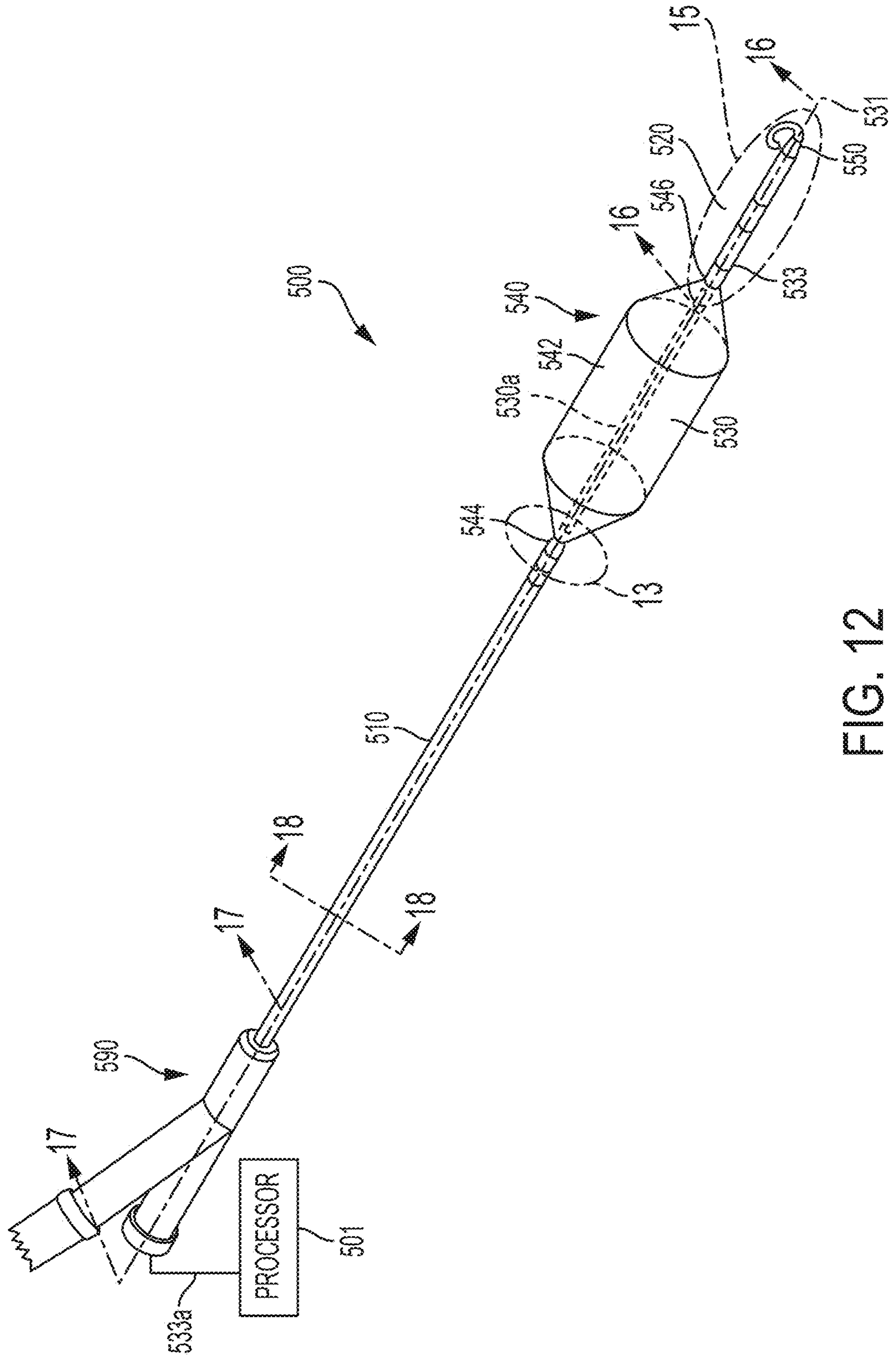
FIG. 12 is a top perspective view of a third preferred embodiment of an occlusion catheter system of the preferred present invention.

With reference to FIGS. 10 and 11, there is depicted an alternative embodiment of the guiding atraumatic tip 450. It will be understood that guiding atraumatic tip 450 may be employed with any of the foregoing embodiments of the preferred balloon catheter system 100 or of the second preferred balloon catheter system 300. The guiding atraumatic tip 450 is comprised generally of a polymeric cylindrical or tubular member 452 that has a distal section 454 that has been formed into a generally flattened cylinder having two generally planar opposing surfaces 455, 457 and two generally curved opposing surfaces 458, 459. The two generally planar opposing surfaces 455, 457 include an inner planar surface 455 and an outer planar surface 457. The distal section 454 has a distally extending section 453 that projects distally and a curved section 456 continuous with the distally extending section that curves away from the central longitudinal axis 131 of the balloon catheter system 100, 300 then proximally toward the occlusion balloon 140 and subtends a generally circular arc toward the central longitudinal axis 131 of the balloon catheter system 100, 300. The angle of the curve may be between about one hundred eighty degrees (180°) and three hundred fifty-five degrees (355°), more preferably between about two hundred seventy degrees (270°) and three hundred fifty degrees (350°) and even more preferably between about three hundred degrees (300°) and three hundred fifty degrees (350°)

such that a gap is provided between the terminal end of the generally cylindrical flattened distal section 454 and the more proximal surface of the distal section 454. It will also be understood that the distally extending section 453 and curved section 456 may be formed as a generally in-plane circular shape or may be formed as an out-of-plane generally helical shape, where a terminal end of the curved section 456 is laterally displaced from the central longitudinal axis 131 of the balloon catheter system 100 or balloon catheter system 300. In this manner, the generally flattened distal section 454 is characterized by a generally circular profile. The atraumatic tip 550 preferably operates in a manner similar to the guiding atraumatic tips 150, 350 of the previously described preferred embodiments, but is made of a polymer material without the need for a reinforcing member 152, as described above.

In the preferred embodiment, a tip thickness $T_t$ is defined between the inner planar surface 455 and the outer planar surface 457 and tip width $W_t$ is defined between the opposing curved lateral surfaces 458, 459. The tip width $W_t$ is preferably greater than the tip thickness $T_t$ such that the atraumatic tip 450 is readily flexible about a central tip axis 450*a*. The atraumatic tip 450 is preferably flexible about the central tip axis 450*a* from the substantially circular profile in the relaxed configuration to the introduction configuration, wherein the atraumatic tip 450 is relatively straight or positioned on the longitudinal central axis 431. In the preferred embodiment, the tip thickness $T_t$ is less than the tip width $W_t$. The relatively smaller tip thickness $T_t$ in comparison to the tip width $W_t$ facilitates the flexing of the atraumatic tip 450 from the relaxed configuration with the substantially circular profile to the introduction configuration, wherein the atraumatic tip 450 is substantially straight and is positioned on the longitudinal central axis 431 and renders bending of the atraumatic tip 450 laterally more difficult.

A tapered transition section 451 may, optionally, be provided between the polymeric cylindrical or tubular member 452 and the generally flattened cylindrical distal section 454. Guiding atraumatic tip 450 may be integral with the third catheter member 120 of balloon catheter system 100 or the second catheter member 320 of balloon catheter system 300. Alternatively, guiding atraumatic tip 450 may be fabricated as a discrete member and joined to the third catheter member 120 of balloon catheter system 100 or the second catheter member 320 of balloon catheter system 300.

The guiding atraumatic tip 450, which may be made of polyether block amide (PBAX, Arkema, Paris France) having a durometer of forty (40 D), or a similar polymer, such as polyurethane or polyethylene, that is compatible with the catheter shaft and balloon to make bonding easier and more secure. As discussed above, the guiding atraumatic tip 450 may be either cylindrical or tubular, or have a solid cylindrical section and a tubular section. The curve of the guiding atraumatic tip 450 may be made by any of a wide number of processes, including, for example, injection molding, round extrusion, flattening and post-processing into the curved distal section 456, a flat extrusion bonded to a round extrusion, or an extrusion that is pressed into a hot die having a shape of the desired curved distal section 450.

The atraumatic tip 450 may include a radio opaque tip marker 460. The radio opaque tip marker 460 may be implemented as a band surrounding the tip 450 or as a two-dimensional planar material on one or both of the planar opposing surfaces 455. Alternatively, the radio opaque tip marker 460 may be located at the most distal point of the atraumatic tip 450 indicated at 460' in FIG. 11. The band or the planar material may be composed of any suitable radio opaque material, such as for example, stainless steel or a suitable alloy such as platinum iridium. In another example embodiment, the tip 450 may be made of a plastic or polymer, such as for example, PEBAX that is impregnated with a radio opaque material. In another example embodiment, the plastic or polymer composition forming the tip 450 may be mixed with a radio opaque compound such as for example barium sulfate sufficient to permit visualization of the tip 450 using x-ray or fluoroscopy.

In an alternative embodiment described herein with reference to FIGS. 12-18, a balloon catheter system 500 generally includes a catheter assembly having a stiffener member 530, which is preferably comprised of a solid wire, an inflation catheter member 510 having an inflation lumen 610, a distal catheter member 520, an inflatable balloon 540, a proximal hub 590 and a guiding atraumatic tip 550. The stiffener member 530 is secured to the proximal hub 590 and extends longitudinally through the inflation catheter member 510 along the longitudinal axis 531 of the stiffener member 530, which substantially comprises the longitudinal axis 531 of the catheter system 500. The stiffener member 530 includes a proximal end 530*b*, a distal end 530*c* and defines the longitudinal axis 531. The stiffener member 530 is coupled at the proximal end 530*b* to the proximal hub 590 and at the distal end 530*c* to a proximal section of the distal catheter member 520. The proximal hub 590 includes an inflation connection port 590*a* with an inflation fluid pathway 594 therein. The inflation lumen 610 of the inflation catheter member 510 is in fluid communication with the inflation fluid pathway 594 and extends longitudinally through the inflation catheter member 510. The inflation lumen 610 preferably terminates at a first port 560 distal to a proximal balloon end 544 of and within a space 542 defined by the inflatable balloon 540, such that the inflation lumen 610 is in fluid flow communication with the space 542 within the inflatable balloon 540 to convey an inflation fluid to and from the inflatable balloon 540 from a source external the balloon catheter system 500 that is preferably connected to the inflation connection port 590*a*. The distal catheter member 520 is coupled at a proximal end thereof to a distal end of the stiffener member 530. The inflation catheter member 510 and the distal catheter member 520 are positioned in longitudinal co-axial spaced apart relationship from one and other along a longitudinal axis 531 of the stiffener member 530, thereby defining an intermediate region 530*a* of the stiffener member 530 within the space 542 within the inflatable balloon 540 that is not covered by either the inflation catheter member 510 or the distal catheter member 520.

In this preferred embodiment of the balloon catheter system 500, when the occlusion balloon 540 is in an uninflated condition, the catheter system 500 is of sufficiently small cross-segmental dimension to pass through a five to six (5-6) French (1.67-2 mm) percutaneous sheath, such as, for example six (6) French (2 mm) introduction sheath. Thus, the balloon catheter system 500 has a greatest outer diameter, when the occlusion balloon 540 is uninflated, of less than 1.67-2 mm. The balloon catheter system 500 of the preferred embodiment of FIGS. 12-18 preferably has a smaller greatest outer diameter when the occlusion balloon 540 is uninflated than the above-described preferred catheter system 100 because of the solid stiffener member 530, which replaces the first catheter 130 with the first lumen 230 therein. It will be understood by those skilled in the art that the balloon catheter system 500 is not limited to a dimension sufficient to pass through a five to six (5-6) French percutaneous sheath, but that such lower profile or smaller maximum diameter when the occlusion balloon 540 is uninflated is generally considered desirable to enable passage of a balloon catheter system 500 through tortuous vasculature and to a desired position within the body for purposes of arterial occlusion. In addition, the reduced maximum diameter limits the size of the percutaneous introduction puncture in the patient's skin and may limit the clinical requirements for the medical professionals performing the procedure. The balloon catheter system 500 is, therefore, not intended to be limited to this dimensional size, but may be made of smaller or larger dimension as desired or needed.

In general, the alternative embodiment described herein with reference to FIGS. 12-18 includes the stiffener member 530, preferably the solid wire, instead of a tube with a lumen. The solid stiffener member 530 may be implemented as a solid flexible wire made of any suitable material that may be formed into a wire-like component. Examples of materials that may be used include polymeric materials, biocompatible metals, nitinol and stainless steel. The stiffener member 530 of this preferred embodiment may be constructed of a solid nitinol hypotube. The nitinol hypotube stiffener member 530 provides flexibility and sufficient stiffness along the longitudinal axis 531 and is generally a small diameter tube or wire. The stiffener member 530 implementation without a lumen removes the fluid communication with a third lumen. The stiffener member 530 does, however, allow for the implementation of a catheter system having a lower profile than the first embodiment of the catheter system 100.

In the alternative embodiment of FIGS. 12-18, the catheter system 500 preferably includes a pressure sensor 533 mounted distally of the occlusion balloon 540 or on a surface of the occlusion balloon 540 proximate its distal balloon end 546. The pressure sensor 533 preferably communicates with a processor 501 that may be wired to the pressure sensor 533 or may receive pressure readings from the pressure sensor 533 through wireless communication techniques. In the preferred embodiment, the pressure sensor 533 is wired to and in communication with the processor 501 by an electrical wire 533*a* that carries pressure signals from the pressure sensor 533 to the processor 501. The electrical wire 533*a* of the preferred embodiment extends at least partially through the inflation lumen 610 and is in electrical contact with the pressure sensor 533 and the processor 501. The preferred pressure sensor 533 is mounted to an external surface of the distal catheter member 520 to sample and detect pressures at the distal side of the inflatable balloon 540. For example, the pressure sensor 533 may sample pressure near the distal balloon end 546 of the inflatable balloon 540 during use and transmit the pressure readings to the processor 501 for review by an operator, medical technician or physician. The pressure sensor 533 may also be utilized to provide pressure measurements at predetermined intervals to the processor 501. The processor 501 may adjust the inflation of the occlusion balloon 540 to permit limited flow through the vessel to the distal balloon end 546 of the occlusion balloon 540. The processor 501 may be controlled to maintain a range of pressures at the distal balloon end 546 or a minimum pressure based on inflation and deflation of the occlusion balloon 540.

Referring to FIGS. 12-18, the inflatable balloon 540 is attached at its proximal balloon end 544 to a distal end of the inflation catheter member 510 and at its distal balloon end 546 to a proximal end of the distal catheter member 520. In operation, the inflatable balloon 540 is inflated by introducing an inflation fluid, such as saline, from an external source, such as a syringe, coupled to the proximal hub 590, into and through the inflation lumen 610, out of the first port 560 and into the space 542 within the inflatable balloon 540. Inflation and deflation of the inflatable balloon 540 in FIGS. 1-8 is performed as described above with reference to FIGS. 1-8.

Figure 15:
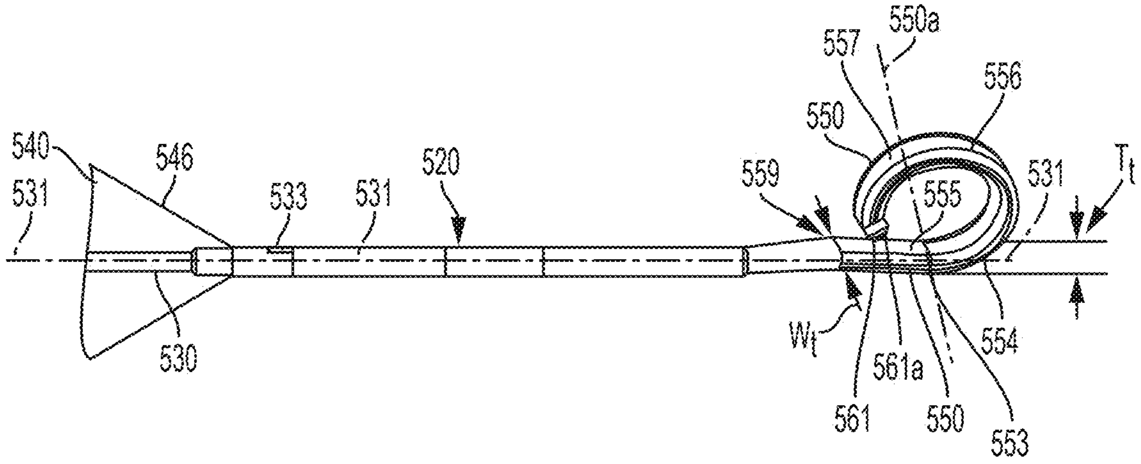
FIG. 15 is a top perspective view of the occlusion catheter system of FIG. 12, taken from within shape 15 of FIG. 1.
Figure 16:
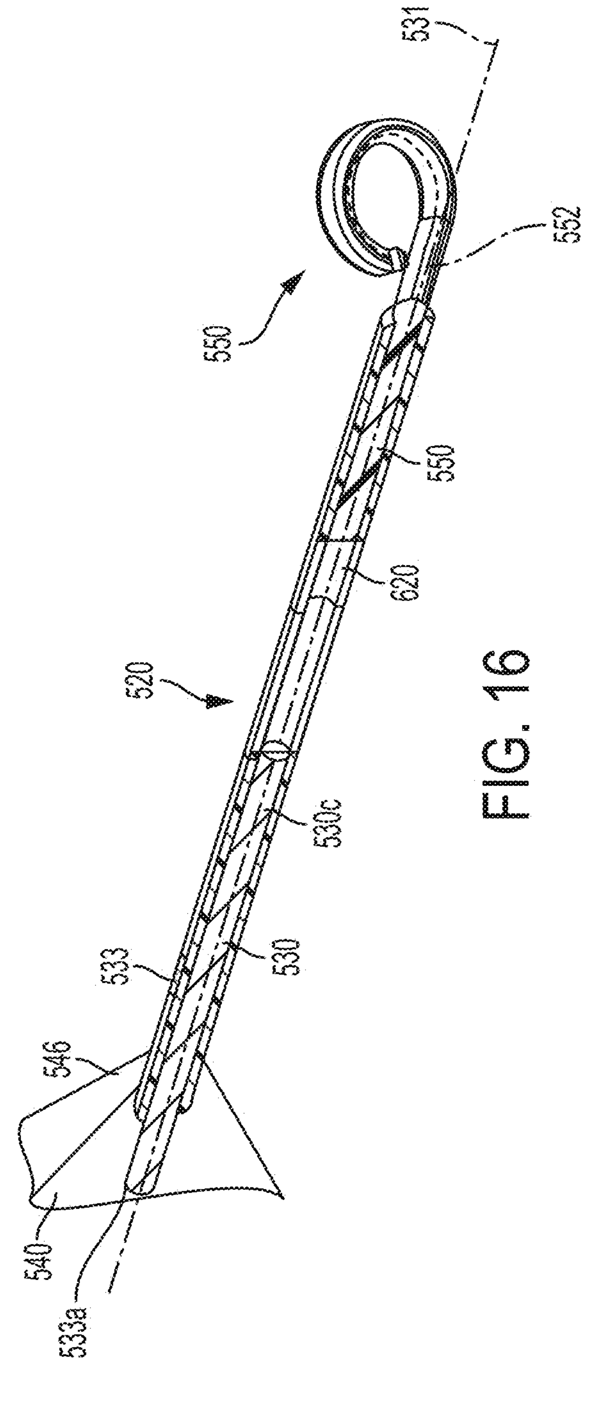
FIG. 16 is a cross-sectional view of the occlusion catheter of FIG. 12, taken along line 16-16 of FIG. 12.

Referring to FIGS. 15 and 16, the distal catheter member 520 is fixedly coupled at its proximal end concentrically about a distal end of the stiffener member or solid wire 530. In the preferred example shown in FIG. 16, the distal catheter member 520 has a lumen 620 extending longitudinally through the distal catheter member 520 and coupled concentrically about a proximal end of the atraumatic tip 550. The distal catheter member 520 is not limited to including the lumen 620 and may be configured as substantially solid between its proximal and distal end or integrally formed with or fixed to the atraumatic tip 550. The guiding atraumatic tip 550 may be constructed of an elastic, shape memory and/or superelastic material, such as a metal or polymer. A reinforcing member 552 (depicted in phantom) may optionally be included either within the guiding atraumatic tip 550 or wound about an external surface of the guiding atraumatic tip 550 to offer additional reinforcement to the tip 550. The guiding atraumatic tip 550 projects distally from the distal catheter member 520 and preferably has a generally flattened configuration, curving proximally and then toward the central longitudinal axis 531 of the balloon catheter system 500, but leaving a unconnected end 561 at the distal end of the guiding atraumatic tip 550. The atraumatic tip 550 is preferably designed and configured such that the atraumatic tip 550 is able to unfold from a relaxed configuration (FIG. 16) and assume a linear configuration co-axial with the central longitudinal axis 531 of the balloon catheter system 500 for delivery. During introduction, the atraumatic tip 550 is preferably straightened along the longitudinal axis 531 in an introduction configuration such that the atraumatic tip may be positioned within a catheter for introduction and returns to the substantially circular-shape in the relaxed configuration when the atraumatic tip 550 emerges from the catheter in the patient's vessel. Specifically, the atraumatic tip 550 preferably has sufficient flexibility such that the substantially circular curve of the atraumatic tip 550, in the relaxed configuration, may be straightened coaxially with the longitudinal axis 531 for introduction of the catheter system 500 into the patient's vessel through an introduction catheter.

The atraumatic tip 550 of the preferred embodiment has a smaller thickness between the inner and outer planar surfaces 555, 557 than the lateral outer opposing surfaces 558, 559 of the atraumatic tip 550. This flattened shape of the atraumatic tip 550 facilitates the folding or flexing of the atraumatic tip along the longitudinal axis 531. The shape and configuration of the preferred atraumatic tip 550 preferably limits bending and folding of the atraumatic tip 550 laterally relative to the longitudinal axis 531. In addition, the relatively flattened atraumatic tip 550 provides manufacturing advantages when the atraumatic tip is constructed of a polymeric material compared to the substantially cylindrical atraumatic tip 150 shown in the first preferred embodiment. In the preferred embodiment, the lateral outer surfaces 558, 559 are substantially arcuate, but are not so limited and may be relatively planar or otherwise configured.

In the preferred embodiment, a tip thickness $T_t$ is defined between the inner planar surface 555 and the outer planar surface 557 and tip width $W_t$ is defined between the opposing curved lateral surfaces 558, 559. The tip width $W_t$ is preferably greater than the tip thickness $T_t$ such that the atraumatic tip 550 is readily flexible about a central tip axis 550*a*. The atraumatic tip 550 is preferably flexible about the central tip axis 550*a* from the substantially circular profile in the relaxed configuration to the introduction configuration, wherein the atraumatic tip 550 is relatively straight or positioned on the longitudinal central axis 531. In the preferred embodiment, the tip thickness $T_t$ is less than the tip width $W_t$. The relatively smaller tip thickness $T_t$ in comparison to the tip width $W_t$ facilitates the flexing of the atraumatic tip 550 from the relaxed configuration with the substantially circular profile to the introduction configuration, wherein the atraumatic tip 550 is substantially straight and is positioned on the longitudinal central axis 431 and renders bending of the atraumatic tip 550 laterally more difficult.

The atraumatic tip 550 of the alternative preferred embodiment of the catheter system 500 is preferably configured and functions similar to the above-described atraumatic tip 450 of the preferred embodiment of FIGS. 10 and 11. The atraumatic tip 550 is preferably formed into the generally flattened frusta-cylinder having the two generally planar opposing inner and outer surfaces 555, 557 and two generally curved opposing lateral surfaces 558, 559. The atraumatic tip 550 has a distally extending section 553 that projects distally and a curved section 556 continuous with the distally extending section 553 that curves away from the central longitudinal axis 531 of the balloon catheter system 500 then proximally toward the occlusion balloon 540 and subtends a generally circular arc toward the central longitudinal axis 531 of the balloon catheter system 500. In the relaxed configuration, the atraumatic tip 550 preferably has a substantially circular profile when viewed from the side, but is not so limited and may have nearly any sized and shaped profile that limits introduction of the atraumatic tip 550 into an alternative or smaller vessel path than desired by the physician or medical professional. The angle of the curvature may be between about one hundred eighty degrees (180°) and three hundred fifty-five degrees (355°), more preferably between about two hundred seventy degrees (270°) and three hundred fifty degrees (350°) and even more preferably between about three hundred degrees (300°) and three hundred fifty degrees (350°) such that a gap 561*a* is provided between the unconnected end 561 of the generally cylindrical flattened distal section 554 and the more proximal surface of the distal section 554. The generally flattened section 554 provides manufacturing and functional advantage when compared to a cylindrical atraumatic tip, such as the atraumatic tip 150 described in FIGS. 4 and 5. The flattened atraumatic tip 550 of this alternative preferred embodiment permits flexibility of the atraumatic tip 550 about a plane or axis extending substantially laterally through the atraumatic tip 550, generally perpendicular to the longitudinal axis 531 to accommodate straightening of the atraumatic tip 550 coaxially with the longitudinal axis 531 for introduction. In addition, the greater lateral thickness of the atraumatic tip 550 laterally relative to the longitudinal axis 531 provides stiffness to the atraumatic tip 550 such that the tip 550 is more difficult to bend or flex out of its preferred shape laterally relative to the longitudinal axis 531 during placement of the balloon 540 and movement of the catheter system 550 through the major vessels of the patient.

A tapered transition section 551 is preferably provided between a substantially cylindrical portion of the distal catheter member 520 and the generally flattened distal section 554. The preferred guiding atraumatic tip 550 is integral with the distal catheter member 520 of balloon catheter system 500. Alternatively, the guiding atraumatic tip 550 may be fabricated as a discrete member and joined to the distal catheter member 520 of balloon catheter system 500.

The guiding atraumatic tip 550 is preferably constructed of a polyether block amide (PBAX, Arkema, Paris France) having a durometer of forty (40 D), or a similar polymer, such as polyurethane or polyethylene, that is compatible with the distal catheter member 520 and the balloon 540 to make bonding easier and more secure. As discussed above, the guiding atraumatic tip 550 may be generally flattened, cylindrical or tubular, or have a solid cylindrical section and a tubular section. The curve of the guiding atraumatic tip 550 may be made by any of a wide number of processes, including, for example, injection molding, round extrusion, flattening and post-processing into the curved distal section 556, a flat extrusion bonded to a round extrusion, or an extrusion that is pressed into a hot die having a shape of the desired curved distal section 550.

The atraumatic tip 550 may include a radio opaque tip marker 560*a* at the unconnected end 561. The radio opaque tip marker 560*a* may be implemented as a band surrounding the tip or unconnected end 561 or as a two-dimensional planar material on one or both of the planar opposing surfaces 555, 557. The radio opaque marker 560*a* may be constructed of any suitable radio opaque material, such as for example, stainless steel or a suitable alloy such as platinum iridium. In another example embodiment, the tip 550 may be constructed of a plastic or polymer, such as for example, PEBAX that is impregnated with a radio opaque material to define the radio opaque tip marker 560*a*. In another example embodiment, the plastic or polymer composition forming the atraumatic tip 550 may be mixed with a radio opaque compound such as for example barium sulfate sufficient to permit visualization of the tip 550 using x-ray or fluoroscopy to define the radio opaque tip marker 560*a*.

As noted above in the description of the first preferred embodiment of the balloon catheter system 100 illustrated in FIGS. 1-8, the balloon catheter system 100, when the inflatable balloon 140 is in an uninflated condition, is of sufficiently small cross-segmental dimension to pass through a 6 to 8 French (2-2.67 mm) percutaneous sheath, such as, for example, 7 French (2.33 mm). Thus, the balloon catheter system 100 has a greatest outer diameter, when the inflatable balloon 140 is uninflated, of less than 2-2.67 mm. It will be understood by those skilled in the art that example implementations of the alternative embodiment of the balloon catheter system 500 described herein with reference to FIGS. 12-18 may have an even smaller cross-sectional dimension due to the use of the stiffener member or solid wire 530 instead of a catheter with a lumen. The diameter of the stiffener member 530 is smaller than the inner diameter of the inflation lumen 610 of the inflation catheter member 510, thereby forming an annular space 612 between the outer surface of the solid stiffener member 530 and the inner surface of the inflation catheter member 510. The dimensions of the inner diameter of the inflation lumen 610 and the diameter of the stiffener member 530 may be specified in example implementations to provide optimal inflation fluid flow as well as a reduced profile that may further ease deployment.

Figure 14:
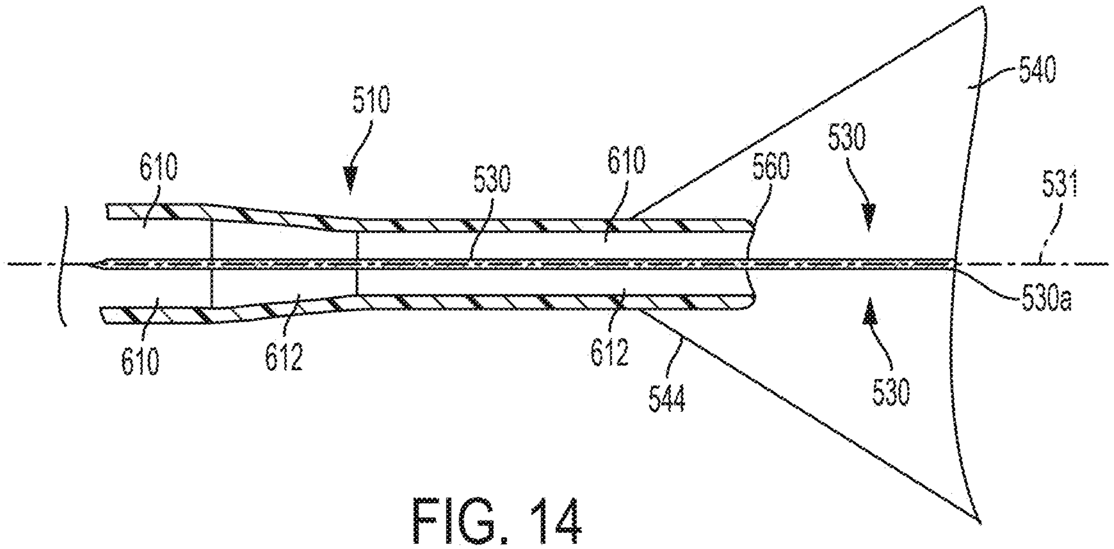
FIG. 14 is a cross-sectional view of the occlusion catheter system of FIG. 13, taken along line 14-14 of FIG. 13.

Turning now to FIGS. 14-16, the distal portion of the balloon catheter system 500 is illustrated. As shown in FIG. 16, the outer surface of the stiffener member 530 is coupled to at least a portion of the inner surface of the second lumen 620, such that there is no annular space between the outer surface of the stiffener member 530 and the inner surface of the second lumen 620. Referring now to FIG. 15, the distal catheter member 520 may include a plurality of segments of distally decreasing durometer polymer to provide a step-down transition to the guiding atraumatic tip 150. The number of step down durometer segments may be between one (1) and six (6) and may step down in decreasing fashion by regular or irregular increments, such, for example 75 D, 63 D, 55 D, 40 D, etc. Alternatively, the distal catheter member 520 may be made of a single durometer polymer, but having distally tapering wall thicknesses to impart a flexibility gradient to the third catheter member 520. The plurality of segments of decreasing durometer plastic may be abutted and be bonded together or may be manufactured from a single extrusion including decreasing durometer hardness.

In an alternative embodiment, the stiffener member 530 may extend completely into the space shown for the second lumen 620 such that the distal catheter member 520 completely covers the distal end of the stiffener member 530. The atraumatic tip 550 may by formed as an extension of the second catheter body 520.

Figure 17:
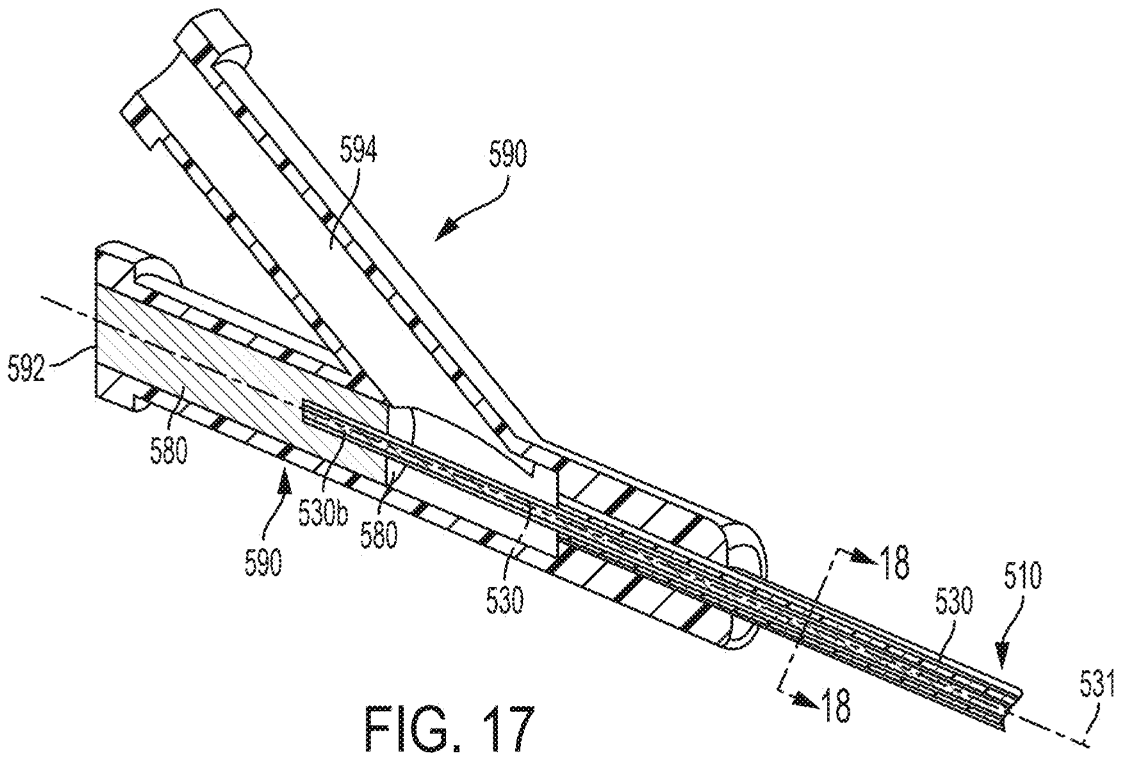
FIG. 17 is a cross-sectional view of the occlusion catheter system of FIG. 12, taken along line 17-17 of FIG. 12.
Figure 18:
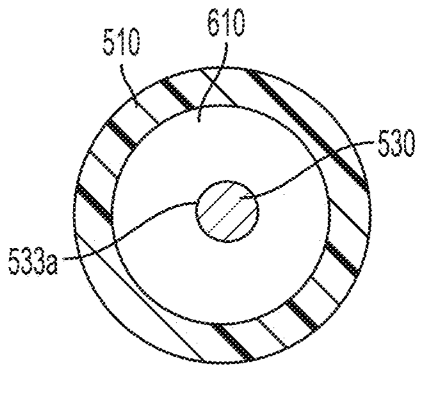
FIG. 18 is a cross-sectional view of the occlusion catheter system of FIG. 12, taken along line 18-18 of FIG. 12.

Turning now to FIG. 17, the proximal portion of the balloon catheter system 500 is illustrated. The inflation catheter member 510 is coupled to the proximal hub 590 and the proximal end of the stiffener member or solid wire 530 is fixedly coupled to the proximal hub 590 at a proximal bonding site, preferably using an adhesive 580, to bond an inner wall surface of the proximal hub 590 to an outer wall surface of the solid stiffener member 530. The amount of adhesive 580 used is preferably sufficient to fixedly couple the solid stiffener member 530 to the proximal hub 590. As shown in FIG. 17, the adhesive 580 may fill the entire portion 592 of the proximal hub 590 that holds the stiffener member 530. The proximal end of the stiffener member 530 is not limited to being adhesively bonded to the proximal hub 590 and may be otherwise fastened, secured or fixed to the proximal hub 590, as long as the stiffener member 530 is substantially secured to the proximal hub 590 such that the stiffener member 530 provides stiffness for the balloon catheter system 500, the stiffener member 530 is substantially secured relative to the inflation catheter member 510 and the occlusion balloon 540, the assembly is able to withstand the normal operating conditions of the catheter system 500 and securement results in a structure able to perform the preferred functions of the catheter system 500, as is described herein. Since the solid stiffener member 530 has no lumen, no fluid pathway is needed in the portion 592 that holds the stiffener member 530 and the stiffener member 530 can have a relatively small diameter, thereby reducing the overall diameter of the catheter system 500. As illustrated, the proximal hub 590 has an inflation fluid pathway 594. The inflation fluid pathway 594 communicates with the inflation lumen 610 of the inflation catheter member 520. In this alternative preferred embodiment, the inflation lumen 610 is defined between the outer surface of the stiffener member 530 and an inner surface of the inflation catheter member 510. It will be understood that the proximal hub 590 may be configured to have more than the inflation fluid pathway 594, with each fluid pathway communicating with a different one of any additional lumens in the balloon catheter system 500.

It will be understood that when reference is made to coupling two or more component sections, members or pieces of the balloon catheter system, that conventional catheter material bonding modalities are intended to be encompassed and employed. For example, a wide variety of biocompatible adhesives useful in catheter manufacture are known, similarly, thermobonding techniques used in catheter manufacture are also known. Thus, for example, where it is described that the guiding atraumatic tip is coupled to the third catheter member or to the distal catheter member, it is contemplated that such coupling may be made using thermobonding, biocompatible adhesives or other methods of fixedly bonding two components in medical devices.

It will also be understood by those skilled in the art that it is well known to manufacture catheters of a variety of medical grade, biocompatible polymers, such as, for example and without limitation, silicone, nylon, polyurethane, PETE, latex, thermoplastic elastomers, polyether block amides (PBAX, Arkema, Paris, France). Alternatively, it is known to manufacture catheters of metals, such as nitinol or stainless steel. Similarly, it is known to manufacture catheters of metal-reinforced polymer, such as, for example and without limitation, stainless steel braiding over polyurethane, stainless steel helical windings over silicone or nitinol reinforced polymer. Thus, any or all of the first catheter member, the second catheter member, the inflation catheter member, the distal catheter member, or the third catheter member in any of the foregoing embodiments may be fabricated of biocompatible polymers, biocompatible metals or metal-reinforced polymers, as is known in the art.

It will also be understood by those skilled in the art that while the implementation of radio opaque markers are described in the context of embodiments described with reference to FIGS. 1-8, it may be desirable to include radio opaque marker bands positioned at the proximal and distal ends of the balloon in implementations of embodiments described above with reference to FIGS. 9-11, and embodiments described above with reference to FIGS. 12-18. It is also desirable to include length markers on the outer catheter shaft to indicate to the physician the insertion depth of the balloon catheter system 100, the balloon catheter system 300, or the balloon catheter system 500. The length markers may be printed or laser etched onto the outside of the catheter shaft.

In each of the foregoing described embodiments of the vascular occlusion systems depicted in FIGS. 1-18, the catheter may also include sensors, transmitters, receivers, interrogators or other means for measuring physical and/or physiological parameters distal and/or proximal one or more of the expandable occlusion members, including, for example blood pressure sensors, heart rate sensors, flow sensors, chemical sensors, temperature sensors, oxygenation sensors, biological sensors, imaging sensors or the like.

The preferred catheters, sheaths, guide wires, balloons or other occlusion members, or other components that are introduced into the vasculature may be coated with a variety of coatings, including without limitation, antibacterial, antimicrobial, lubricants, anticoagulant and/or antifouling coatings. Thus, any or all components of any of the preferred systems described herein may further include one or more biocompatible coatings.

Occlusion Control System

Control over the apposition of the occlusion member against the vessel walls is preferably accomplished by controlling the inflation of the preferred balloons, selection of the size of the occlusion member, placement of the occlusion member or other methods and techniques that provide control to users of the preferred systems. Aortic occlusion may result in arterial hypertension upstream of an occlusion site as pressure builds against the occlusion member. If the arterial pressure reaches a deleterious hypertensive state, vascular rupture, stroke or other undesirable events may occur that could potentially injure the patient. Conversely, after the vascular occlusion is complete and blood flow is restored, there is a potential for concomitant drop in arterial blood pressure potentially leading to a hypotensive event that could result in a dangerously low blood pressure and, in extreme cases, cardiac arrest.

The preferred control systems are not limited to their utility with the preferred vascular occlusion catheter systems 100, 300, 500 of the present invention, but may be used virtually with any type of vascular occlusion system. Thus, in FIG. 19, there is shown a generic type of vascular occlusion system 700, while in FIGS. 20-22, the vascular occlusion catheter system is generically shown schematically and is designated by box 710, to denote a non-specific vascular occlusion catheter system, including, for all of FIGS. 19-22, without limitation, the first, second and third preferred vascular occlusion catheter systems 100, 300, 500 described above. Other vascular occlusion catheter systems that rely upon a pressure being applied to an occlusion member to urge the occlusion member into apposition with a vascular wall, thereby at least partially occluding the blood vessel are expressly included within the scope of occlusion control system of the present invention, such as the additional occlusion/perfusion systems described herein.

In each of the preferred embodiments of the occlusion control systems, the pressure sources are denominated schematically by a generic box or oval to denote that a wide variety of pressure sources are intended to be included within the preferred embodiments of the invention. The pressure source may be a syringe or syringe-like inflation device, an endoflator device, a pump or other similar means of applying a pressure to the occlusion member in the vascular occlusion catheter 710. As noted above, when a fluid is used as the pressure medium to activate the occlusion member, such as to fill an occlusion balloon, that fluid may be a liquid, including water, saline, contrast medium or any combination thereof, or may be a gas, including carbon dioxide, helium, air or oxygen. The fluid source may, in the instance of a liquid, be a liquid reservoir, a pre-measured volume of liquid in a vessel that is removably engageable with the pressure source or other similar container for holding and dispensing liquid from the fluid source to the pressure source. In the instance of a gas, the fluid source may be a gas reservoir or a pre-measured volume of pressurized gas in a canister that is removably engagement with the pressure source to deliver the pre-measured volume of gas to the pressure source. A canister with a pre-measured gas volume at a known pressure is also contemplated, for example, a carbon dioxide cartridges that are commercially available in a wide variety of mass of pressurized gas, including without limitation eight, twelve, sixteen, twenty-five or thirty-three grams (8 g, 12 g, 16 g, 25 g, 33 g). Converting mass to volume of a gas at standard temperature and pressure (STP) typically entails resolving the gas constant equation, as follows: $V=nRT/P$ wherein V is volume, n is mass, R is the molar volume of the gas, T is temperature (Kelvin) and P is pressure (atm). The volume of gas needed to inflate a specific occlusion member to a given inflation volume and inflation pressure may be calculated utilizing this preferred formula.

Figure 19:
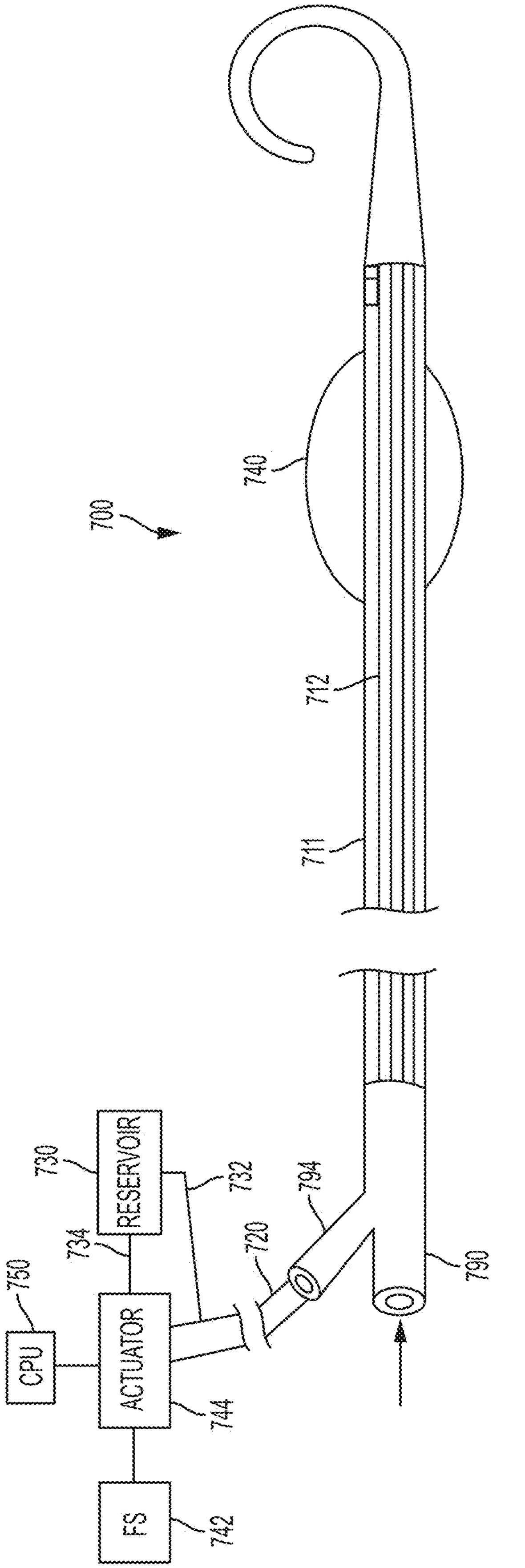
FIG. 19 is a diagrammatic rendering of a first preferred pressure regulation system for automatically releasing occlusion by any of the occlusion catheter systems of the first, second and third preferred embodiments of FIGS. 1-18.

Referring to FIG. 19, a first embodiment of the occlusion control system 700 includes a vascular occlusion catheter 711 has a proximal hub 790 that includes at least one pressure line port 794. The pressure line port 794 communicates with a pressure conduit or lumen 712 in the vascular occlusion catheter 711. The pressure conduit 712 may be a lumen within the vascular occlusion catheter 711 or may be a tubular conduit placed within a lumen in the vascular occlusion catheter 711. A pressure accumulator or reservoir 730 communicates with the pressure line port 794 via pressure line 732 that is, in turn, coupled to a connecting conduit 720 associated with pressure line port 794. An actuator 744, such as a fluid pump, is coupled to the pressure accumulator 730 and to a fluid source ("FS") 742. The actuator 744 is also operably coupled to a controller or central processing unit ("CPU") 750. The controller 750 operates as a computer control and may have an interface, not shown, that permits programming of computer control software that monitors and controls activation of the actuator 744 to regulate pressure in the occlusion member 740 and to collect data from sensors associated with the occlusion control system 700.

In accordance the preferred embodiment of occlusion control system 700, the occlusion member 740 has a first pressure Pmax, which is below the failure pressure of the occlusion member 740. The pressure accumulator 730 is preferably pressurized, such as with a fluid, to an accumulator pressure Pa, where the accumulator pressure $Pa<Pmax$, and where the accumulator pressure Pa is less than a predetermined maximum safe blood pressure Pbp within the vascular system being occluded, such that $Pa<Pbp<Pmax$. When the occlusion member 740 is in apposition with the vascular wall and the vessel is substantially occluded, the pressure exerted at the occlusion member 740 may be considered the apposition pressure Papp, wherein the apposition pressure Papp is substantially equal to the pressure in the accumulator 730 or the accumulator pressure Pa. In this preferred embodiment, when during occlusion the blood pressure Pbp against the occlusion member 740 exceeds the apposition pressure Papp, the accumulator pressure Pa in the accumulator 730 and in the occlusion member 740 is exceeded and the occlusion member 740 may yield to the blood pressure Pbp and release apposition against the vascular wall surface and allow fluid flow past the occlusion site. Since the apposition pressure Papp within the occlusion member 740 and the accumulator pressure Pa within the accumulator 730 is preferably a closed system, the pressure in the accumulator 730, such as the accumulator pressure Pa, will rise and when blood pressure reduces to be less than the accumulator pressure Pa in the accumulator 730 and the apposition pressure Papp within the occlusion member 740, the occlusion member 740 will preferably reestablish occlusion.

This effect of automatically adjusting apposition pressure Papp in response to an elevation in blood pressure Pbp, causing a release of apposition against the vascular wall and, therefore, releasing the occlusion and permitting fluid flow past the occlusion site, in turn lowers the blood pressure head against the occlusion member 740. When the blood pressure Pbp upstream of the occlusion member 740 has downwardly adjusted to below the accumulator pressure Pa and the apposition pressure Papp, the occlusion member 740, under the influence of the elevated pressure in the accumulator 740, reestablishes apposition and, therefore, occlusion is reestablished. This cycle may be likened to "burping" as a pressure release.

One further aspect of the occlusion control system 700 illustrated in FIG. 19, is that the preferred computer controller 750 preferably monitors the accumulator pressure Pa, the blood pressure Pbp and the apposition pressure Papp and, when required, either automatically or after providing audible or visual notification to a medical practitioner and input from the medical practitioner, actuates the actuator 744 to draw fluid from fluid source 742 and communicates the drawn fluid to the occlusion member 740 to increase the apposition pressure Papp. Conversely, where apposition pressure Papp is determined by the computer controller 750 or by the medical practitioner to be too high, the actuator 744 may be controlled to withdraw fluid from the occlusion member 740, lowering apposition pressure Papp and moving fluid from the occlusion member 740 to the fluid source 742.

The occlusion control system 700 is preferably a bidirectional system capable of increasing the occlusion pressure or apposition pressure Papp or decreasing the occlusion pressure or apposition pressure Papp under either manual control or under control of the computer processor 750. Moreover, the preferred occlusion control system 700 is operable to automatically release the apposition when the blood pressure Pbp impinging on the occlusion member 740 is above a pre-determined level (typically that regarded as safe for the patient). Accordingly, the occlusion control system 700 preferably includes a pressure sensor that is able to sense blood pressure on the proximal or distal side of the balloon 740 to measure the blood pressure Pbp impinging on the occlusion member 740 and to adjust inflation pressure or apposition pressure Papp of the occlusion member 740 to at least partially control the blood pressure Pbp in the vessel.

Figure 20:
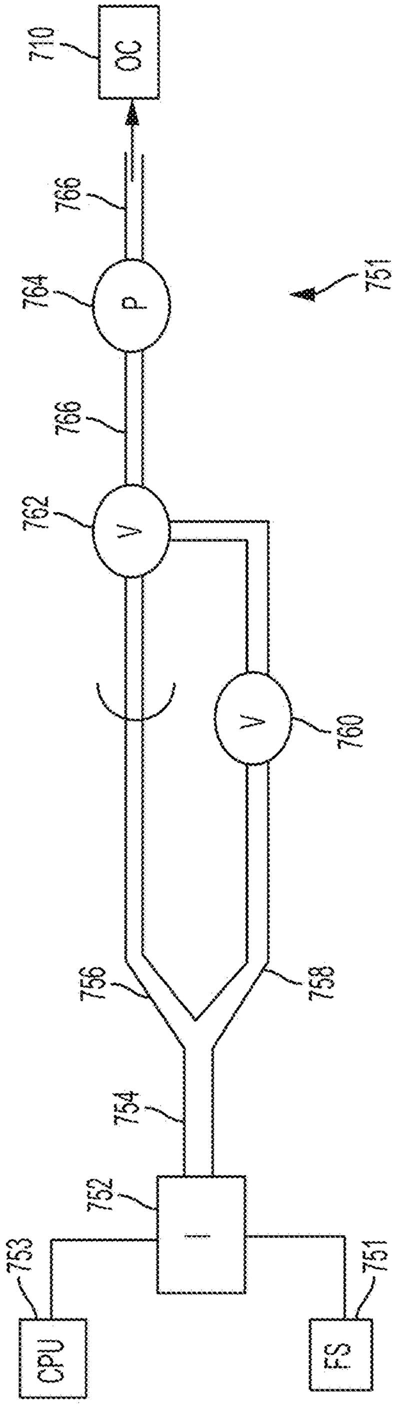
FIG. 20 is a diagrammatic rendering of a second preferred pressure regulation system for controlling the occlusion balloon of any of the occlusion catheter system of the first, second and third preferred embodiments of FIGS. 1-18.

An alternative or second preferred embodiment of occlusion control system 751 is depicted in FIG. 20. In alternative or second preferred embodiment of the occlusion control system 751, the occlusion catheter 710 is under control of a pressure source ("I") 752, which in the case of a fluid is coupled to a fluid source ("FS") 751. Similar to the first preferred occlusion control system 700, the pressure source 752 may be under manual control, under automatic control of a computer processor 753, or under manual control interfacing with the computer processor 753. A pressure conduit 754 preferably bifurcates into a free line 756 and a regulated line 758. A check valve 760 is preferably positioned in-line in the regulated line 758. An actuable valve 762 is preferably interposed in both the free line 756 and the regulated line 758, and is operable to select the free line 756, the regulated line 758 or both the free line 756 and the regulated line 758. A fluid conduit 766 leads from the actuable valve 762 to the occlusion catheter 710. A pressure sensor 764 may be interposed within fluid conduit 766 to monitor pressure during operation of the second preferred occlusion control system 751 and may alternatively be positioned in the occlusion control system 751 to detect pressure at various locations relative to the system 751, such as within an occlusion balloon or at proximal and/or distal ends of the occlusion balloon. The pressure sensor 764 may be a pressure gauge, electronic pressure sensor or pressure sensor that provides visual signal to the medical practitioner directly or may feed a pressure signal to the computer processor 753 that controls the occlusion control system 751, in turn, upon the pressure signal and/or displays pressure data to the medical practitioner.

Figure 21:
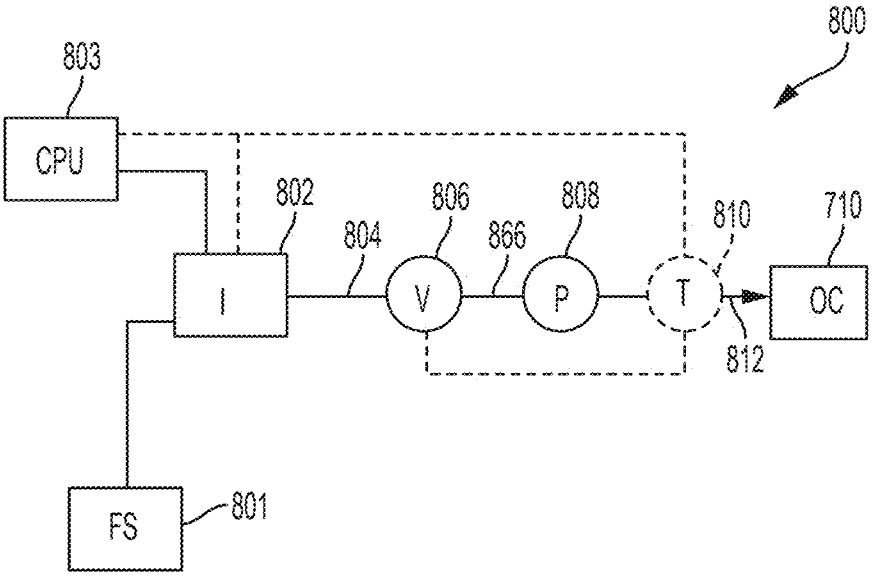
FIG. 21 is a diagrammatic rendering of a third preferred pressure regulation system for controlling the occlusion balloon of any of the occlusion catheter system of the first, second and third preferred embodiments of FIGS. 1-18.
Figure 22:
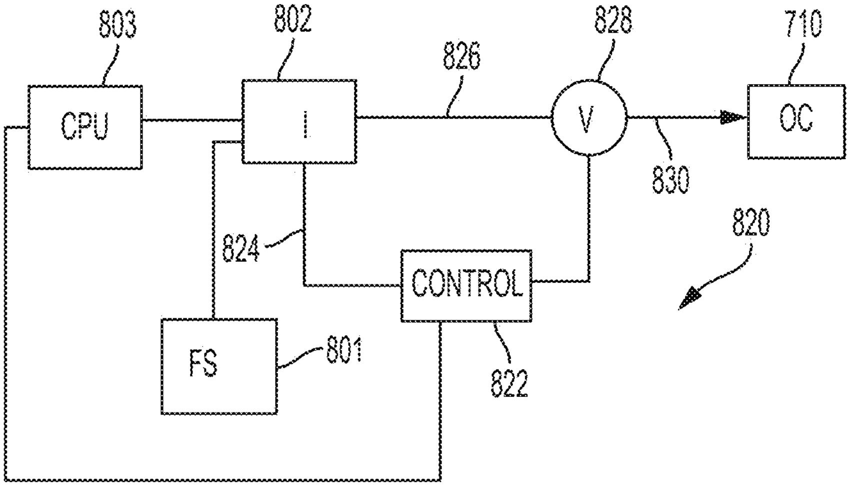
FIG. 22 is a diagrammatic rendering of a fourth preferred pressure regulation for controlling the occlusion balloon of any of the occlusion catheter system of the first, second and third preferred embodiments of FIGS. 1-18.
Figure 24:
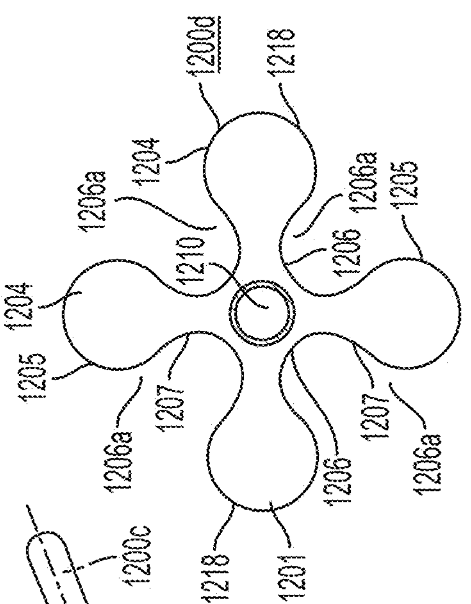
FIG. 24 is a rear elevational view of the occlusion perfusion balloon system of FIG. 23.
Figure 23:
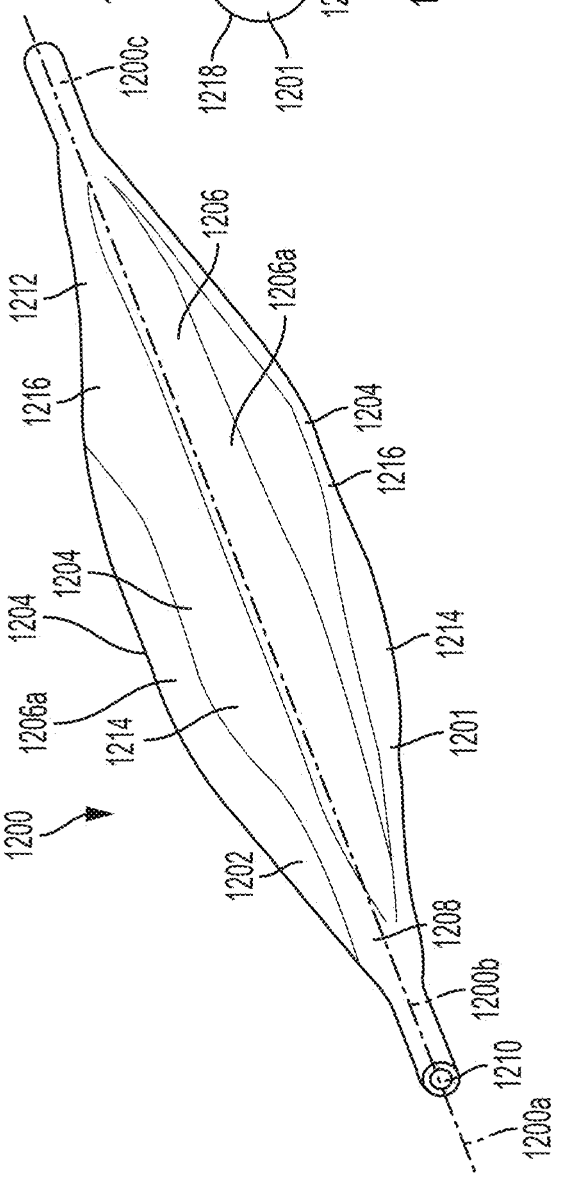
FIG. 23 is a top perspective view of a first preferred embodiment of an alternative occlusion perfusion balloon system that may be utilized with any of the occlusion catheter systems of the first, second and third preferred embodiments of the occlusion catheter system of FIGS. 1-18, wherein the occlusion perfusion balloon is in a minimal inflation configuration.
Figure 25:
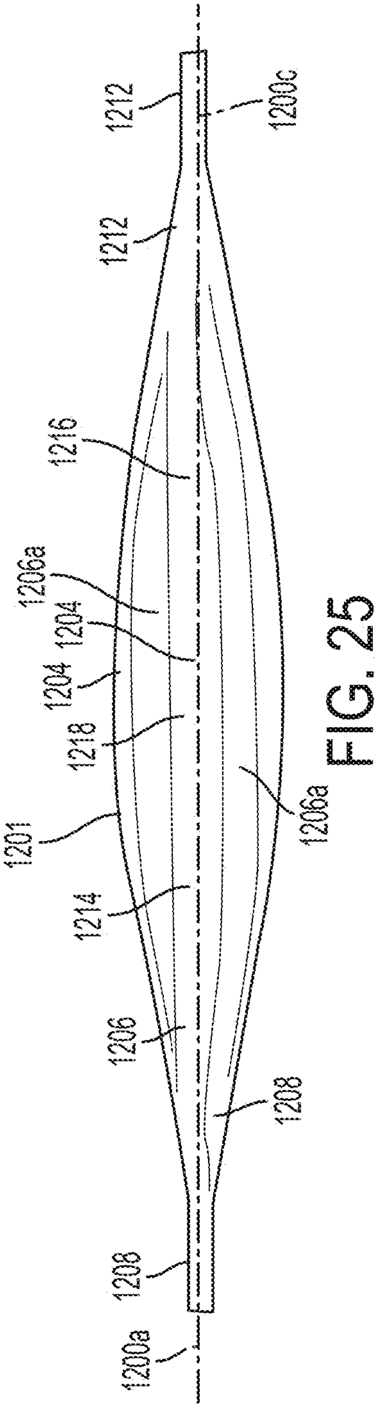
FIG. 25 is a top plan view of the occlusion perfusion balloon system of FIG. 23.
Figure 26:
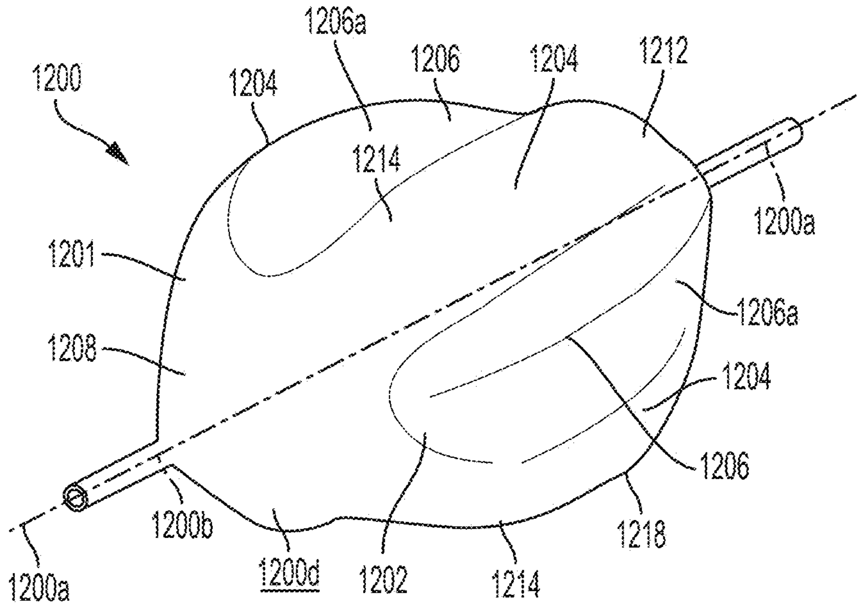
FIG. 26 is a top perspective view of the occlusion perfusion balloon system of FIG. 23, wherein the occlusion perfusion balloon is in a low inflation volume configuration.

Referring to FIG. 21, there is shown yet another alternative or third preferred embodiment of an occlusion control system 800. Unlike the occlusion control system 751 of the second preferred embodiment, the preferred occlusion control system 800 preferably has a single pressure conduit communicating between the occlusion catheter 710, which is utilized herein as a generic occlusion catheter 710, and a pressure source ("I") 752, which, in the case of a fluid, is coupled to a fluid source ("FS") 801. Similar to the occlusion control system 700 of the first preferred embodiment, the pressure source ("I") 802 of the third preferred embodiment may be under manual control, under automatic control of a computer processor 803, or under manual control interfacing with the computer processor ("CPU") 803. A pressure conduit 804 preferably provides fluid communication between the pressure source 802 and the occlusion catheter 710. A check valve 806 is preferably in-line with the pressure conduit 804. The check valve 806 may be any type of manual or automatically actuatable valves that operate both to prevent back-flow of an inflation fluid and as a pressure relief if there is an overpressure in the occlusion catheter 710. A fluid conduit 866 leads from the check valve 806 to the occlusion catheter 710. A pressure sensor 808 may be interposed within the fluid conduit 804, 866 to monitor pressure during operation of the occlusion control system 800. The pressure sensor 808 may be a pressure gauge that provides visual signal to the medical practitioner directly or may output a pressure signal to computer control 803 that controls the occlusion control system 800, in turn, upon the pressure signal and/or displays pressure data to the medical practitioner. An additional feature of the occlusion control system 800 may be the addition of a timer 810. The timer 810 is preferably incorporated into the computer processor 803 or may be positioned in-line with the fluid conduit 804, 866. The timer 810 preferably communicates a time signal to the check valve 806, to the computer control 803 and/or to the pressure source 802, as indicated by dashed lines in FIG. 21. The time signal may be a regular, consistent signal representative of the timer status, or may be a single time elapse signal that activates the check valve 806, the pressure source 802 and/or the CPU 803 to withdraw pressure communicated to the occlusion catheter 710. Similarly, the timer 810 may issue a series of time signals according to a pre-programmed routine stored in the CPU 803 or in the timer 810 itself, to control cycling of the pressure source 802 and/or opening and closing cycles of the check valve 806.

In a fourth preferred embodiment of the occlusion control system 820, the pressure source 802 is again in communication with the occlusion catheter 710 via a pressure conduit 826. An actuable valve 828 is preferably in-line in the pressure conduit 826 and operates under the influence of a controller 822. The controller 822 is preferably operably coupled, such as by electrical, mechanical or electromechanical coupling, to both the actuable valve 828 and to the pressure source 802. The controller 822 may also communicate with a computer control or CPU 803. In this preferred embodiment, the actuable valve 828 is operable under the control of the controller 822 to open or close to allow pressure from the pressure source 802 to be applied to the occlusion catheter 710 or to withdraw pressure from the occlusion catheter 710, depending upon the pressure state at the occlusion member 740 of the preferred occlusion catheter 710. Again, similar to the above-described embodiments the pressure source 802 is operable to increase pressure or decrease pressure applied to the occlusion catheter 710, such as by drawing fluid from fluid source 801 and supplying the fluid to the occlusion catheter 710 to inflate the occlusion balloon 740. In the reverse, the pressure source 802 is operable to decrease pressure by drawing fluid from the occlusion balloon 740, thereby deflating the occlusion balloon 740, releasing apposition and occlusion at the vascular wall and permitting perfusion past the occlusion member 740 when the occlusion member 740 is positioned in the vessel.

Pressure sensors 764, 808 may be positioned external the occlusion catheter 710, as shown in the second and third preferred embodiments of FIGS. 20 and 21, or may be incorporated in the occlusion catheter 710 itself and be positioned distal the occlusion member 740 with either an electrical connection at the proximal hub 790, may be wireless or may be comprised of pressure sensors positioned both distal and proximate relative to the occlusion member 740 and external relative to the occlusion catheter 710 to sense pressure both distal relative to the occlusion member 740, proximal the occlusion member 740, within the occlusion member 740 and within the pressure line 804, 866, 826, 766 proximal the occlusion member 740.

In each of the foregoing described preferred embodiments of the occlusion control systems 700, 751, 800, 820 depicted and described with reference to FIGS. 19-22, the systems may also include sensors, transmitters, receivers, interrogators or other means for measuring physical and/or physiological parameters distal and/or proximal one or more of the expandable occlusion members, including, for example blood pressure sensors, heart rate sensors, flow sensors, chemical sensors, temperature sensors, oxygenation sensors, ischemia sensors, biological sensors, imaging sensors or the like.

Occlusion/Perfusion Systems

The preferred occlusion control systems 700, 751, 800, 820 described above function to control the apposition of the occlusion member 140, 540, 740 against the vascular wall of the patient's vessel by regulating the pressure applied to the occlusion member 140, 540, 740. These preferred systems 700, 751, 800, 820 regulate and mitigate both hypertension and hypotension, by controlling the relative degree of occlusion and perfusion, such as during and after a vascular repair procedure. The occlusion catheter system 100, 300, 500, 700, itself, can also be configured to regulate the degree of occlusion and perfusion. Referring to FIGS. 23-34, there are provided alternative preferred occlusion balloon geometries that at least partially occlude the vascular lumen of the patient's vessel, thereby permitting at least a partial perfusion flow of blood past the occlusion site, if desired by the physician or medical technician performing a procedure with the preferred systems.

Figure 27:
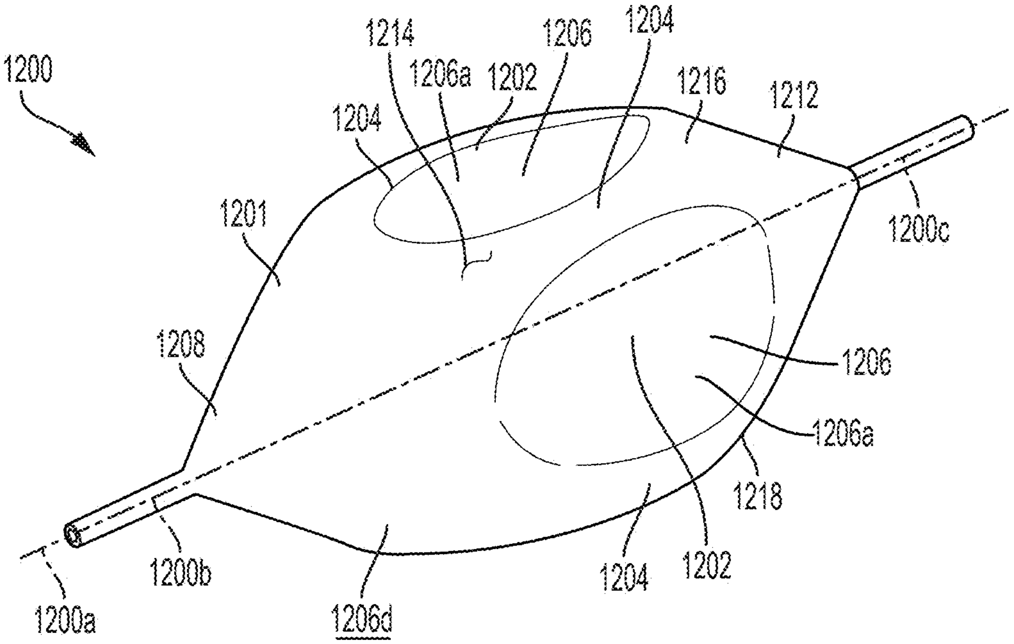
FIG. 27 is a top perspective view occlusion perfusion balloon system of FIG. 23, wherein the occlusion perfusion balloon is in a medium inflation configuration.
Figure 28:
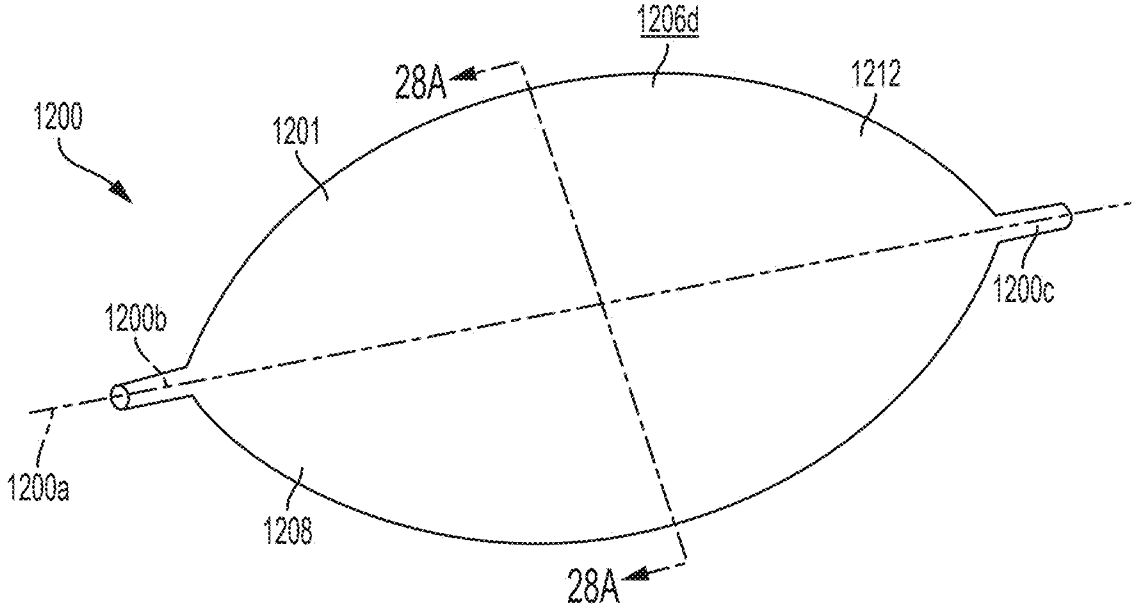
FIG. 28 is a top perspective view of the occlusion perfusion balloon system of FIG. 23, wherein the occlusion perfusion balloon is in a full inflation configuration.
Figure 28A:
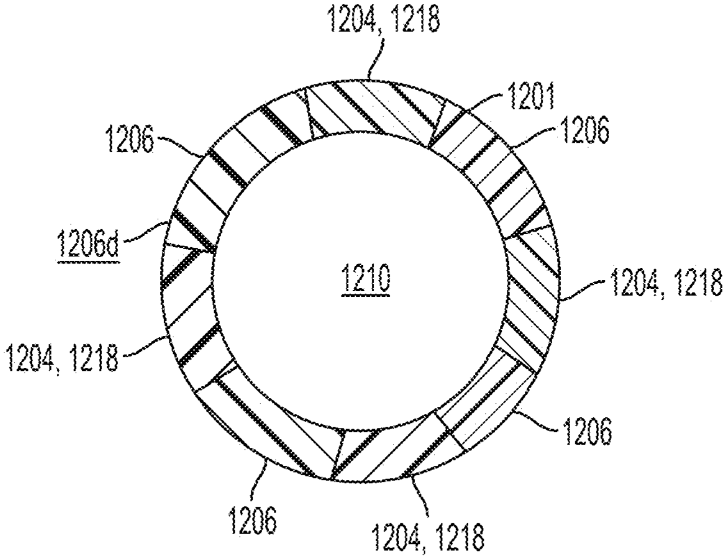
FIG. 28A is a cross-sectional view of the occlusion perfusion balloon system of FIG. 23, taken along line 28A-28A of FIG. 28.
Figure 29B:
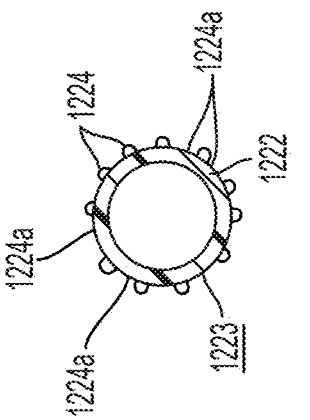
FIG. 29B is a cross-sectional view taken along line 29B-29B of FIG. 29A.
Figure 30B:
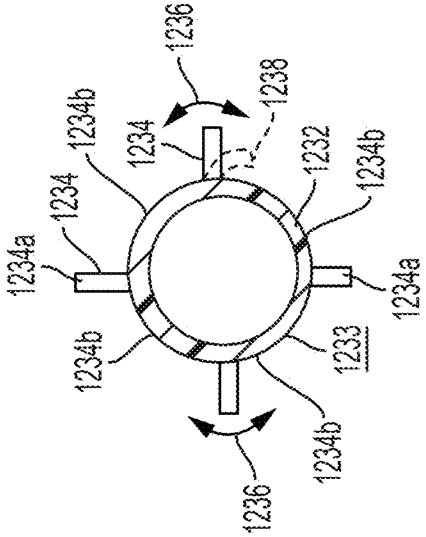
FIG. 30B is a cross-sectional view taken along line 30B-30B of FIG. 30A.
Figure 29A:
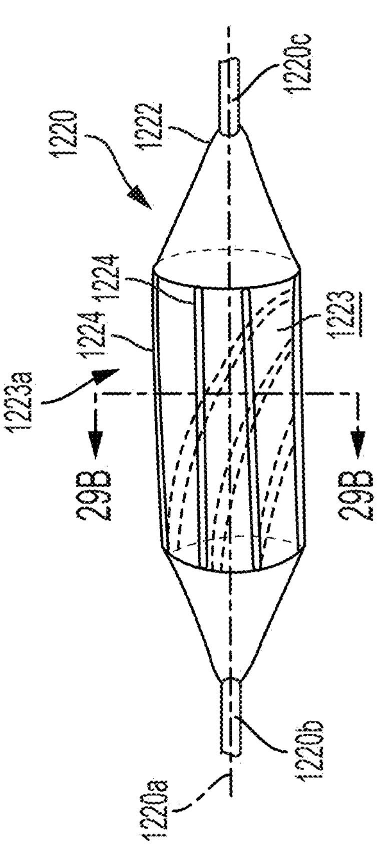
FIG. 29A is side perspective view of a second preferred embodiment of an alternative occlusion perfusion balloon system that may be utilized with any of the occlusion catheter systems of the preferred embodiments described herein, wherein the occlusion perfusion balloon is in an inflated configuration.
Figure 30A:
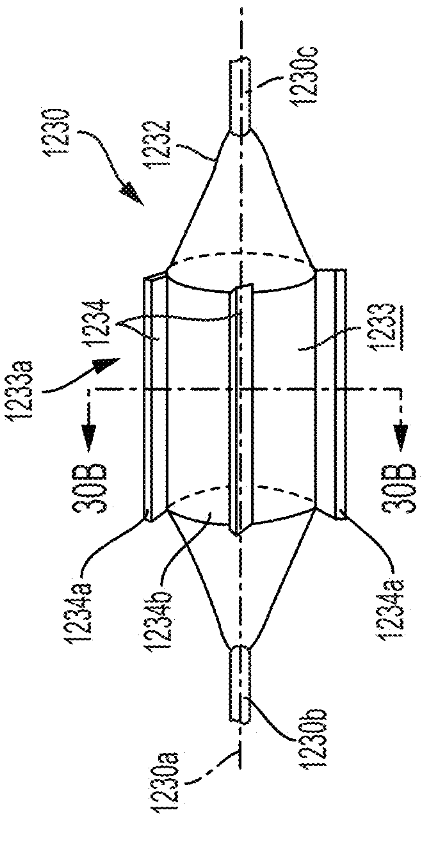
FIG. 30A is a side perspective view of a third preferred embodiment of an alternative occlusion perfusion balloon system that may be utilized with any of the occlusion catheter systems of the preferred embodiments of the occlusion catheter system described herein, wherein the occlusion perfusion balloon is in an inflated configuration.
Figure 31:
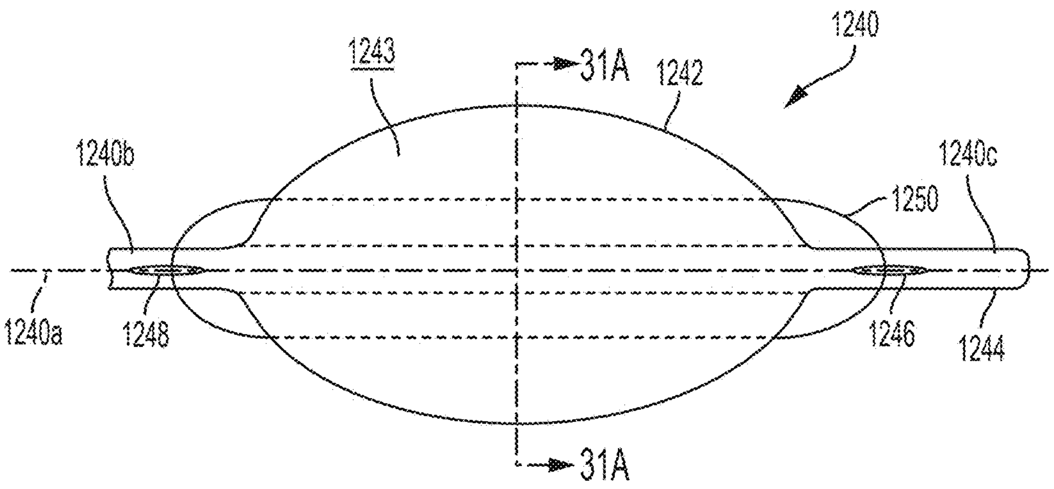
FIG. 31 is a side elevational view of fourth and fifth preferred embodiments of an alternative occlusion perfusion balloon system that may be utilized with any of the occlusion catheter systems of the preferred embodiments of the occlusion catheter systems described herein, wherein the occlusion perfusion balloon is in an inflated configuration.
Figure 31A:
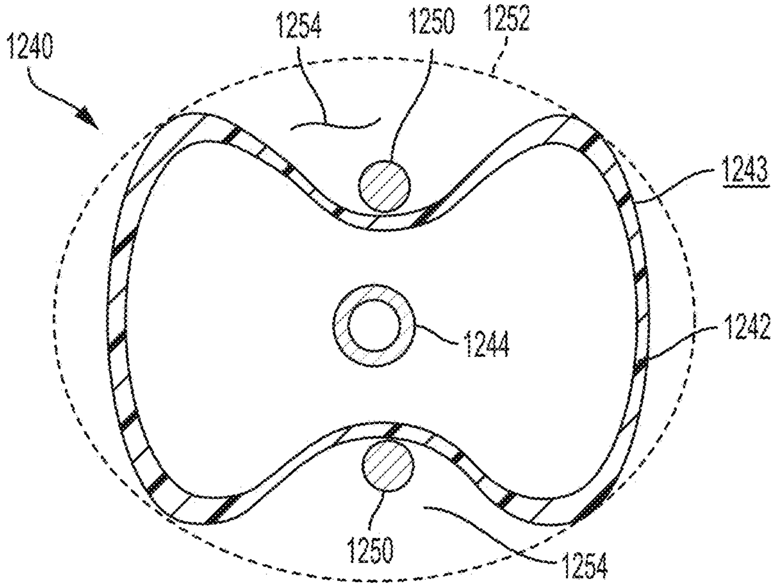
FIG. 31A is a cross-sectional view of the occlusion perfusion balloon system of FIG. 31, taken along line 31A-31A of FIG. 31 in accordance with the fourth preferred embodiment.
Figure 31B:
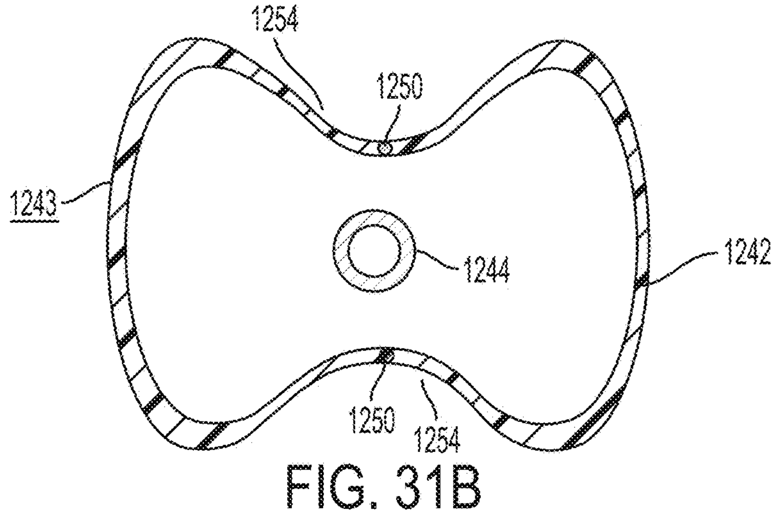
FIG. 31B is a cross-sectional view of the occlusion perfusion balloon system of FIG. 31, taken along line 31A-31A of FIG. 31, wherein a restraining filament is incorporated into the occlusion perfusion balloon in accordance with the fifth preferred embodiment.
Figure 32:
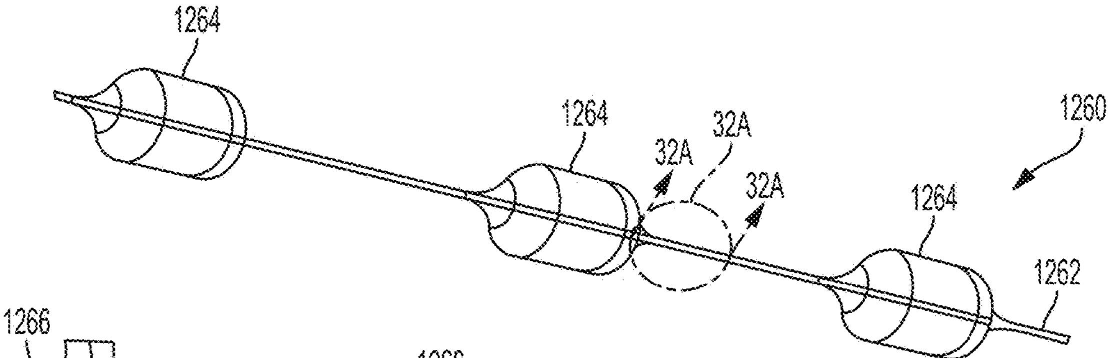
FIG. 32 is a top perspective view of a sixth preferred embodiment of an occlusion perfusion balloon system comprised of an occlusion perfusion balloon assembly that may be utilized with any of the preferred occlusion catheter systems described herein, wherein the occlusion perfusion balloon assembly is in an inflated configuration.
Figure 32A:
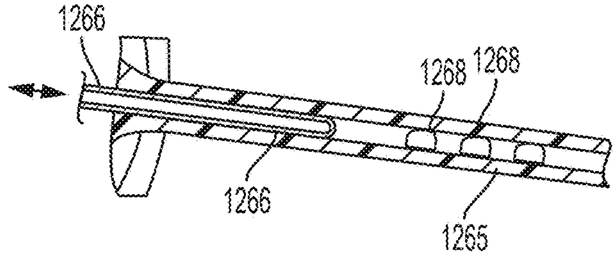
FIG. 32A is a cross-sectional view of the occlusion perfusion balloon system of FIG. 32, taken along line 32A-32A of FIG. 32.
Figure 33:
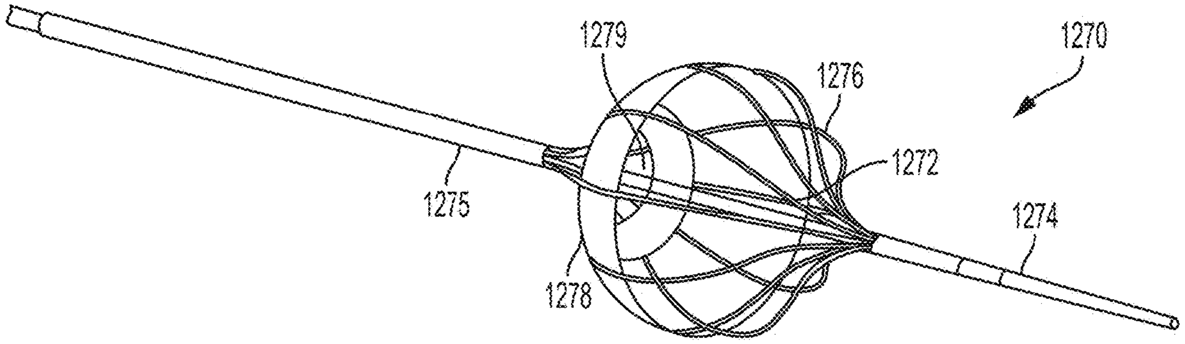
FIG. 33 is a top perspective view of a seventh preferred embodiment of an occlusion perfusion balloon system that may be utilized with any of the preferred occlusion catheter systems described herein, wherein the occlusion perfusion balloon is in an inflated configuration.
Figure 34:
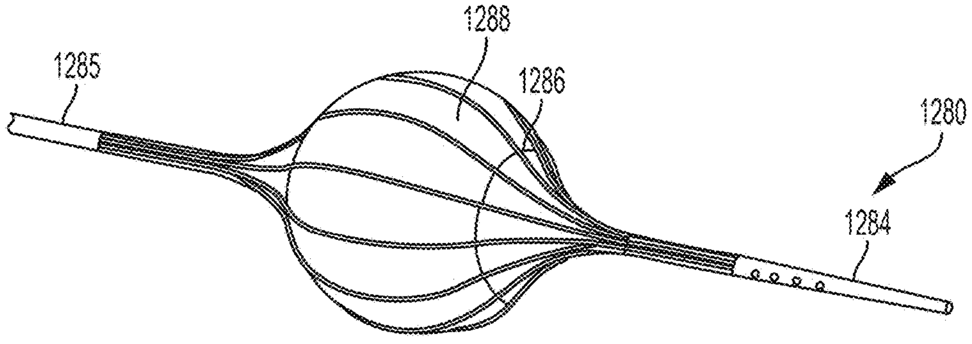
FIG. 34 is a top perspective view of a eighth preferred embodiment of an occlusion perfusion balloon system that may be utilized with any of the preferred occlusion catheter systems of described herein, wherein the occlusion perfusion balloon is in an inflated configuration.
Figure 35A:
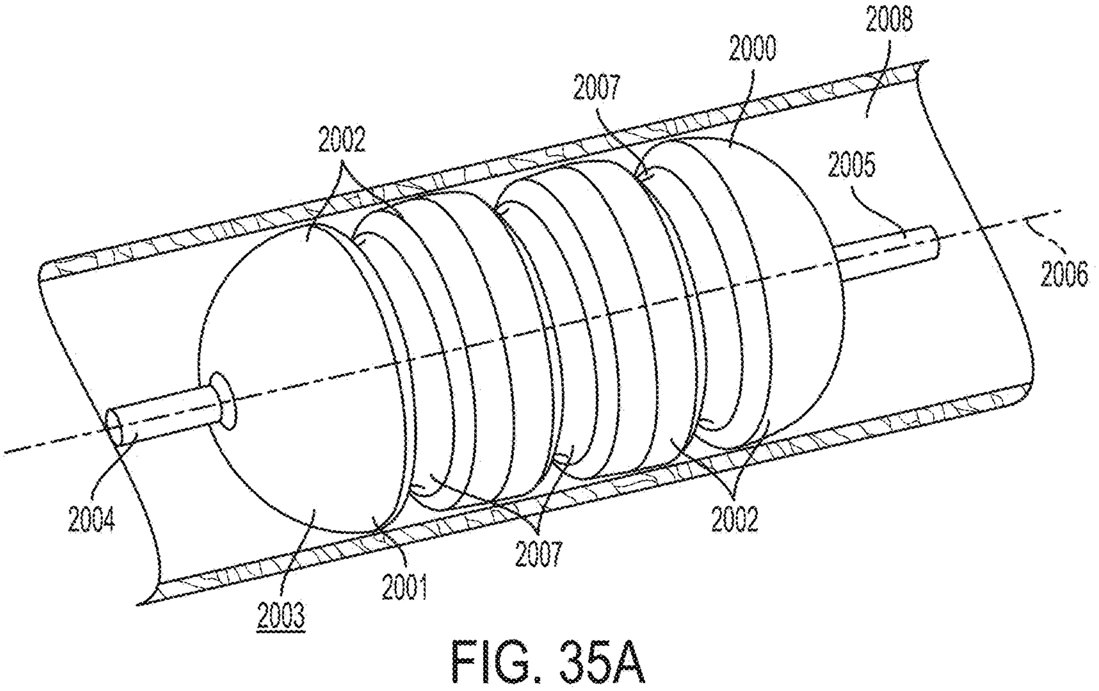
FIG. 35A is a side perspective view of a ninth preferred embodiment of an occlusion/perfusion balloon system that may be utilized with any of the occlusion catheter systems described herein, wherein the occlusion/perfusion balloon is in a partially inflated configuration within a vessel.
Figure 35B:
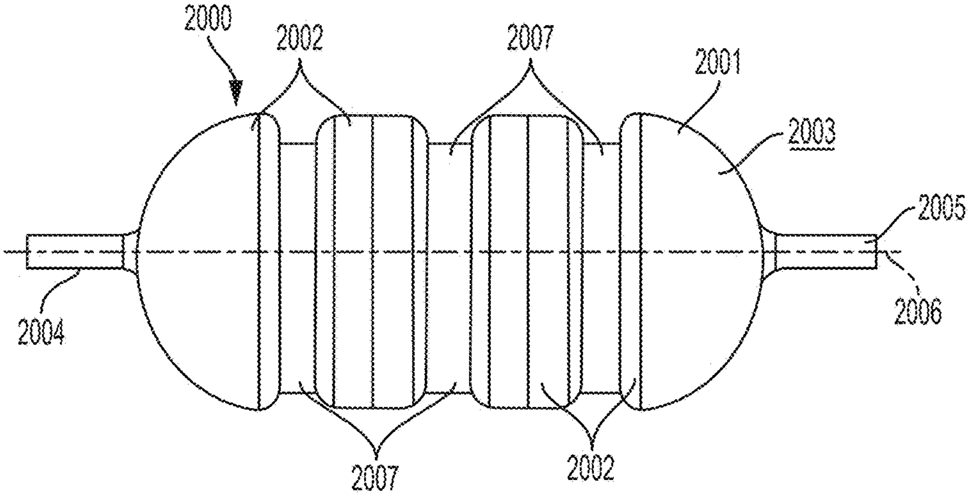
FIG. 35B is a side elevational view of the occlusion/perfusion balloon system of FIG. 35A, wherein the balloon is in the partially inflated configuration.
Figure 35C:
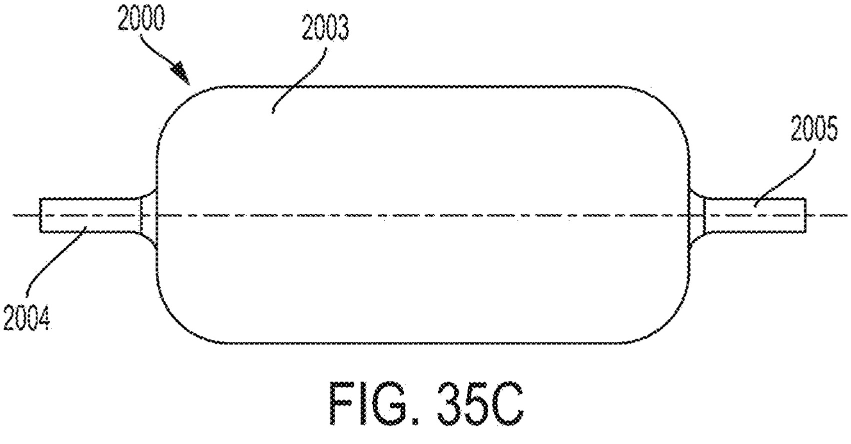
FIG. 35C is a side elevational view of the occlusion/perfusion balloon system of FIG. 35A, wherein the balloon is in a fully inflated configuration.
Figure 35D:
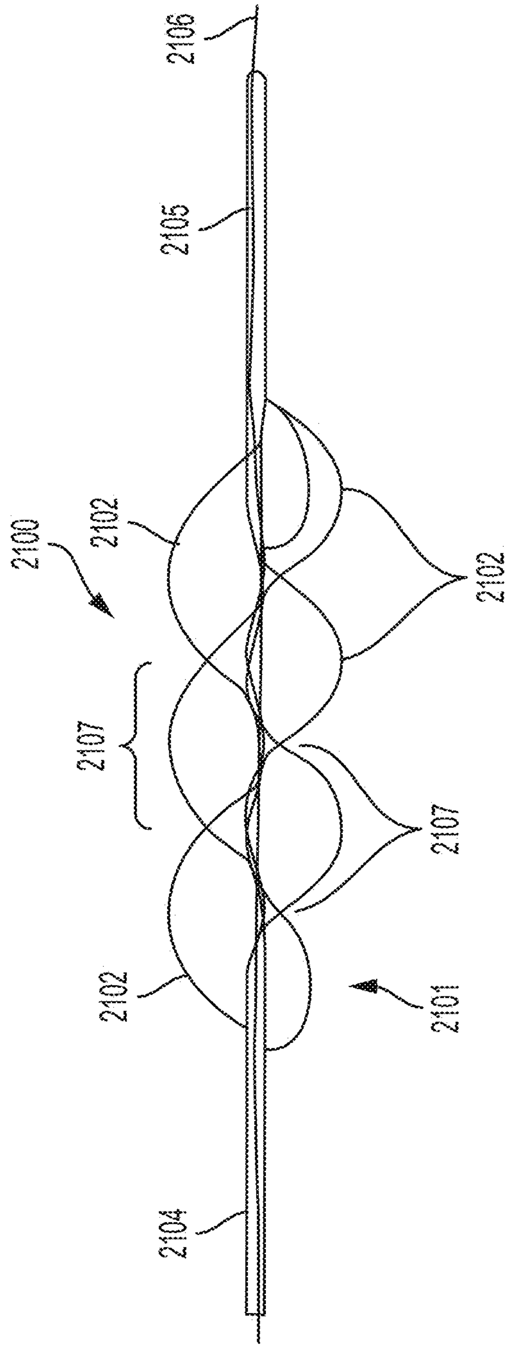
FIG. 35D is a side perspective view of an occlusion/perfusion balloon system in accordance with a tenth preferred embodiment that may be utilized with any of the occlusion catheter systems described herein.

A first preferred embodiment of the occlusion/perfusion balloon system 1200 is depicted in FIGS. 23-28A, a second preferred embodiment of the occlusion/perfusion balloon 1220 is depicted in FIGS. 29A and 29B, a third preferred embodiment of the occlusion/perfusion balloon 1230 is depicted in FIGS. 30A and 30B, a fourth and fifth preferred embodiment of the occlusion/perfusion balloon system 1240 is depicted in FIGS. 31-31B, a sixth preferred embodiment of an occlusion/perfusion balloon system 1260 is depicted in FIGS. 32 and 32A, a seventh preferred embodiment of the occlusion/perfusion balloon system 1270 is depicted in FIG. 33, an eighth preferred embodiment of the occlusion/perfusion balloon system 1280 is depicted in FIG. 34, a ninth preferred embodiment of the occlusion/perfusion balloon system 2000 is depicted in FIGS. 35A and 35B and a tenth preferred embodiment of the occlusion/perfusion balloon system 2100 is depicted in FIG. 35D.

Referring to FIGS. 23-28A, a balloon 1201 of the occlusion/perfusion balloon system 1200 of the first preferred embodiment is fabricated of a substantially compliant biocompatible material, which may be a polymer, metal or composite material. The balloon 1201 of the occlusion/perfusion balloon system 1200 may alternatively be constructed of a substantially non-compliant material such that the balloon has a substantially defined shape in a fully inflated configuration that facilitates at least partial flow of fluid through channels 1206*a*. The term "substantially non-compliant" is intended to mean a compliance range of about zero to fifteen percent (0-15%) of its expanded diameter when inflated to its rated pressure. The balloon 1201 of the occlusion/perfusion balloon 1200 is preferably constructed of polymeric balloon materials, including, but not limited to, polyethylene terephthalate ("PET"), nylon, polyethylene, polyether block amides, such as PEBAX, polyurethane and polyvinyl chloride. Highly compliant polymer materials may be made substantially non-compliant by incorporation of composite materials, such as carbon fibers or other substantially non-elastic materials, into or on the polymer material of the preferred balloon 1201. Similarly, a compliant balloon material may be constrained by a substantially non-compliant material, including polymer, metal or composite.

While the first preferred balloon 1201 is depicted in the accompanying figures in an elliptical-shape, it may have a different geometric shape than elliptical, including, without limitation, spherical, elliptical, conical, square, rectangular, dog-boned, tapered, stepped, or combinations thereof, such as, for example, conical/square or conical/spherical.

The first preferred occlusion/perfusion balloon system 1200 has a plurality of radially projecting members 1204 on the balloon 1201 when the occlusion/perfusion balloon system 1200 is in a partially-inflated to nearly fully-inflated configuration. The projecting members 1204 preferably project outwardly relative to a central longitudinal axis 1200*a* of the balloon 1201. Landing areas 1206 and channels 1206*a* are preferably defined between adjacent pairs of the projecting members 1204 when the balloon 1201 is partially-inflated to nearly fully-inflated. The balloon 1201 has a proximal end 1208 and a distal end 1212 that engage with and are joined to a proximal catheter member 1200*b* and a distal catheter member 1200*c*. The proximal catheter member 1200*b* includes an inflation lumen 1210 therein that facilitates inflation of the balloon. The balloon 1201 may be utilized with any of the preferred occlusion catheter systems 100, 300, 500, 700, 800, 1300, 1350 described herein by mounting the proximal and distal ends 1208, 1212 to the associated catheters. The first preferred balloon 1201 defines an open envelope within the balloon 1201, which receives an inflation fluid or gas to expand the balloon 1201 from a collapsed configuration (not shown), wherein the balloon 1201 is folded to have substantially the same diameter as the proximal and/or distal catheters 1200*b*, 1200*c* for introduction into a patient's vessel, to its fully expanded state or inflated configuration (FIGS. 28 and 28A). In the inflated configuration, the projecting members 1204 and landing areas 1206 are nearly, visually imperceptible from each other, as the balloon 1201 has a substantially smooth, continuous outer surface shape in the inflated configuration. In contrast, in partially inflated configurations (FIGS. 23-27), the projecting members 1204 and the landing areas 1206 or channels 1206*a* are visually identifiable with the projecting members 1204 typically positioned further from the central longitudinal axis 1200*a* than the associated landing areas 1206, with the channels 1206*a* defined in the spaces between the projecting members 1204.

In this first preferred embodiment of the occlusion/perfusion balloon system 1200, the channels 1206*a* of the balloon 1201 permit flow of fluid and blood past the balloon 1201, substantially parallel or along the longitudinal axis 1200*a* when the system 1200 is inserted into a patient's vessel. The balloon 1201 of the first preferred occlusion/perfusion system 1200 may take on numerous shapes, each with channels 1206*a* depending on the level of inflation. For example, in a minimal inflation configuration (FIGS. 23-25), the balloon 1201 has relatively deep and large channels

1206*a* to accommodate relatively significant blood and fluid flow, in a low inflation configuration (FIG. 26), the balloon 1201 has comparatively smaller channels 1206*a*, in a medium inflation configuration (FIG. 27), the balloon 1201 has again comparatively smaller channels 1206*a* and, in a full inflation configuration (FIG. 28), the balloon 1201 does not include perceptible channels, such that the vessel may be completely occluded when the balloon 1201 is inflated to the fully inflated configuration.

The plurality of radially projecting members 1204 and landing areas 1206 preferably extend along or substantially parallel to the central longitudinal axis 1200*a* of the balloon 1201. The radially projecting members 1204 may be oriented substantially parallel to the longitudinal axis 1200*a* of the balloon 1201 or may extend at an angle relative to the longitudinal axis 1200*a* of the balloon system 1201. For example, the projecting members 1204 may spiral in a curved manner along an outside surface 1200*d* of the balloon 1201, such that the channels 1206*a* extend in a substantially spiral or arcuate orientation relative to the longitudinal axis 1200*a*. The angular orientation of the projecting members 1204 and landing areas 1206 are preferably sufficient to channel blood or fluid flow along the length of the balloon 1201 within the vessel and to generally not impede flow or contribute substantially to highly disrupted blood flow that may result in thrombose. A preferred angular offset of the projecting members 1204 and landing areas 1206 may be between zero and forty-five degrees (0-45°) relative to the longitudinal axis 1200*a* the balloon 1201. The radially projecting members 1204 may have either a generally linearly extending orientation, as is shown in the first preferred embodiment, a curvilinear orientation or nearly any other orientation that permits formation of the landing areas 1206 between the projecting members 1206 such that blood and fluid may flow through the landing areas 1206 when the balloon 1201 is inserted in the vessel and is at least partially inflated.

In the first preferred embodiment, the occlusion/perfusion balloon system 1200 includes four (4) regularly arrayed radially projecting members 1204 on or incorporated into the balloon 1201. The balloon 1201 is not limited to including four (4) regularly arrayed radially projecting members 1204 and associated landing areas 1206 and the number of radially projecting members 1204 may be any number greater than two (2) that permit blood and fluid to flow through the landing areas 1206 when the balloon 1201 is in one of its partially inflated configuration. In the first preferred embodiment, there is sufficient surface area on the radially projecting members 1204 to seat in apposition with a vascular wall surface of the patient's vessel and that there is sufficient surface area in the landing areas 1206 to channel fluid or blood flow along a length of the balloon 1201 when the balloon 1201 is in one of its partially inflated configurations, such as the partially inflated configurations of FIGS. 23-27.

In the first preferred embodiment of the occlusion/perfusion balloon system 1200, each of the plurality of radially projecting members 1204 has a generally circular or arcuate transverse profile, as depicted in FIG. 27, on an upper aspect 1205 thereof, and a stem portion 1207 that extends from the landing area 1206. The stem portion 1207 connects with the upper aspect 1205 of each radially projecting member 1204 such that the stem portions 1207 have a smaller stem width than an upper aspect width (See FIG. 24). In the first preferred embodiment, the projecting members 1204 each have an apex 1218 that is preferably located intermediate a length of each radially projecting member 1204 or centrally between the proximal end 1208 and distal end 1212 of the preferred balloon 1201. The projecting members 1204 of the first preferred embodiment also preferably include a proximal, generally flattened or planar area 1214 and a distal, generally flattened or planar area 1216 on an outermost surface of each radially projecting member 1204 relative to the central longitudinal axis 1200*a*. The proximal and distal generally flattened or planar areas 1214, 1216 preferably extend proximally and distally, respectively, from the apexes 1218. As will be seen from the series of FIGS. 23-28, representing a sequence of the balloon 1201 of the first preferred occlusion/perfusion balloon system 1200 with increasing degrees of inflation, the apex 1218 forms the outermost equatorial circumference at the longitudinal midpoint of the balloon 1201 along the longitudinal axis 1200*a*. The proximal and distal generally flattened or planar areas 1214, 1216 facilitate diametric expansion and transition to the preferred fully elliptical-like shape of the fully expanded balloon 1201 in its full inflation configuration (See FIG. 28).

The first preferred embodiment of the occlusion/perfusion balloon system 1200 may be constructed by forming the balloon 1201 of two or more materials having differing hardness or moduli of elasticity. In the first preferred embodiment, as depicted in FIG. 28A, the balloon 1201 may be formed such that the plurality of projecting members 1204 are made of a higher durometer material, while the landing areas 1206 are made of a relatively lower durometer material. These materials may be co-extruded or molded to define the preferred balloon 1201. In addition, the occlusion/perfusion balloon 1201 may be alternatively designed and configured with different materials that are able to take on the general size and shape of the occlusion/perfusion balloon 1201, particularly the minimal inflation, low inflation, medium inflation and full inflation configurations and related inflation configurations between these configurations shown in the drawings, and withstand the normal operating conditions of the occlusion/perfusion balloon 1201.

The size, shape and configuration of the plurality of projecting members 1204 of the first preferred balloon 1201 is but one exemplary embodiment and may take on other various sizes, shapes and configurations. As described above, the plurality of projecting members 1204 are preferably an integral part of the balloon 1201 itself, and form the wall surfaces of the balloon 1201. Alternatively, the projecting members 1204 may be elongate filaments, tubes, cylinders or other members that are either joined to or integrally formed with an outer wall surface of the occlusion/perfusion balloon 1201. For example, the projecting members 1204 may be constructed of a high durometer polytetrafluoroethylene (PTFE), fluorinated ethylene propylene (FEP), polyether block amide (PBAX) or other similar biocompatible material, formed in solid or tubular members having a circular, elliptical, quadrilateral, polygonal or other suitable transverse cross-sectional shape. These alternative projecting members 1204 may also be separately connected to the balloon 1201 and separately inflatable and deflatable to control the inflation configuration of the occlusion/perfusion balloon 1201. The preferred projecting members 1204 may be configured in nearly any shape, size and configuration such that the occlusion/perfusion balloon 1201 is able to selectively permit flow of fluid and blood past the projecting members 1204, at least in certain inflation configurations, along the longitudinal axis 1200*a*. In addition, the occlusion/perfusion balloon 1201 may be configured such that the channels 1206 are comprised of flow channels or holes (not shown) that are surrounded by the material of the occlusion/perfusion balloon 1201 to permit flow of blood and fluid through or around the occlusion/perfusion balloon 1201 generally parallel or along the longitudinal axis 1200*a*.

Referring to FIGS. 29A and 29B, an occlusion balloon system 1220 in accordance with a second preferred embodiment includes a balloon 1222 with a plurality of projecting members 1224 projecting from an outer wall surface 1223 of the balloon 1222. The balloon 1222 is connected to a proximal catheter member 1220*b* and a distal catheter member 1220*c*, which may be incorporated into any of the preferred occlusion catheter systems 100, 300, 500, 700, 1700, 1800, described herein. The proximal catheter member 1220*b* includes an inflation lumen therein that facilitates inflation of the balloon 1222. The projecting members 1224 preferably extend substantially radially away from the outer surface 1223 of the balloon 1222 and extend along the outer surface 1223 substantially longitudinally relative to the longitudinal axis 1220*a*. The preferred projecting members 1224 preferably extend along an entire length of a substantially tubular section 1223*a* of the balloon 1222, which tapers to the proximal and distal catheters 1220*b*, 1220*c* in a substantially funnel-shape at its ends. The outer surface 1223 of the balloon 1222 preferably has a constant diameter in the tubular section 1223*a*. The projecting members 1224 are not limited to extending substantially longitudinally along the entire length of the tubular section 1223*a* and the tubular section 1223*a* is not limited to having a substantially constant diameter and the balloon 1222 may be otherwise designed and configured such that the balloon 1222 is able to partially and fully occlude a vessel and withstand the normal operating conditions of the preferred occlusion balloon system 1220.

The projecting members 1224 preferably define channels 1224*a* between the projecting members 1224 or adjacent the projecting members 1224 that permit flow of blood and fluid substantially parallel to the longitudinal axis 1220*a* when the occlusion balloon system 1220 is positioned within a vessel. The balloon of the system 1220 may be inflated to various levels to enhance or reduce the channels 1224*a*, depending on the preferred procedure, preferences of the medical technician or conditions encountered or detected within the vessel.

Referring to FIGS. 30A and 30B, an occlusion/perfusion balloon system 1230 in accordance with a third preferred embodiment includes a balloon 1232 and a plurality of vanes 1234 that project from an outer wall surface 1233 of the balloon 1232. In this third preferred embodiment of the occlusion/perfusion balloon system 1230, the vanes 1234 are preferably resilient in nature and are capable of deforming or folding over against an outer wall surface 1233 of the balloon 1232, as depicted by phantom lines 1238 (FIG. 30B), when the balloon 1232 is in apposition against a vascular wall surface and occluding the vessel or partially occluding the vessel. The vanes 1234 of the third preferred embodiment also preferably extend substantially radially away from the outer surface 1233 and extend along the outer surface 1233 substantially longitudinally relative to the longitudinal axis 1230*a*. The vanes 1234 preferably extend along an entire length of a substantially tubular section 1233*a*, which tapers to the proximal and distal catheters 1230*b*, 1230*c*. The proximal catheter 1230*b* includes an inflation lumen therein that facilitates inflation and deflation of the balloon 1232. The outer surface 1233 preferably has a constant diameter in the tubular section 1233*a*. The vanes 1234 preferably extend to tips 1234*a* that are spaced at a greater distance from the outer surface 1233 when compared to the similar projecting members 1224 of the second preferred embodiment. The outer surface 1233 of the balloon 1232 preferably has a constant diameter in the tubular section 1233*a*. The projecting members 1234 are not limited to extending substantially longitudinally along the entire length of the tubular section 1233*a* and the tubular section 1233*a* is not limited to having a substantially constant diameter and the balloon 1232 may be otherwise designed and configured such that the balloon 1232 is able to partially and fully occlude a vessel and withstand the normal operating conditions of the preferred occlusion balloon system 1220.

In this third preferred embodiment of the system 1230, the vanes 1234 preferably define channels 1234*b* therebetween and with the walls of the vessel that permit flow of blood and fluid through the vessel along or substantially parallel to the longitudinal axis 1230*a*. The channels 1234*b* may be manipulated or controlled by the user or designer by the inflation of the balloon 1232, the stiffness of the vanes 1234, the height of the vanes 1234, the separation of the vanes 1234 and related other factors that may increase or decrease the size of the channels 1234*b* that facilitate flow of fluid through the vessel when the balloon 1232 is inflated.

Referring to FIGS. 31-31B, fourth and fifth preferred embodiments of the occlusion/perfusion system 1240 includes a compliant occlusion balloon 1242 and at least one restraining filament 1250 connected to proximal and distal catheters 1240*b*, 1240*c* with the restraining filament 1250 positioned on an outside of an outer surface 1243 of the balloon 1242. The proximal catheter 1240*b* includes an inflation lumen therein that carries fluid or gas to and from the balloon 1242 to facilitate inflation and deflation of the balloon 1242, respectively. The restraining filament 1250 deforms at least one section of the occlusion balloon 1242 radially inward toward a longitudinal axis 1240*a* of the balloon 1242 and away from the vascular wall or allows an adjacent portion of the balloon 1242 to extend further away from the longitudinal axis 1240*a* than the portion proximate the filament 1240. The inclusion of the restraining filament 1250 preferably creates a reverse curvature in the balloon 1242 and permits fluid to flow past the balloon 1242, substantially parallel to the longitudinal axis 1240*a* when the balloon 1242 is positioned within the vessel. When a desired time elapses, a desired arterial blood pressure is achieved, or when other indicators suggest, the tension on the restraining filament 1250 may be released, the reverse curvature will expand and the balloon 1242 and the balloon 1242 will return to its occlusion position in apposition with the vessel wall.

In the occlusion/perfusion system 1240 of the fourth preferred embodiment, the catheters 1240*b*, 1240*c* preferably accommodate the at least one restraining filament 1250 within the catheter 1240*b*, 1240*c*, such that the filament 1250 exits the catheter 1240*b*, 1240*c* proximate the balloon 1242, overlay the balloon 1250 along a portion of the length of the balloon 1250 and is configured to provide tension against the outer surface 1243 of the balloon 1250 to define channels or flow paths along the balloon 1250, preferably substantially parallel to or along the direction of the longitudinal axis 1240*a*. In order to accommodate this arrangement, the catheter 1240*b*, 1240*c* of the fourth preferred embodiment is provided with a distal port 1246 passing through the outer wall of the distal catheter 1240*c* and a proximal port 1248 also passing through the outer wall of the proximal catheter 1240*b*. The restraining filament 1250 is preferably lead from the proximal end of the proximal catheter 1240*b*, where it is accessible to the medical practitioner for tensioning, is passed through a lumen in the proximal catheter 1240*b* (not shown), exits the proximal port 1248, passes over the balloon 1242 and adjacent the outer surface 1243 of the balloon 1242, and anchor or is attached at the distal port 1246 to the distal catheter 1240*c*. In this manner, tensioning the at least one filament 1250 at the proximal end of the proximal catheter 1240*b* preferably causes the filament 1250 to tension against the balloon 1242 or block expansion of the balloon 1242 proximate the filament 1250. When the balloon 1242 is inflated, the portions of the balloon 1242 spaced from the filament 1250 expand away from the longitudinal axis 1240*a*, while the portions of the balloon 1242 adjacent and beneath the filament 1250 are blocked from expansion by the filament 1250. Accordingly, the outer surface 1243 of the balloon 1242 forms or defines channels 1254 extending substantially parallel to the longitudinal axis 1240*a* or along the length of the filament 1250 between the expanded portions of the balloon 1242 between the filament 1250 that permit fluid flow in the channels 1254 created between the vessel wall 1252 (shown in phantom in FIG. 31A) and the reverse curve of the outer surface 1243 of the balloon 1242.

Referring specifically to FIG. 31B, the fifth preferred occlusion/perfusion balloon system 1240 entails running the at least one restraining filament 1250 within the interior space or within the material defined by the balloon 1242 and joining the at least one filament 1250 to the inner wall surface of the balloon 1242. This joining between the at least one restraining filament 1250 and the inner wall surface of the balloon 1242 may be accomplished by adhesives, thermobonding or reflowing. Alternatively, one or more lumens may be co-extruded with the inner wall surface of the balloon 1242 or tubular members joined to the inner wall surface of the balloon 1242, and the at least restraining filament 1250 run within this at least one lumen or tubular member and anchored therein. The balloon 1242 may alternatively be formed from different materials, with the filament 1250 being constructed of a stiffer material than the remainder of the balloon 1242, such that the portion of the balloon 1242 with the filament 1240 therein does not expand at the same rate or to the same extent as the remainder of the balloon 1242. In this fifth preferred embodiment, occlusion/perfusion balloon system 1240 does not necessarily include the proximal port 1248 and the distal port 1246, as the filament 1250 may be positioned within the catheters 1240*b*, 1240*c* or within a lumen of the catheters 1240*b*, 1240*c*. The filament 1250 would, therefore, typically not be exposed to the blood vessel or blood flow in such a configuration, as the filament 1250 would be encased within the balloon 1242 and the catheters 1240*b*, 1240*c*, where the filament 1250 would not typically be exposed to fluid and blood flow during use.

Referring to FIGS. 32 and 32A, a sixth preferred embodiment of an occlusion/perfusion balloon system 1260 includes a plurality of balloons 1264 carried commonly on a catheter 1262. The plurality of balloons 1264 may be incorporated with any of the preferred occlusion catheter systems 100, 300, 500, 700, 1700, 1800, described herein. The plurality of balloons 1264 are preferably independently expandable though inflation lumens or an inflation lumen 1265 in the catheter 1262. The inflation lumen 1265 preferably communicates independently with each one of the plurality of balloons 1264. The catheter 1262 preferably includes a seal member 1266 movably mounted therein and a plurality of openings 1268 that pass through the outer wall of catheter 1262 and communicate with the fluid flow lumen 1265. The seal member 1266 is reciprocally movable within the fluid lumen 1265 and selectively occludes or opens one or more of the plurality of openings 1268 in the outer wall of the catheter 1262, thereby permitting fluid flow through the fluid flow lumen 1265 and independently or concurrently into each of the plurality of balloons 1264. In this manner, the volume and rate of fluid flow into the plurality of occluding balloons 1264 may be adjusted by the relative position of the seal member 1266 within the fluid flow lumen 1265.

Referring to FIGS. 33 and 34, a seventh preferred embodiment of an occlusion/perfusion balloon system 1270 preferably does not rely upon an occlusion balloon or upon a fluid pressure to activate an occlusion balloon. Rather, in this seventh preferred embodiment, the occlusion member consists of a supporting cage structure 1272 formed of a plurality of structural members, which may be longitudinally oriented struts 1276 that taper distally, connect to a distal catheter member 1274 and taper proximally where the struts 1276 connect to a proximal catheter member 1275. An occluding membrane 1278 is preferably coupled to the supporting cage structure and may consist of a partial covering on the supporting cage structure 1272 or may be comprised of a full covering on the supporting cage structure 1272, as illustrated in FIG. 34 with reference to occlusion/perfusion system 1280 of the eighth preferred embodiment.

The struts of the supporting cage structure 1272 are preferably, fixedly coupled at their distal ends to the distal catheter member 1274 and at their proximal end are preferably, fixedly coupled to the proximal catheter sleeve member 1275. The proximal catheter sleeve member 1275 is reciprocally movable relative to the distal catheter 1274. The relative movement of the proximal catheter sleeve member 1275 relative to the distal catheter 1274 preferably causes deformation of the supporting cage structure 1272 and allows the cage structure 1272 to diametrically expand or diametrically contract under the influence of such relative movement. Such diametric expansion preferably brings the supporting cage structure 1272 and the occluding membrane 1278 into an occlusive position within the lumen of a blood vessel, while diametric contraction preferably reduces the diametric profile of the supporting cage structure 1272 and the occluding membrane 1278, thereby allowing for fluid and blood flow past the occlusion site or past the cage structure 1272.

The supporting cage structure 1272 of the seventh and eighth preferred embodiments, like a balloon, may assume a wide variety of geometries, including, without limitation, spherical, elliptical, conical, square, rectangular, dog boned, tapered, stepped, or combinations thereof, such as, for example, conical/square or conical/spherical. The supporting cage structure 1272 and its struts 1276 may be made of any suitable biocompatible material, including polymers, metals and/or composites or combinations thereof. The biocompatible material may be an elastic, superelastic, shape memory material and is preferably able to take on the general size and shape of the cage structure 1272, perform the functions of the preferred cage structure 1272 and withstand the normal operating conditions of the cage structure 1272.

The occluding membrane 1278 preferably covers at least a portion of the supporting cage structure 1272 in order to at least partially occlude the blood vessel into which the occlusion/perfusion systems 1270, 1280 are placed. The occluding membrane 1278 may cover a proximal portion of the supporting cage 1272, a distal portion of the supporting cage 1272, the entire cage 1272, such as is shown in the eighth preferred embodiment (FIG. 34), or it may cover only portions of the cage 1272 to permit partial or partially occluded flow through the vessel. The supporting cage 1272 may facilitate pre-conditioning systems that infuse fluid into the vessel to pre-emptively and prophylactically mitigate possible ischemia during occlusion. The catheters 1272, 1275, 1284, 1285 may include infusion holes 1284*a* therein that facilitate infusion of fluid into the vessel and the infusion holes 1284 may extend along all or a portion of the longitudinal length of the catheters 1272, 1275, 1284, 1285. Furthermore, the occluding membrane 1278 may have an opening 1279 in a proximal end to allow fluid flow therethrough to facilitate partial occlusion and perfusion.

The occluding membrane 1278 is preferably constructed of a woven or non-woven biocompatible material, such as polymers, metals, composites and combinations thereof, and may be elastic, superelastic or shape memory. The occluding membrane 1278 may cover the outer surface of the supporting cage 1272, the inner surface of the supporting cage 1272, or both. The occluding membrane 1278 may be joined to the supporting cage 1278 by sutures, biocompatible adhesive, by reflow, by thermal welding, or by joining to another layer of occluding membrane 1278 on the opposing surface of the supporting cage 1272 such that the struts of the supporting cage 1278 are at least partially encapsulated by the occluding membrane 1278. Methods and materials for joining the occluding membrane 1278 to supporting cage 1272 may include adhesive bonding, fastening, clamping, co-molding and other related engagement techniques.

Referring to FIGS. 35A-35C, in a ninth preferred embodiment, an occlusion balloon system 2000 includes a balloon or inflatable occlusion member 2001 with a plurality of projecting members 2002 projecting from an outer wall surface 2003 of the balloon 2001. The balloon 2001 is connected to a proximal catheter member 2004 and a distal catheter member 2005, which may be incorporated into any of the preferred occlusion catheter systems 100, 300, 500, 700, 1700, 1800, described herein. The proximal catheter member 2004 includes an inflation lumen therein that facilitates inflation of the balloon 2001. The projecting members 2002 preferably extend substantially radially away from a central longitudinal axis 2006 of the balloon 2001 and extend along the outer surface 2003 substantially laterally or circumferentially around the longitudinal axis 2006. The preferred projecting members 2002 preferably extend around an entire circumference of the balloon 2001, but are not so limited and may extend partially around the outer surface 2003, may extend at angles relative to the longitudinal axis 2006, may be comprised of various pockets on the surface 2003 or may be otherwise configured to create spacing between a vessel 2008 and the outer surface 2003, at least when the balloon 2001 is partially inflated. The balloon 2001 of the ninth preferred embodiment includes four projecting members 2002 longitudinally spaced along the length of the balloon 2001. The end projecting members 2002 taper in an arcuate shape to connections with the proximal and distal catheters 2004, 2005. The outer surface 2003 of the balloon 1222 preferably has a constant diameter at the peaks of the projecting members 2002, but is not so limited and may have tapered or variable spacing relative to the longitudinal axis 2006. Lateral channels 2007 are preferably defined between the projecting members 2002 when the balloon 2001 is at least partially inflated and are comprised of circumferentially extending voids wherein the vessel 2008 is out of contact with the outer surface 2003 in the channels 2007. In contrast, when the balloon 2001 is fully inflated or is in an inflated configuration, the balloon 2001 expands such that the outer surface 2003 is substantially consistent and channels 2007 are not formed. In this fully inflated configuration or at least close to the fully inflated configuration, the outer surface 2003 is in direct contact with the vessel 2008 and fluid and blood flow are substantially occluded in the vessel 2008. The projecting members 2001 defined in at least the partially inflated configuration are not limited to extending substantially laterally or circumferentially around the longitudinal axis 2006 and the projecting members 2002 are not limited to having a substantially constant diameter. The balloon 2001 may be otherwise designed and configured such that the balloon 2001 is able to partially and fully occlude the vessel 2008 and withstand the normal operating conditions of the preferred occlusion balloon system 2000.

The projecting members 2002 in the partially inflated configuration of the balloon 2001 preferably permit at least partial flow of blood and fluid substantially parallel to the longitudinal axis 2006 when the occlusion balloon system 2000 is positioned within the vessel 2008. The balloon 2001 of the system 2000 may be inflated to various levels to enhance or reduce the channels 2007 and the position of the projecting members 2002 relative to the inner wall of the vessel 2008, depending on the preferred procedure, preferences of the medical technician or conditions encountered or detected within the vessel. Generally, as the pressure is increased within the balloon 2001, the projecting members 2002 come into closer positioning relative to the inner surface of the vessel 2008 and, therefore, limit flow of fluid and blood through the vessel 2008.

Referring to FIG. 35D, in a tenth preferred embodiment, an occlusion/perfusion balloon system 2100 includes a balloon or inflatable occlusion member 2101 with a spiral-shape projecting from a longitudinal axis 2106 of the tenth preferred occlusion/perfusion balloon system 2100. The inflatable occlusion/perfusion balloon 2101 includes channels 2107 defined between projecting portions 2102 of the spiral-shaped balloon 2010 that permit flow of blood past the balloon 2101 when inserted into the vessel and at least partially inflated. Similar to the ninth preferred occlusion balloon system 2000, the tenth preferred occlusion/perfusion balloon system 2100 may be fully inflated within the vessel and substantially or completely occlude the vessel. The tenth preferred occlusion/perfusion system 2100 also includes a proximal catheter 2104 and a distal catheter 2105 connected to proximal and distal balloon ends of the balloon 2101, which may be incorporated into any of the preferred occlusion catheter systems and other preferred systems having inflatable balloons or occlusion members described herein.

In each of the foregoing described embodiments of the occlusion/perfusion balloon systems depicted and described with reference to FIGS. 23-35C, the systems may also include sensors, transmitters, receivers, interrogators or other means for measuring physical and/or physiological parameters distal and/or proximal one or more of the expandable occlusion members, including, for example blood pressure sensors, heart rate sensors, flow sensors, chemical sensors, temperature sensors, oxygenation sensors, ischemia sensors, biological sensors, imaging sensors or the like. Data collection of the readings from the sensors may be utilized with a controller or processor to control inflation of the balloons or occlusion members of the preferred systems to facilitate partial flow of fluid and blood through the vessel 2008 when desired or to fully occlude the vessel 2008, as desired by the medical technician.

Pre-Conditioning Systems

Figures 36, 36A, 36B, 36C:
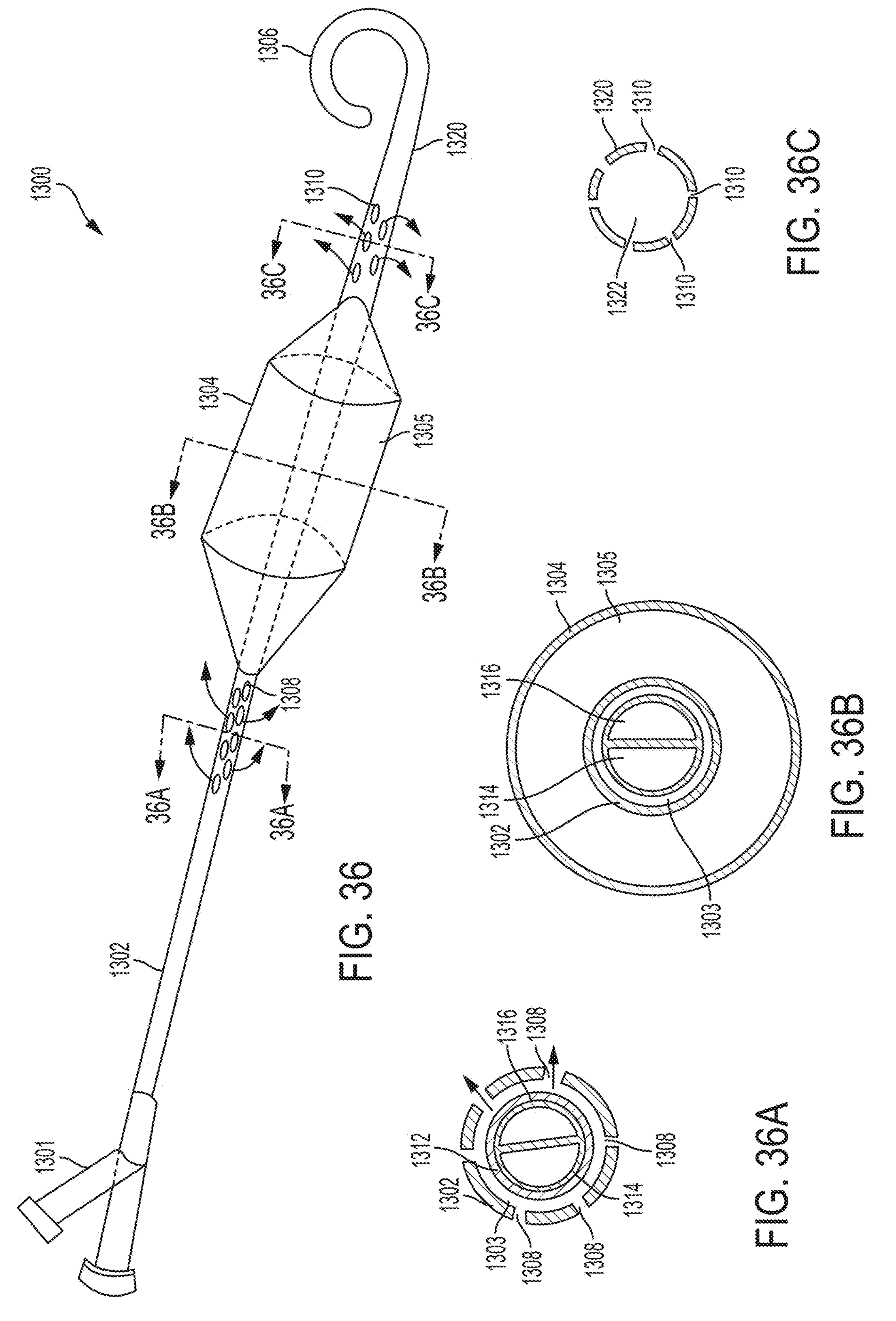
FIG. 36 is a top perspective view of an occlusion catheter system in accordance with a fourth preferred embodiment of the present invention.
FIG. 36A is a cross-sectional view of the occlusion catheter system of FIG. 36, taken along line 36A-36A of FIG. 36.
FIG. 36B is a cross-sectional view of the occlusion catheter system of FIG. 36, taken along line 36B-36B of FIG. 36.
FIG. 36C is a cross-sectional view of the occlusion catheter system of FIG. 36, taken along line 36C-36C of FIG. 36.
Figure 37:
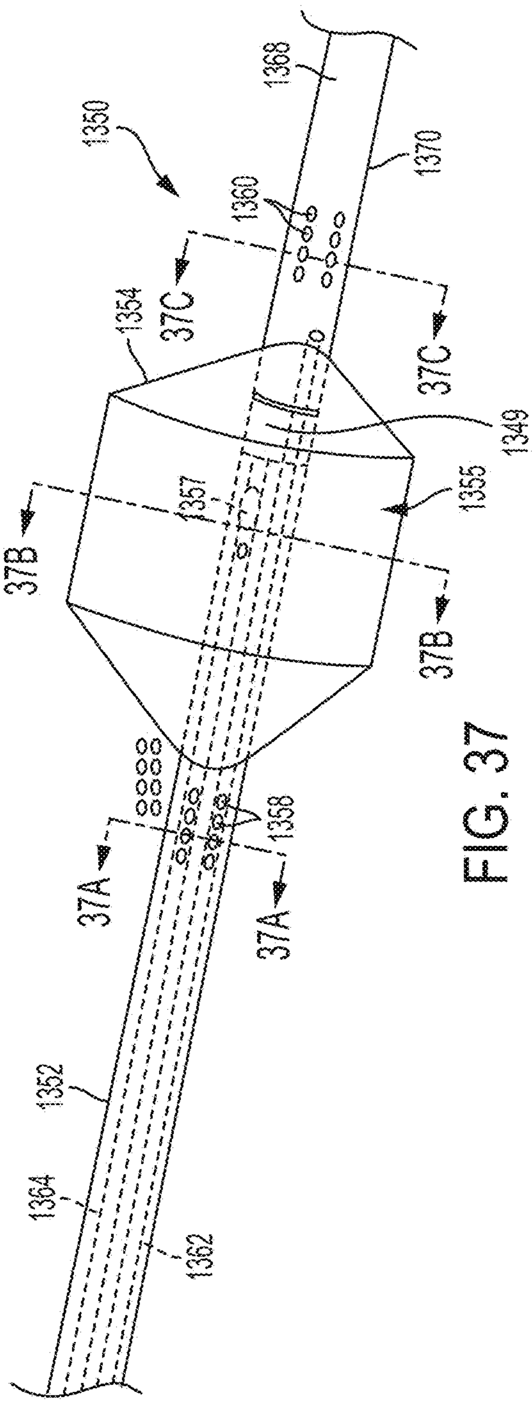
FIG. 37 is a top perspective view of an occlusion catheter system in accordance with a fifth preferred embodiment of the present invention.
Figure 37C:
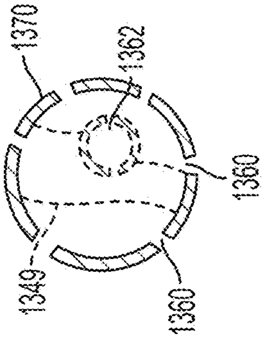
FIG. 37C is a cross-sectional view of the occlusion catheter system of FIG. 37, taken along line 37C-37C of FIG. 37.
Figure 37B:
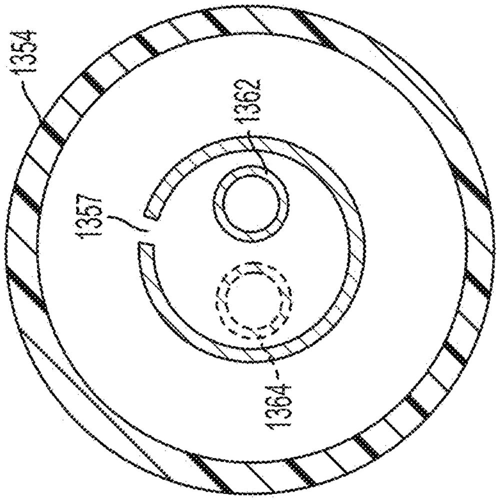
FIG. 37B is a cross-sectional view of the occlusion catheter system of FIG. 37, taken along line 37B-37B of FIG. 37.
Figure 37A:
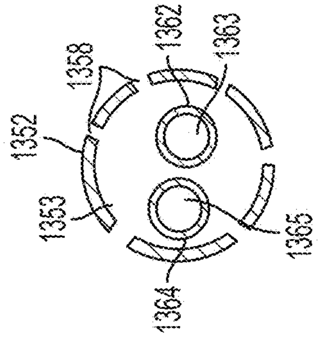
FIG. 37A is a cross-sectional view of the occlusion catheter system of FIG. 37, taken along line 37A-37A of FIG. 37.

Referring to FIGS. 36-37C, pharmacologically active agents, such as pressors, anticoagulants, anti-inflammatory agents, anti-hypertensive agents, anti-hypotensive agents, anti-arrhythmic agents, or any other indicated agent may be delivered using a fourth preferred embodiment of and occlusion catheter system 1300 or a pre-conditioning system 1300. Larger volume infusions are also deliverable using the pre-conditioning system or the fourth preferred embodiment of the occlusion catheter system 1300, including blood, blood products, extracorporeal membrane oxygenation adjuncts, hypothermia adjuncts, saline, contrast or other therapeutic or diagnostic agents.

A four preferred occlusion catheter system or pre-conditioning system 1300 generally comprises a balloon catheter that has a plurality of proximal side ports 1308 positioned proximal an occlusion member or balloon 1304 and a plurality of distal side ports 1310 positioned distally relative to the occlusion member or balloon 1304. The plurality of proximal side ports 1308 and the plurality of distal ports 1310 are operable independently of each other to deliver fluids from the forth preferred occlusion catheter system 1300 to the blood vessel into which the forth preferred system 130 is introduced. The pre-conditioning system 1300, synonymously termed "infusion system," includes a second catheter member 1302 that is connected to a proximal hub 1301 attached to a proximal end of the second catheter member 1302. The occlusion member 1304 is coupled toward a distal end of the second catheter member 1302. The occlusion member 1304, while depicted in FIG. 43 as a balloon, may be any type of member capable of vascular occlusion, such as those other embodiments of occlusion members disclosed herein or as are known in the art.

The second catheter member 1302 has a second lumen 1303 passing along a substantial longitudinal length of the second catheter member 1302. The second catheter member 1302 also has at least one, but preferably the plurality of proximal side ports 1308 passing through an outer wall of the second catheter member 1302. The plurality of proximal side ports 1308 is preferably in fluid flow communication with the second lumen 1303. The plurality proximal side ports 1308 may be in a regular or irregular pattern and may be positioned about the circumference of the second catheter member 1302 or may have only a single orientation relative to the central longitudinal axis 1331 of the infusion catheter system 1300.

A third catheter member 1320 of the fourth preferred occlusion catheter system 1300 extends distally relative to the occlusion member 1304 and terminates in an atraumatic tip 1306 or forms a proximal shaft or portion of the atraumatic tip 1306. The third catheter member 1320 has a third lumen 1322 passing along a substantial longitudinal length of the third catheter member 1302, preferably along and coaxially with the longitudinal axis 1331 near the distal end of the infusion catheter system 1300. The atraumatic tip 1306 is described above in greater detail with reference to the embodiments of the occlusion catheter 100, 300, 500, and serves to guide the catheter system 1300 as it traverses the vasculature and prevents the fourth preferred catheter system 1300 from tracking into collateral vessels, while preferably eliminating the need for a guide wire for placement of the occlusion catheter system 1300. The occlusion catheter system 1300 may also incorporate the atraumatic tip 450, 550 of the second the third preferred embodiments of the occlusion catheter system 300, 500, as is described herein.

At least one of and preferably all of the plurality of distal side ports 1310 pass through the outer wall of the third catheter member 1320 and communicate with the third lumen 1322 to communicate fluid distally relative to the occlusion member 1304. The plurality of distal side ports 1310 may be in a regular or irregular pattern and may be positioned about the circumference of the third catheter member 1320 or may have only a single orientation relative to the central longitudinal axis 1331 of the infusion catheter system 1300.

In the fourth preferred embodiment of occlusion catheter system 1300 where the occlusion member 1304 is a balloon, three lumens are preferred to service inflation of the occlusion member 1304 and fluid delivery to or sample collection from both of the plurality of proximal side ports 1308 and the plurality of distal side ports 1308. At least one hypotube or second catheter member 1312 is disposed within the second lumen 1303. Where the second catheter member or hypotube 1312 is employed, the second catheter member 1312 preferably has at least a first hypotube lumen 1314 and a second hypotube lumen 1316, with the first hypotube lumen 1314 configured to communicate an inflation fluid to the occlusion balloon 1304 and the second hypotube lumen 1316 configured to communicate fluid to the third catheter member 1320 and the plurality of distal side ports 1310 through the third lumen 1322, such that the third lumen 1322 is in fluid communication with the second hypotube lumen 1316. The second lumen 1303, between the second catheter member 1312 and the first catheter member 1302, preferably communicates fluid from the proximal hub 1301 to the plurality of proximal side ports 1308.

The at least one hypotube or second catheter member 1312 is preferably constructed of a material having different material properties than the first catheter member 1302 or the third catheter member 1320, such that the first lumen 1312 increases the column strength, pushability and pullability of the occlusion/infusion catheter system 1300 within the vasculature. In accordance with the fourth preferred embodiment of the occlusion catheter system 1300, the second catheter member 1312 is constructed of a relatively strong metal, preferably stainless steel or nitinol. The second catheter member 1312 may alternatively be constructed of a polymer, preferably a polymer having a higher hardness than that of either the first catheter member 1302 or the third catheter member 1320, but is not so limited. The first catheter member 1302, second catheter member 1312 and third catheter member 1320 may also be combined in construction and configuration to have a transitioning stiffness, to include a separate stiffening member, such as a nitinol wire or braided shaft, to have sufficient pushability to have the appropriate amount of column strength.

Referring to FIGS. 37-37C, a fifth preferred embodiment of the occlusion/infusion system 1350 is generally similar to the infusion system or occlusion catheter system 1300 of the fourth preferred embodiment. The occlusion/infusion system or occlusion catheter system 1350 of the fifth preferred embodiment employs a fist hypotube 1362 and a second hypotube 1364 within second lumen 1353 of a second catheter member 1352. The second hypotube 1364 extends from the proximal end of the second catheter member 1352 and terminates in communication with the occlusion balloon 1354. Inflation fluid is communicated through a second hypotube lumen 1365 of the second hypotube 1364, through an inflation port 1357 in the second catheter member 1352 that is positioned within a space 1355 defined within the balloon 1354 and fills the space 1355 to inflate the balloon 1354. A seal 1349 is positioned within the second catheter member 1352 distal to the inflation port 1357 to seal the second lumen 1353 distally of the seal 1349 and permit the inflation fluid to flow through the inflation port 1357 and into the balloon 1354, but not distally of a distal end of the balloon 1354 in the second lumen 1353. The first hypotube 1362 extends within the second lumen 1353 of the second catheter member 1352, extends beyond the seal 1349 and terminates within the third lumen 1368 in the distal portion of the second catheter member 1352 or a proximal portion of the atraumatic tip (not shown) to communicate with a plurality of distal side ports 1360. In this manner, fluid introduced into the fist hypotube 1362 is communicated through the first hypotube lumen 1363 to the plurality of distal side ports 1360 for release through the plurality of distal side ports 1360 distal to the occlusion balloon 1354.

It will be appreciated, therefore, that fluids may be infused through either the plurality of proximal side ports 1358 or the plurality of distal side ports 1360, independently, or through both, concurrently. The same or different infusion fluids may be infused through the plurality of proximal side ports 1358 and the plurality of distal side ports 1360, as well. The size, shape and position of the plurality of proximal side ports 1358 and that of the plurality of distal side ports 1360 may be configured to be the same or different and may be configured depending upon the type of fluid being infused. Furthermore, the plurality of proximal side ports 1358, the plurality of distal side ports 1360, the first hypotube 1362 and the second hypotube 1364 may be constructed of materials and tolerances suitable for powered injection at higher pressures and flow rates.

Alternatively, an adjunctive or secondary infusion catheter, such as those that are known in the art, that comprises a low-profile catheter shaft, a fluid connector at a proximal end of the catheter shaft and a plurality of fluid openings at a distal end of the catheter shaft, may be engaged to pass within the second lumen 1353, down the length of the second catheter member 1352 and out of a port distal to the occlusion member 1354. In this manner, the fourth and fifth preferred occlusion catheter systems 1300, 1350 may or may not have the plurality of proximal and distal side ports 1308, 1310, 1358, 1360, but may simply employ a secondary infusion catheter that is inserted into the second lumen 1303, 1353 of the second catheter member 1302, 1352, or, where the preferred occlusion catheter systems 1300, 1350 include the plurality of proximal and distal side ports 1308, 1310, 1358, 1360, the secondary infusion catheter may be inserted into a lumen, for instance the second hypotube lumen 1316, such that it will be able to extend a substantial longitudinal length of second catheter member 1302, 1352 and deliver fluid through the plurality of distal side ports 1310, 1360.

Finally, it will be understood by those in the art, that the terminus of the third lumens 1322, 1368 may be configured to laterally guide a guiding tip of a guide wire or catheter out of either the plurality of distal side ports 1310, 1360 or out of a dedicated skive (not shown) formed in the distal wall surface of third catheter member 1320, 1370.

An alternative configuration of the fourth and fifth preferred occlusion catheter systems 1300, 1350 may employ a secondary or adjunctive infusion catheter that is utilized for the primary occlusion, then as infusion is required, to endoluminally delivery the secondary infusion catheter laterally to the already placed occlusion catheter, diametrically collapse the occlusion member to permit luminal space for the infusion catheter to pass the occlusion member, then reestablish occlusion when the infusion catheter is positioned distal to the occlusion member, thereby forming occlusion around the infusion catheter.

In each of the foregoing described embodiments of the pre-conditioning systems or the fourth and fifth preferred embodiments of the occlusion catheter systems 1300, 1350 depicted and described with reference to FIGS. 35-36C, the systems 1300, 1350 may also include sensors, transmitters, receivers, interrogators or other means for measuring physical and/or physiological parameters distal and/or proximal one or more of the expandable occlusion members 1304, 1354, including, for example blood pressure sensors, heart rate sensors, flow sensors, chemical sensors, temperature sensors, oxygenation sensors, ischemia sensors, biological sensors, imaging sensors or the like.

Hemorrhage Exclusion and Flow Restoration Systems

The foregoing described embodiments of the vascular occlusion catheter system operate by creating a luminal obstruction to blood flow to the hemorrhage site to at least partially stem the outflow of blood and permit vascular repair of the hemorrhage site while preserving blood flow to the patient's brain and other vital organs. Alternative embodiments of the present invention operate to create an obstruction and occlude the hemorrhage site within the vascular wall. Moreover, rather than create luminal obstruction to blood flow, typically superior to the hemorrhage site, these alternative embodiments, restore patency of the blood vessel at the hemorrhage site and permit blood flow past the hemorrhage site while obstructing and occluding the trauma or injury to the vessel wall itself.

Figure 38:
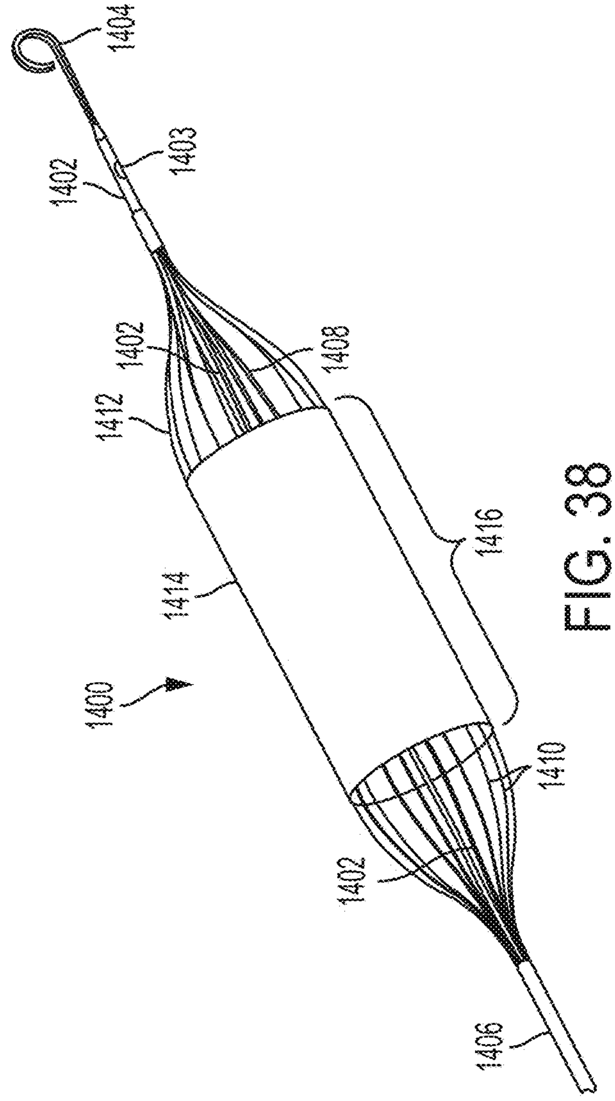
FIG. 38 is a top perspective view of a catheter system in accordance with a sixth preferred embodiment of the present invention, wherein the system is particularly adaptable for use as a hemorrhage exclusion system.

FIG. 38 illustrates a first preferred embodiment a hemorrhage exclusion system 1400 in accordance with the present invention. The preferred hemorrhage exclusion system 1400 is conceptually similar to occlusion/perfusion system 1270 depicted in FIG. 33. In the first preferred hemorrhage exclusion system 1400, an elongate support structure 1412 is formed of a plurality of structural support members and is connected to a longitudinally extending catheter or catheter sleeve 1406. The structural support members, which may be longitudinally oriented struts, form a distal cage section 1408 and a proximal cage section 1402. The distal cage section 1408 is preferably, immovably coupled to a distal end of the catheter 1406 and, when an atraumatic guiding tip 1404 is provided, proximal to the atraumatic guiding tip 1404. The proximal cage section 1410 is coupled to the catheter sleeve member 1406. An intermediate cage section 1416 extends between the proximal cage section 1410 and the distal cage section 1408. The hemorrhage exclusion system 1400 also includes an elongate support structure in the intermediate cage section 1416 that is preferably comprised of a continuation of the structural support members of the proximal and distal cage sections 1410, 1408 with a large open volume within the support structure. The open volume between the structural support members of the proximal cage section 1410 and distal cage section 1408 facilitates blood flow longitudinally through the elongate support structure along the outside of the catheter sleeve 1406. The elongate support structure may be constructed of any appropriate biocompatible material, including polymers, metals, composite materials or combinations thereof, as discussed above with reference to the occlusion members.

An exclusion member 1414 is carried on the intermediate cage section 1416 by the structural support members. The exclusion member 1414 extends along at least a substantial extent of the intermediate cage section 1416. The exclusion member 1414 may be fabricated of any appropriate woven or non-woven biocompatible material, including polymers, metals, composite materials or combinations thereof, as discussed above in reference to the occlusion members. The exclusion member 1414 may be plastically deformable, elastically deformable, or have shape memory or superelastic properties. The exclusion member 1414 is preferably, generally tubular and may be porous, non-porous or bioabsorbable. The exclusion member 1414 may be coupled to either the outer or inner surface of the elongate support structure 1412, or both. Coupling between the exclusion member 1414 may be in accordance with any methods and materials for joining biomaterials to support structures, including, without limitation, sutures, biocompatible adhesive, by reflow, by thermal welding, or by joining to another layer of exclusion member 1414 on the opposing surface of the support structure 1412 such that the struts of the support structure 1412 are at least partially encapsulated by the joined layers of the exclusion member 1414.

The catheter sleeve or catheter 1406 is preferably comprised of proximal and distal sections that are movably coupled to each other such that relative movement of the proximal and distal catheter sleeve members 1406 translates to diametric expansion or contraction of the elongate support structure 1412 and the exclusion member 1414. The proximal and distal portions of the catheter sleeve member 1406 are preferably comprised of a tubular structure with a lumen through which an opposing catheter passes. The catheter sleeve 1406 is not so limited and may be constructed of nearly any assembly or construction that permits collapse and expansion of the elongate support structure 1412, wherein the elongate support structure 1412 has a similar diameter to the catheter sleeve 1406 in the collapsed configuration and has an expanded (FIG. 38) diameter that allows blood flow through the intermediate cage section 1416 in the expanded configuration.

The elongate support structure 1412, may assume a wide variety of geometries, provided that the exclusion member 1414 supported on the elongate support structure defines a fluid flow pathway to restore patency to the vessel and allow blood to flow past the hemorrhage site.

In use, the hemorrhage exclusion system 1400 is advanced to a hemorrhage site. Contrast may be injected through the catheter 1406 and out of a port 1403 near the distal end of the catheter 1406 to image the hemorrhage, determine its position in the vessel wall and preferably estimate its relative size. The exclusion member 1414 is preferably positioned in such a manner as to span the hemorrhage site and extend both proximal and distal relative to the hemorrhage site. The support structure 1412 and the exclusion member 1414 are diametrically expanded into apposition with the vascular luminal wall surface, by relative movement of the proximal and distal portions of the catheter sleeve 1406. The exclusion member 1414 preferably blocks flow of blood out of the hemorrhage site and allows blood to continue to flow through the vessel and, preferably, preventing flow of blood out of the hemorrhage. Further imaging using injected contrast may be employed to verify successful positioning of the exclusion member 1414 and coverage of the hemorrhage site to stem the outflow of blood from the vessel trauma or injury. Alternatively or additionally blood pressure and/or blood flow data may be obtained by pressure and/or flow sensors operably associated with the hemorrhage exclusion system 1400, to also verify successful placement of the exclusion member 1414 and restoration of vascular patency and blood flow through the lumen of the exclusion member 1414, through the elongate support structure 1412 and through the vessel. The exclusion member 1414 is preferably maintained in place blocking the hemorrhage site at least until the medical practitioner is able to develop a plan to repair the hemorrhage.

An alternative preferred embodiment of the occlusion catheter system, which is similar to the foregoing hemorrhage exclusion system 1400 of the first preferred embodiment, involves eliminating the central catheter sleeve member 1406 and affixing the proximal cage section 1402 to a more proximal section of the catheter 1406. A constraining sheath (not shown) is then placed over the catheter 1406, the elongate structural support 1412 and the exclusion member 1414, constraining the structural support 1412 and exclusion member 1414 in a reduced diametric state until the constraining sheath is withdrawn. This configuration is particularly well suited where the elongate structural support 1412 is made of an elastic, shape memory or super elastic material. This alternate preferred embodiment is conceptually similar to the manner in which self-expanding or shape memory stents are endovascularly delivered and placed.

Figure 39:
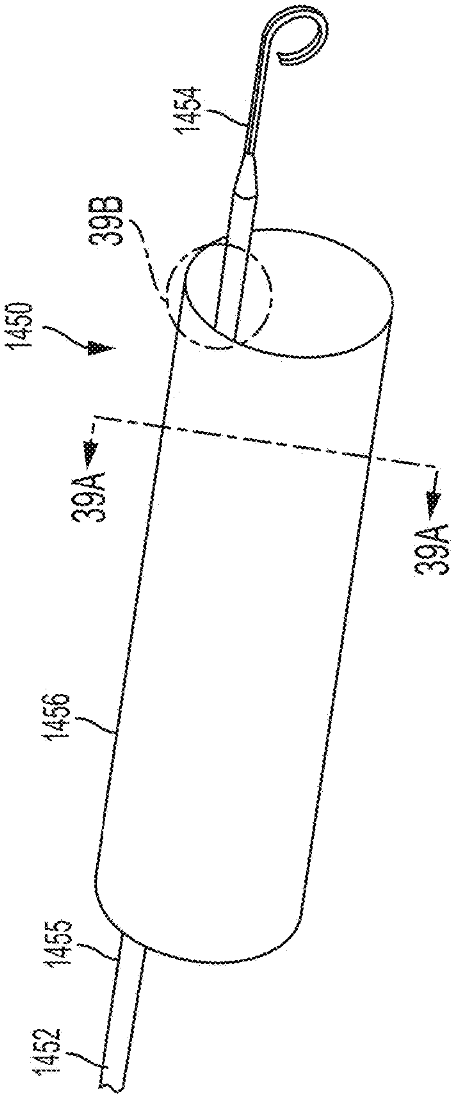
FIG. 39 is a top perspective view of a catheter system in accordance with a seventh preferred embodiment of the present invention, wherein the system is also particularly adaptable for use as a hemorrhage exclusion system.
Figure 39B:
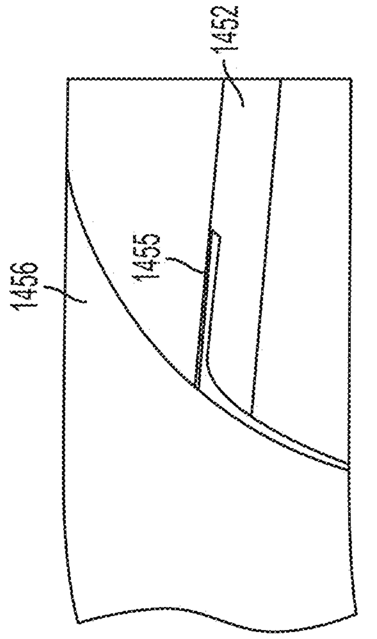
FIG. 39B is a magnified top perspective view of the catheter system of FIG. 38, taken from within shape 39B of FIG. 39.
Figure 39A:
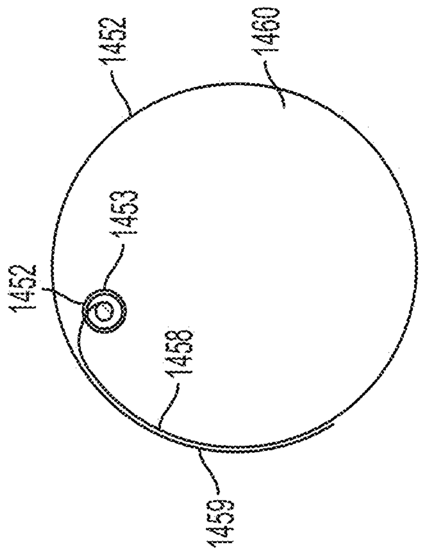
FIG. 39A is a cross-sectional view of the catheter system of FIG. 39, taken along line 39A-39A of FIG. 39.

Referring to FIGS. 39-39B, another or second preferred embodiment of the occlusion catheter system or hemorrhage exclusion system 1450 does not employ an elongate support structure 1414, as is utilized in the first preferred embodiment of the hemorrhage exclusion system 1400. The second preferred system 1450 includes a catheter 1452 having a relatively larger diametric profile which carries within a lumen in the catheter 1452 a furled or rolled sheet of an exclusion material 1456. An elongate spindle member 1453 carrying a rolled sheet of exclusion material 1456 is preferably positioned within a lumen of the catheter 1452. The catheter 1452 has an elongated slot 1455 passing through a wall surface of the catheter 1452. The exclusion material 1456 preferably has a leading edge that projects out of an elongate slot 1455 and, when the elongate spindle member 1453 is rotationally moved within the lumen of catheter 1452, the exclusion material 1456 unfurls or unrolls out of the elongated slot 1455. As the exclusion material 1456 fully unrolls from within the catheter lumen, the exclusion material 1456 preferably forms a diametrically enlarged generally tubular structure with at least one region of overlap of the exclusion material 1456, such that a first winding of the exclusion material 1456 forms an outer layer 1459 of the tubular structure and a second winding of the exclusion material 1456 forms an inner layer of the tubular structure. The tubular structure so formed defines a central lumen 1460 that allow blood flow through the tubular structure while the exclusion member 1456 is deployed in its diametrically expanded state.

In use, the hemorrhage exclusion system 1450 of the second preferred embodiment is endoluminally delivered to a hemorrhage site. Similar to the hemorrhage exclusion system 1400 of the first preferred embodiment, the hemorrhage site may be imaged by contrast injection to position the exclusion system 1450 relative to the hemorrhage site. Once properly positioned, the elongate spindle 1453 is rotatably actuated to unfurl or unroll the exclusion member 1456 through the elongate slot 1455 until it assumes its enlarged tubular shape and defines the blood flow central lumen 1460 and is preferably in apposition with the vascular wall surface and excludes or bypasses the hemorrhage site. Exclusion or bypass of the hemorrhage may be verified by contrast imaging or by blood pressure and/or blood flow data obtained from the patient or from blood pressure and/or blood flow sensors operably associated with, preferably attached to the exclusion system 1450.

In each of the foregoing preferred embodiments of the hemorrhage exclusion systems 1400, 1450 depicted and described with reference to FIGS. 38-39B, the systems 1400, 1450 may also include sensors, transmitters, receivers, interrogators or other means for measuring physical and/or physiological parameters distal and/or proximal one or more of the expandable occlusion members, including, for example blood pressure sensors, heart rate sensors, flow sensors, chemical sensors, temperature sensors, oxygenation sensors, ischemia sensors, biological sensors, imaging sensors or the like. The sensors may communicate with a controller, which may control various aspects of the operation of the systems 140, 1450, such as unfurling the exclusion member 1456 or collapsing the exclusion member 1456.

Inflation Control Systems

Figure 40:
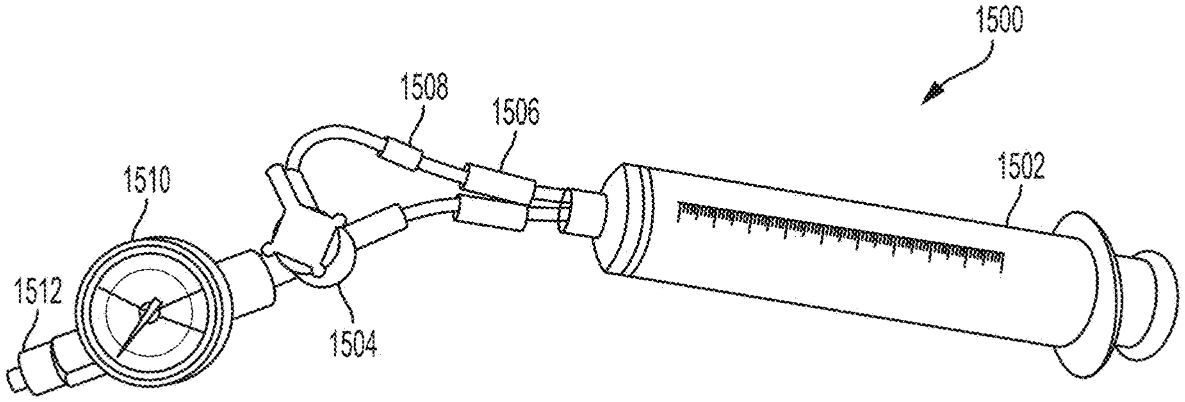
FIG. 40 is a top perspective view of a first preferred inflation control system that may be utilized with any of the occlusion catheter systems of the first, second and third preferred embodiments of the occlusion catheter system of FIGS. 1-18.

Referring to FIG. 40, a first preferred of an inflation control system 1500 may be utilized with any of the preferred occlusion catheter systems and other preferred systems having inflatable balloons or occlusion members described herein. In the first preferred embodiment, the inflation control system 1500 is preferably connected in-line between an inflation device (i.e. pressure source) and the balloon catheter, such as the first preferred occlusion catheter system 100. The inflation control system 1500 preferably helps to prevent the user from overinflating the balloon, such as the occlusion member 140 and damaging the blood vessel into which the occlusion member or balloon 140 is inserted. The inflation control system 1500 preferably includes a pressure source 1502, such as a syringe, which may be manually actuated or may be coupled to any of a large number of known automated injectors or pressure systems. The pressure source 1502 has a fluid source contained within the syringe, and is coupled to a bifurcated pressure conduit 1506, that in turn communicates with a free line and a regulated line. A one-way check valve 1508 is interposed in the regulated line to prevent both backpressure and backflow to the syringe 1502. A selectable flow valve 1504 is interposed in the free line and communicates with the regulated line. The selectable flow valve 1504 is operable to select the free line, the regulated line or both the free line and the regulated line. A fluid conduit leads from the selectable flow valve 1504 to a pressure sensor 1510. A coupling 1512, preferably a luer lock fitting, is provided to couple the occlusion catheter (not shown) to the pressure sensor 1510. While an analog pressure gauge is shown in FIG. 55, the analog pressure gauge is not limiting and a wide variety of analog or digital pressure sensors 1510 are capable of being used to provide the medical practitioner with information concerning the pressure in the inflation control system 1500.

In use, the inflation control system 1500 allows the practitioner to apply fluid pressure to the occlusion catheter, e.g., by advancing the syringe plunger, to inflate the occlusion balloon, while simultaneously preventing both backpressure and backflow. When the selector valve 1504 is positioned to open the regulated line and close the free line, fluid is free to flow through the check valve 1506 to the occlusion catheter and ultimately to the balloon. Pausing during inflation will not result in deflation of the balloon because when force is no longer applied to the syringe plunger, the fluid no longer advances through the check valve 1508 and the backpressure from the elastic balloon causes the fluid to try to exit the balloon/catheter, thereby causing the check valve 1508 to close.

The pressure sensor 1510 preferably senses the applied pressure at the pressure source 1502, but not necessarily at the occlusion balloon. Namely, because of the length of the occlusion catheter and the high resistance of the fluid passing through the narrow annular space of the catheter shaft, the pressure at the pressure gauge 1510 may be higher than the actual pressure in the balloon, but allowances and compensation may be calculated to predict or measure the pressure within the balloon with the gauge 1510. A dwell time typically exists between the time pressure is applied at the pressure source 1502 and when the pressure equilibrates at the occlusion balloon, but the pressure in the system between the check valve 1508 and the balloon quickly equalizes and the pressure sensor 1510 accurately reads the true pressure in the balloon. Excluding backpressure and backflow via the check valve 1508 creates a closed system in which the pressure can be allowed to equilibrate, as represented by a constant pressure readout on the pressure sensor 1510, which will then represent the pressure at the occlusion balloon. Additional fluid pressure may then be applied at the pressure source 1502.

As should be understood, the pressure sensor 1510 may have a "target occlusion pressure" identified thereon (i.e. such as a blue zone of the gauge 1510) that the practitioner knows to keep inflating until the needle comes a rest in the blue zone. This would indicate occlusion but not over inflation. Therefore, since this system is based on pressure and not volume, it is not necessary to know the vessel diameter before inflating the balloon. Rather, the practitioner need only fill the balloon until the needle of the pressure gauge 1510 comes to a rest in the "blue zone".

Pressure may be withdrawn from the occlusion balloon by means of the selector flow valve 1504 being switched to open the free line, by-passing the check valve 1508, and releasing pressure back to the pressure source 1502 from the occlusion balloon. The syringe plunger is preferably retracted and the fluid is drained from the balloon back into the syringe 1502.

Figure 41:
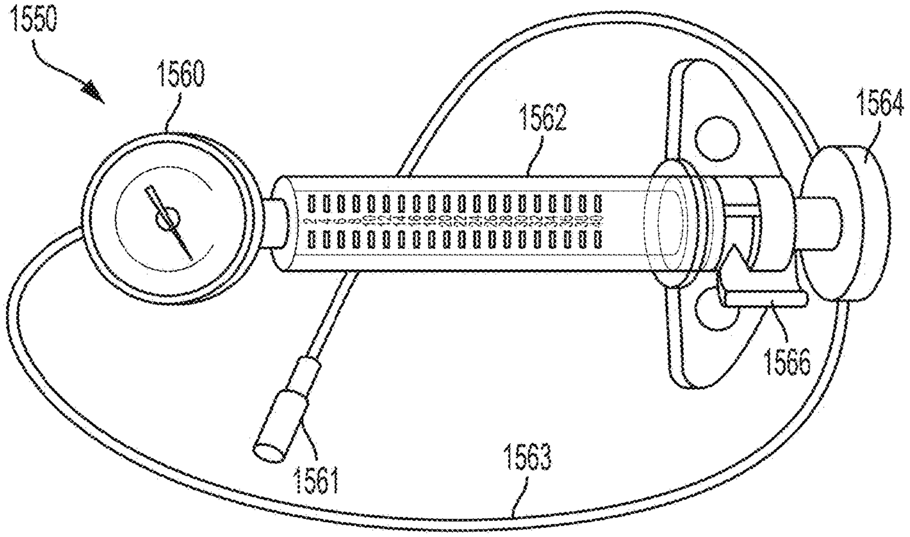
FIG. 41 is a top perspective view of a second preferred inflation control system that may be utilized with any of the occlusion catheter systems of the first, second and third preferred embodiments of the occlusion catheter system of FIGS. 1-18.

Referring to FIG. 41, a preferred second embodiment of an inflation control system 1550 is useful in the preferred inflation method of the present invention. A conventional balloon inflation device 1562 is illustrated in FIG. 41 (such as a QL Inflation Device, Atrion Medical, Arab, Alabama). The inflation device 1562 has a fluid chamber and a plunger 1564. The plunger 1564 is preferably threaded to allow for rotation of the plunger 1564 relative to the fluid chamber and controlled depression of the plunger 1564 within the fluid chamber. A fluid conduit 1563 communicates with an outlet 1561 in the inflation device 1562 to communicate the inflation fluid to the occlusion catheter (not shown), such as the occlusion catheter system 100 of the first preferred embodiment or any of the other preferred occlusion systems described herein, that is coupled to the inflation device 1550 via a coupling 1561. A pressure sensor 1560 is preferably provided in the outlet line of the inflation device 1550. A lock 1566 is preferably provided that engages the threaded plunger 1564 during pressurization and disengages from the threaded plunger 1564 during depressurization. The lock 1566 acts, essentially, to isolate the pressure within the occlusion balloon, catheter and fluid conduit 1563 and resists transmitting backpressure or fluid backflow to the plunger 1564. Essentially, the lock 1566 functions in a manner similar to the check valve 1508 in the preceding first preferred embodiment of the inflation control system 1500.

The method of inflating the occlusion balloon (not shown) using the inflation device 1562 entails the practitioner filling the fluid chamber with an inflation fluid by withdrawing the plunger 1564 to fill the fluid conduit 1563 and the fluid chamber. Expelling any air present in the fluid chamber and fluid conduit and connecting the inflation device 1550 to the occlusion catheter (not shown). To inflate the occlusion balloon, the plunger 1564 is actuated either by linear force or by rotating the plunger 1564 to engage the threads for a controlled pressurization. The lock 1566 should be engaged with the plunger 1564 to resist backpressure as the balloon occlusion member inflates. The pressure sensor 1560 will sense the applied pressure at the inflation device 1550, but not necessarily at the occlusion balloon. Because of the length of the occlusion catheter, a dwell time exists between the time pressure is applied at the inflation device 1550 and when the pressure equilibrates at the occlusion balloon. By excluding backpressure and backflow, the lock 1566 serves to creates a closed system in which the pressure can be allowed to equilibrate, as represented by a constant pressure readout on the pressure sensor 1560. When the pressure indicated on the pressure sensor 1560 is stable, this will then represent the pressure at the occlusion balloon. Additional fluid pressure may then be applied or pressure may be withdrawn from the occlusion balloon by either reversing the rotation of the plunger, essentially unthreading the plunger 1564, and depressurizing the balloon, or by means of releasing the lock 1566 and withdrawing the plunger 1564.

Figure 41A:
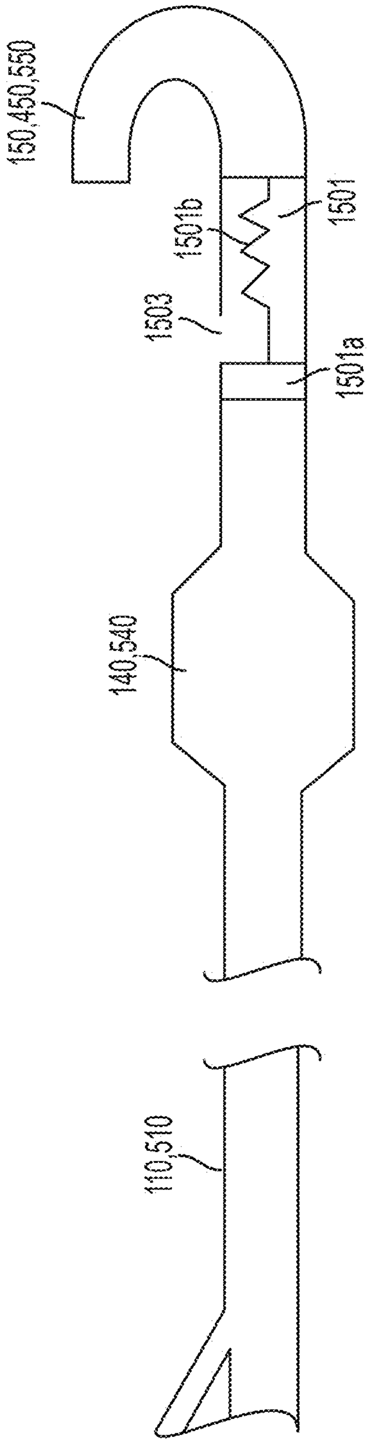
FIG. 41A is a cross-sectional view of a third preferred inflation control system that may be utilized with any of the occlusion catheter systems of the first, second and third preferred embodiments of the occlusion catheter system of FIGS. 1-18.

The second preferred inflation device 1550 is not limited to the specific arrangement described and shown herein and further mechanisms may be employed to prevent the user/practitioner from overinflating the balloon and damaging the blood vessel or the balloon. For example, as shown in FIG. 41A, any of the preferred vascular occlusion catheter systems, such as the first, second or third preferred occlusion catheter systems 100, 300, 500, may include a spring biased valve 1501 positioned within the catheter, proximal the atraumatic guiding tip 150, 450, 550, including a plunger 1501*a* sealingly engaging the catheter lumen and occluding a port 1503 located distally therefrom. The spring 1501*b* biases the piston 1501*a* into the position occluding the port 1503 and may define a spring constant configured to be overcome by a counteracting force corresponding to a pressure equal to or less than the cracking pressure of the vessel. Therefore, prior to overinflating the balloon and damaging the vessel, the pressure within the catheter overcomes the spring 1501*b* bias and pushes the plunger 1501*a* distally to expose the port 1503 and permit pressure release therethrough. The spring 1501*b* will push the plunger 1501*a* back into the position occluding port 1503 once sufficient pressure is released.

Infection/Contamination Control System

Rapid endovascular occlusion or exclusion of a traumatic hemorrhagic injury while on the battlefield or on the street involves not only a non-sterile environment, but an environment that is may be highly contaminated and prone to a wide variety of sources of bacterial or viral infections. It is desirable to design, construct and deploy a device that facilitates vascular access and endovascular delivery of a vascular occlusion catheter while minimizing infections resulting from contamination when used in austere environments, i.e., on the battlefield or on the street, rather than in a hospital or other sterile or controlled environment.

Figure 42A:
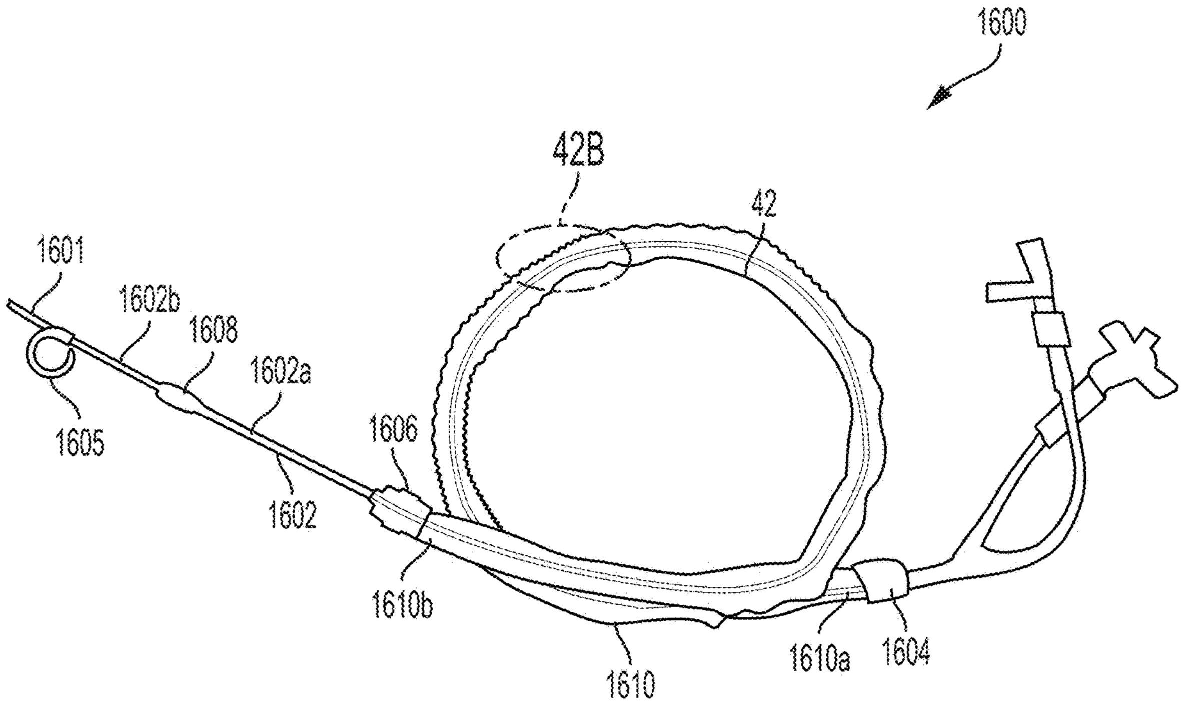
FIG. 42A is a side perspective view of a first preferred infection/contamination control system that may be utilized with any of the occlusion catheter systems of the first, second and third preferred embodiments of the occlusion catheter system of FIGS. 1-18.
Figure 42B:
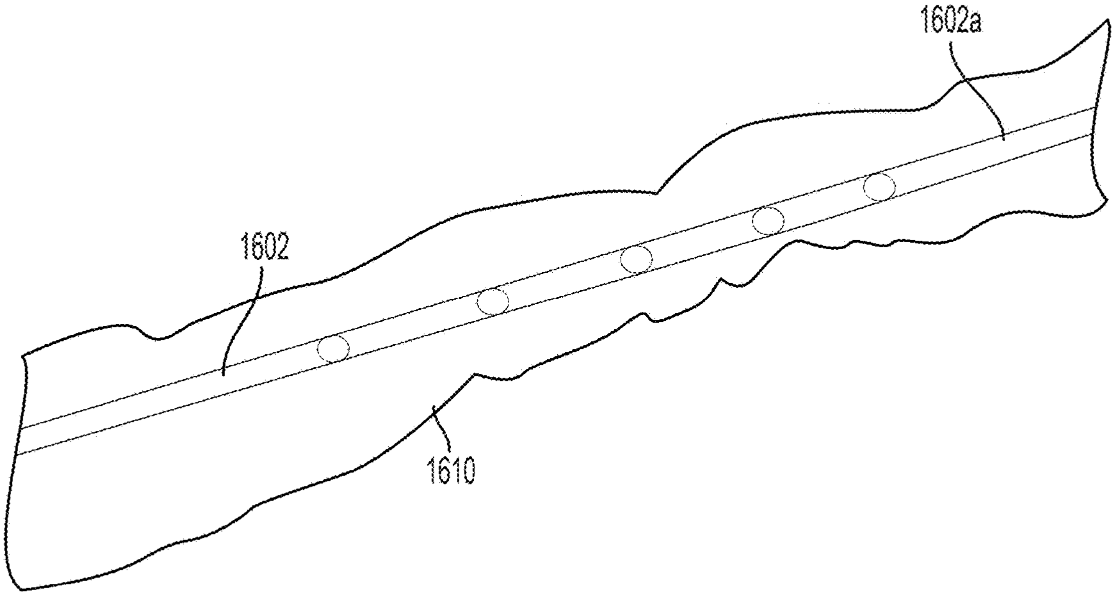
FIG. 42B is a magnified top perspective view of the infection/contamination control system of FIG. 42A, taken from within shape 42B of FIG. 42A.

Referring to FIGS. 42A and 42B, a first preferred infection control catheter sleeve system 1600 provides a substantially sterile field for the occlusion catheter 1602 and the occlusion balloon 1608 during access and endovascular delivery and through the vascular occlusion procedure. The occlusion catheter preferably includes an inflation catheter 1602*a* positioned proximate the balloon 1608 and a distal catheter member 1602*b* positioned distally relative to the balloon 1608. The inflation catheter member 1602*a* preferably has an inflation lumen similar to the inflation lumens described herein with respect to the preferred occlusion catheter members that has a port opening into an inner area of the occlusion balloon 1608 to permit inflation and deflation of the occlusion balloon 1608. The catheter sleeve system 1600 generally comprises a sleeve 1610 that is preferably comprised of an elongate tubular structure fabricated of a highly resilient material capable of being sterilized. The catheter sleeve 1610 is preferably a thin walled, elastic in inelastic polymer material that is capable of being longitudinally collapsed in an accordion-like fashion to ease insertion of the catheter 1602 into the sterile lumen of the elongate tubular structure 1610 and thereafter elongated in an accordion-like fashion as needed to cover substantially the entire shaft of the catheter 1602 in a covered configuration. The catheter sleeve 1610 preferably has hub members 1604, 1606 at respective proximal sleeve and distal sleeve ends 1610*a*, 1610*b* of the catheter sleeve tubular structure 1610 that permit the catheter 1602 to extend into and through the catheter sleeve 1600 while generally maintaining hemostasis and a sterile field within the catheter sleeve 1600. The preferred system 1600 includes proximal and distal hub members 1604, 1606 that may be constructed and configured as any type of hemostatic valve that permits the catheter 1602 to pass through the valve, such as, for example, without limitation, a Tuohy Borst valve.

The distal hub member 1606 may also include surfaces, such as flanges, wings, or other projections from the distal hub member 1606 that facilitate close approximation with the patient's skin and application of a shield dressing or other adhesive dressing to retain the distal hub member 1606, catheter sleeve 1600 and catheter 1602 positioned on the patient after the occlusion catheter has been delivered.

In use, as the distal tip of the catheter 1602 is inserted into an introducer sheath or the patient's body with the atraumatic tip 1605 substantially straightened along the longitudinal axis 1601 and the distal hub member 1606 of the catheter sleeve 1600 preferably remains mated to the introducer sheath during insertion of the catheter 1602. The preferred thin polymer of the catheter sleeve 1610 collapses in an accordion-like manner as the catheter 1602 is advanced into the body. Therefore, if something non-sterile comes into contact with the outside of the catheter sleeve 1610, it generally does not contaminate the catheter shaft 1602 that is inserted into the body. In addition, as the catheter 1602 is withdrawn from the patient, the sleeve 1610 is able to expand from its working configuration to the covered configuration such that materials, such as blood, from the vessel of the patient is substantially maintained within the sleeve 1610 or is swiped from the catheter 1602 by the distal hub 1606.

Guide Wire Compatibility

As indicated above, the vascular occlusion catheter systems, such as, for example, without limitation, the first, second and third preferred vascular occlusion catheter systems or occlusion catheter systems 100, 300, 500, are preferably capable of use without the need for a guide wire 1700. Guide wires 1700 are typically designed to navigate vessels to reach a desired vessel segment. Once the guide wire 1700 arrives at the destination in the vessel, the guide wire 1700 acts as a guide that facilitates delivery of the catheter system to the destination vessel segment. The atraumatic tip described above in detail with reference to the preferred embodiments of the occlusion catheter system 100, 300, 500, serves to guide the catheter as it traverses the vasculature and typically prevents the catheter from tracking into collateral vessels, while preferably eliminating the need for a guide wire for catheter placement.

Figure 43:
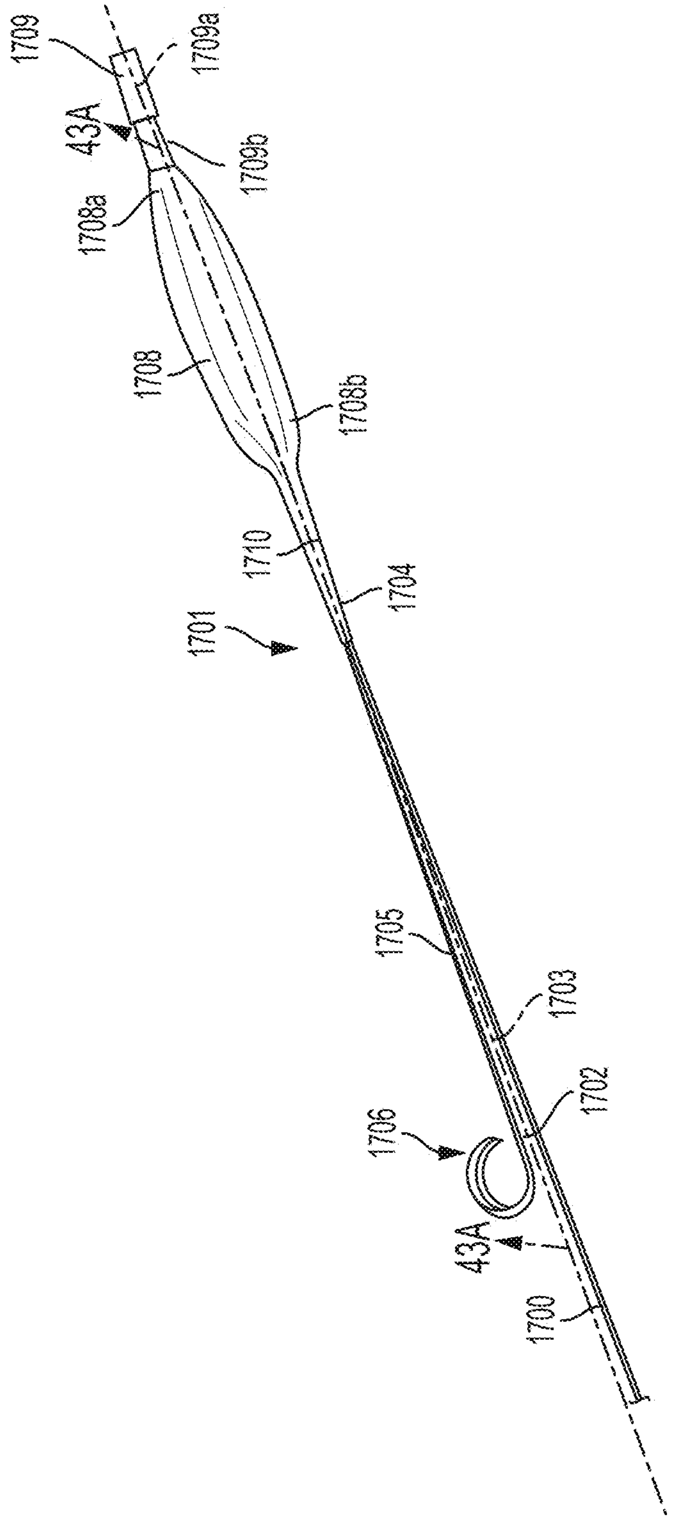
FIG. 43 is side perspective view of a catheter system in accordance with a eighth preferred embodiment of the present invention, wherein the system is adaptable for use with a guidewire.
Figure 43A:
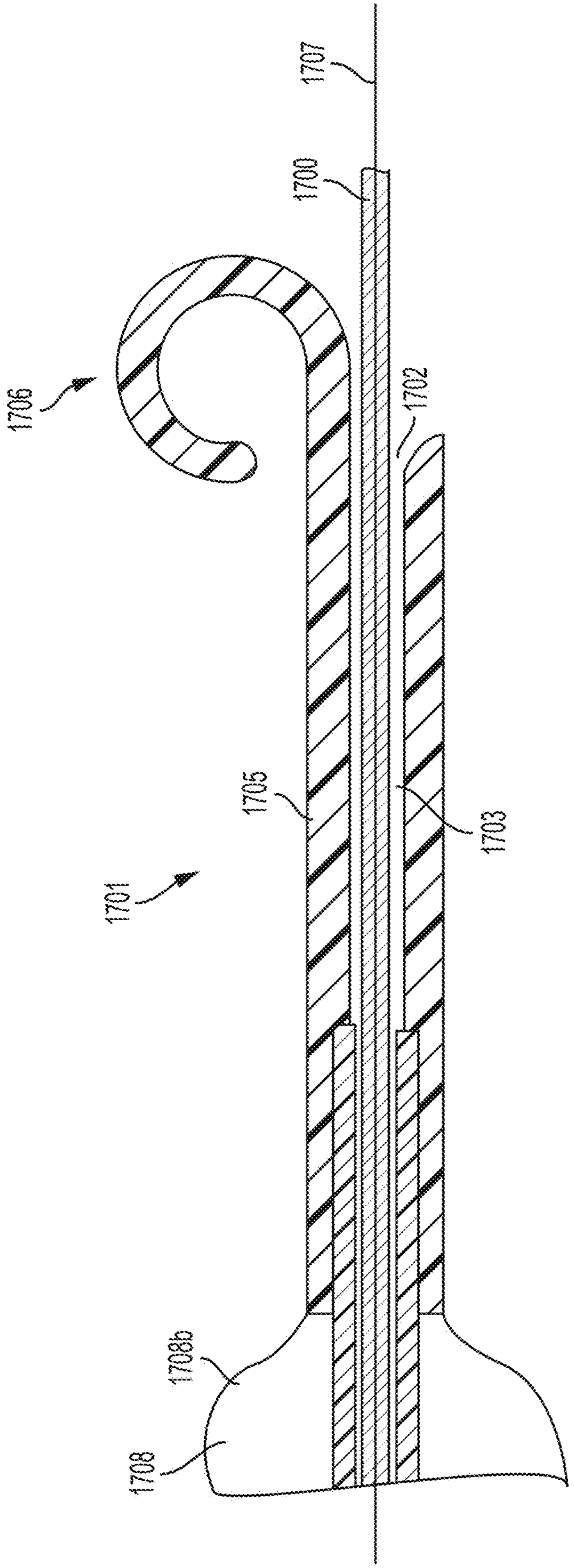
FIG. 43A is cross-sectional view of the catheter system of FIG. 43, taken along line 43A-43A of FIG. 43.

Practitioners, may desire for the preferred vascular occlusion catheter systems described herein to include guide wire capability for familiarity purposes. Accordingly, as shown in FIGS. 43 and 43A, an eighth preferred vascular occlusion catheter system 1701 is provided with guide wire capability, while not requiring the guide wire 1700 for use. In this preferred embodiment, the spiral or substantially circular shape of the atraumatic tip 1706, which is preferably configured in the same manner as the atraumatic tips 450, 550 of the second and third preferred embodiments, is positioned proximate an exit port 1702 of the catheter system 1701. The atraumatic tip 1706 may alternatively be removed and replaced with a distal end defining a substantially straight, compliant end and having the exit port 1702. The exit port 1702 is in communication with a guide lumen 1703 defined in a tip shaft 1705 of the atraumatic tip 1706. The guide lumen 1703 is preferably positioned coaxially or substantially parallel and proximate a longitudinal axis 1707 of the catheter system 1701. The catheter system 1701 preferably includes multiple lumens therein for inflation of an occlusion balloon 1708 and sliding receipt of the guide wire 1700.

In the preferred embodiment, the guide wire 1700 may be comprised of an eighteen thousandths of an inch (0.018") to an approximately twenty-five thousandths of an inch (0.025") or thirty-five thousandths (0.035") diameter guide wire 1700. The guide lumen 1703 and other lumens in the catheter system 1701 are designed and configured to accept sliding acceptance of the guide wire 1700. The guide wire 1700 may be slidably inserted and extend through the catheter system 1701, preferably coaxially or proximate and substantially parallel to the longitudinal axis 1707, and extend out of the distal end of the system 1701 through the exit port 1702. Accordingly, after the guide wire 1700 is inserted into a patient's body, the catheter system 1701 is capable of advancing over the guide wire 1700 to reach the desired vascular destination and the guide wire 1700 may subsequently be removed from the patient while retaining the system 1701, particularly the occlusion balloon 1708 therein.

The preferred catheter system 1701 includes a proximal hub (not show) that is the same or similar to the proximal hub of the herein described preferred embodiments. The proximal hub is connected to an inflation catheter member 1709 that is positioned at a proximal end of the occlusion member or occlusion balloon 1708. The inflation catheter member 1709 has an inflation lumen 1709*a* therein that opens into an internal space of the occlusion balloon 1708 at a first port 1709*b*. The inflation lumen 1790*a* and inflation catheter member 1709 are preferably position on or along the longitudinal axis 1707. The occlusion balloon 1708 preferably has a proximal end 1708*a* and a distal end 1708*b*, wherein the proximal end is connected to the inflation catheter member 1709. A distal catheter member 1705, which may be comprised of the tip shaft 1705 or may be a separate catheter member is positioned substantially on the longitudinal axis 1707 and is connected to the distal end 1708*b* of the balloon 1708.

The atraumatic tip 1706 is connected to or formed integrally with the distal catheter member or tip shaft 1705. The guide lumen 1703 is formed within the distal catheter member or tip shaft 1705 for slidable receipt of the guide wire 1700, preferably substantially along the longitudinal axis 1707.

In the preferred embodiment, the catheter system 1701 may maintain the generally spiral or substantially circular shaped atraumatic tip 1706 during insertion and the guide wire 1700 exits the catheter system 1701 through the exit port 1702 below the atraumatic tip 1706 such that the guide wire 1700 may be initially inserted into the patient and the system 1701 is guided into position along the guide wire 1700. The lumens of the preferred system 1701, including the guide lumen 1703 are in communication with the exit port 1702 and are appropriately dimensioned to accommodate the desired diameter guide wire 1700. In the preferred embodiment, the exit port 1702 is positioned on a lower side of the atraumatic tip 1706, opposite the circular profile, such that the circular profile is preferably oriented in its relaxed configuration after insertion into the patient's vessel and during the guiding movement into the appropriate location for the procedure in the vessel.

Figure 43B:
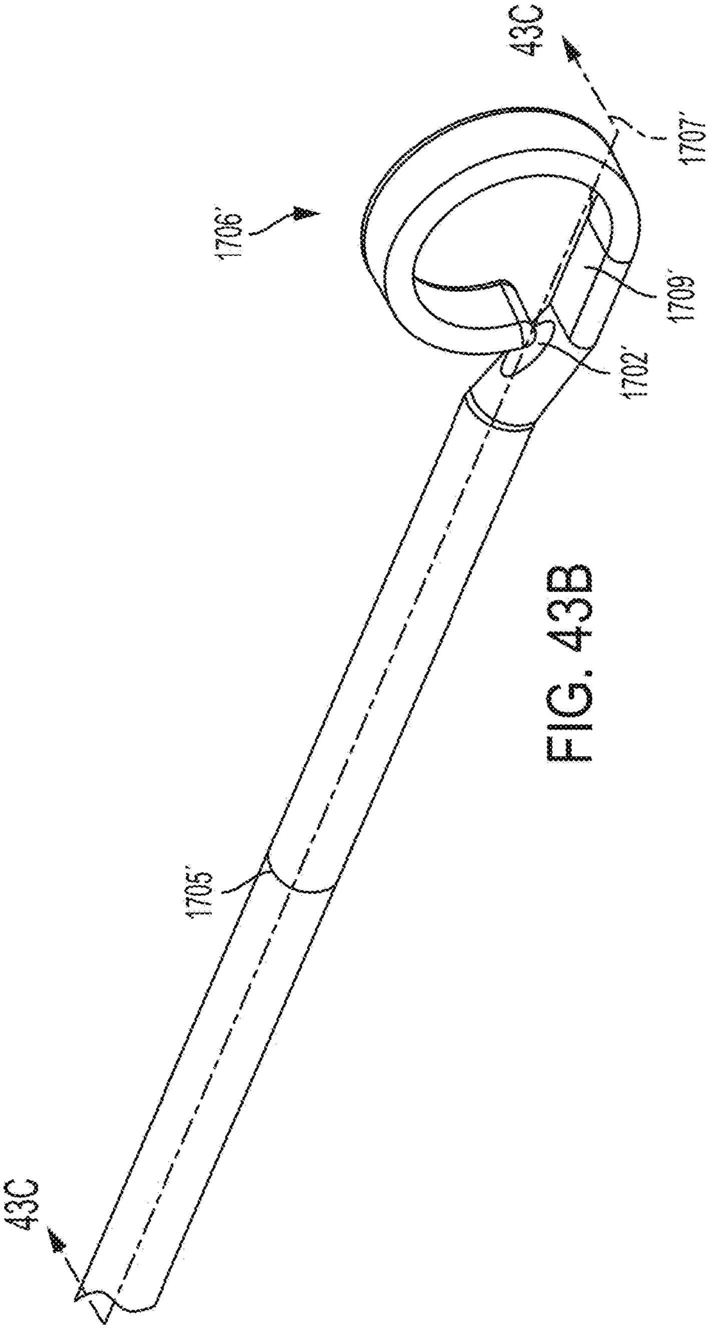
FIG. 43B is a side perspective view of an alternative preferred catheter system in accordance with the eighty preferred embodiment of the present invention.
Figure 43C:
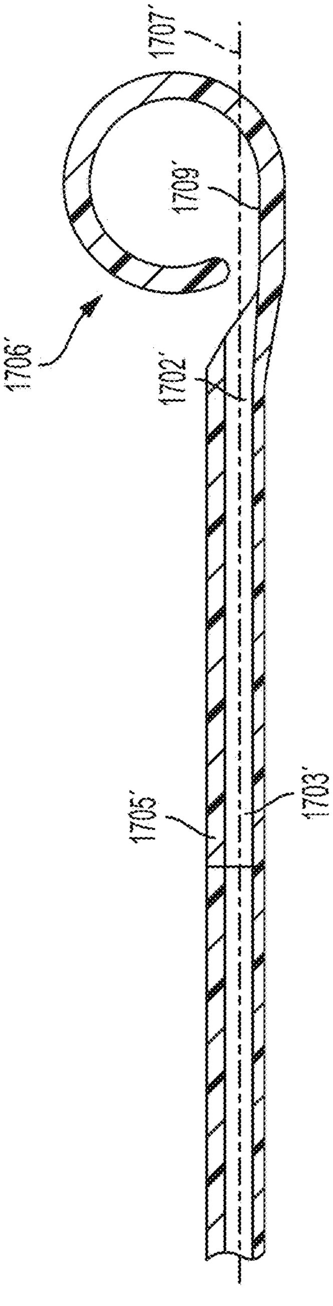
FIG. 43C is a cross-sectional view of the alternative preferred catheter system of FIG. 43B, taken along line 43C-43C of FIG. 43B.

The catheter system 1701 of the eighth preferred embodiment may also be configured such that the exit port 1702 is located on an opposite side of the atraumatic tip 1706 in the tip shaft 1705. Referring to FIGS. 43B and 43C, the alternative eighth preferred embodiment of the catheter system 1701' has similar features when compared to the preferred catheter system 1701 and like reference numerals are utilized to identify and describe like features with a prime symbol (') utilized to distinguish the eighth preferred embodiment from the alternative preferred embodiment. In the alternative preferred embodiment, the exit port 1702' is positioned proximate an inner tip surface 1709' of the atraumatic tip 1706' such that the guide wire 1700 would extend out of the alternative preferred system 1701' into the inner surface 1709' of the atraumatic tip 1706'. The guide wire 1700 is preferably sufficiently flexible to deflect out of the way of the atraumatic tip 1706' as it extends out of the exit port 1702' to guide the catheter system 1701' to the appropriate location in the vessel and position the occlusion member (not shown) in the appropriate zone, such as zone I, II or II, as is described above in the Summary of the Invention section. The alternative eighth preferred embodiment otherwise operates substantially the same as the eighth preferred embodiment of the system 1701 with the guide wire 1700.

Power Injection Capability

Injecting contrast media into a patient's vasculature enables increased visualization using fluoroscopy. Contrast delivery is most effective and efficient using a medical device called a "power injector" that can be programmed to deliver specific amounts of contrast agent at specific flow rates.

Figure 44:
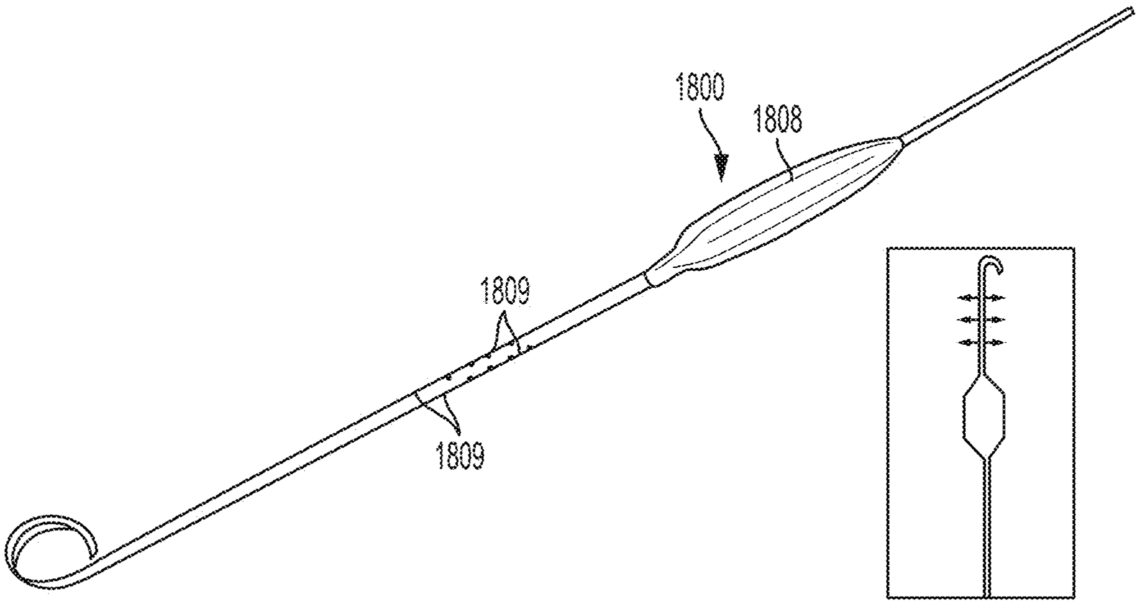
FIG. 44 is bottom perspective view of an occlusion catheter system in accordance with a ninth preferred embodiment of the present invention, wherein the system is adaptable for use as a power injection compatible vascular occlusion balloon catheter.

Referring to FIG. 44, in a ninth preferred embodiment, an occlusion catheter system 1800 includes multiple or a plurality of side ports 1809 to distribute contrast medium in the vasculature rapidly and evenly, preferably distally relative to an occlusion member 1808. At least one side port 1809 (multiple side ports in the illustrated embodiment) is in fluid communication with a lumen, e.g., the first, second and/or third lumen as described above with respect to the preferred catheter systems 100, 300, 500, 1300, 1350, accessible from the proximal hub (not shown), such as, for example, without limitation, the proximal hubs 190, 590, 790. Accordingly, contrast medium pumped into the catheter 1800 from the proximal hub is dispensed from the plurality of side ports 1809 and into the surrounding vasculature.

The catheter 1800 is preferably configured in a similar manner to the occlusion catheter system 100 with the first catheter member 130 having the first lumen 230, the second catheter member 110 having the second lumen 210 and the atraumatic tip 150 with a proximal portion comprised of the third catheter member 120 with the third lumen 220. The multiple side ports 1809 are preferably formed in the proximal portion of the atraumatic tip 150, the third catheter member 120 or the first catheter member 130 and may also be formed in each of these components of the catheter 1800. The plurality of side ports 1809 are in fluid communication with the first lumen 230 through the first catheter member 130, which is preferably in fluid communication with a power injection mechanism (not shown) through the first fluid pathway 192 in the proximal hub 190. The space within the occlusion member 1808 is preferably in fluid communication with an injection mechanism, such as the inflation control system 1500 through the second fluid pathway 194 and the second lumen 210, which introduces pressurized fluid or gas into the occlusion member 1808 through the distal port opening 160.

In the illustrated embodiment, the side ports 1809 are located distally from the occlusion member 1808. The side ports 1809, however, may be located proximally and/or distally of the occlusion member 1808 and the number of side ports 1809 may be determined according to the desired dispensing rate. The plurality of side ports 1809 may also be located in a single plane or in a circumferential manner around the catheter shaft. The plurality of side ports 1809 may also be utilized to withdraw fluids from the patient's vasculature, such as, for example, for blood sampling.

The lumen in fluid communication with the side ports 1809 may be a hypotube constructed of a metal (e.g., nitinol), a polymer, a reinforced polymer (e.g., braided), or a composite material in order to withstand power injection pressures. The catheter hub, extension lines, and connectors are also constructed of the appropriate polymer/composite material in order to withstand power injection pressures. For example, extension lines may be braid reinforced or otherwise reinforced to withstand the power injection pressures. The catheter 1800 is, therefore, capable of being used safely with a power injector for contrast injections. The catheter 1800 may also be used for visualization of hemorrhage using fluoroscopy by injecting visualization agent into the patient and visualizing flow and, particularly hemorrhage.

Infusion Catheter

Figure 45:
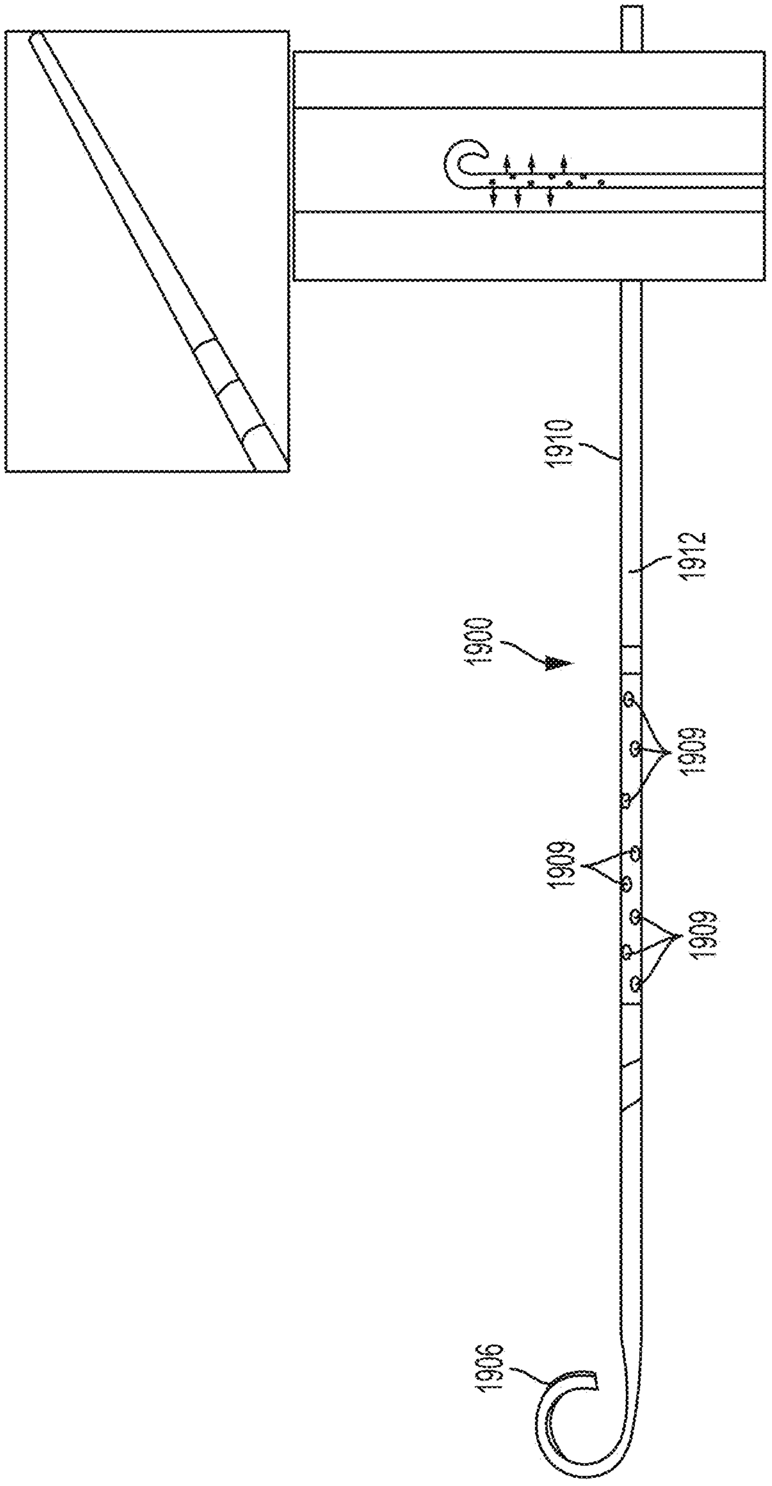
FIG. 45 is side elevational view of an occlusion catheter system in accordance with a tenth preferred embodiment of the present invention, wherein the system is also adaptable for use as an infusion catheter.

Referring to FIG. 45, an infusion catheter or occlusion catheter system 1900 in accordance with a tenth preferred embodiment (not including an occlusion member) can be utilized to infuse and withdraw fluids from a patient's vascular system. Similarly to the occlusion catheter 100, 300, 500, the infusion catheter 1900 includes a distal, curled/spiral, polymeric atraumatic tip 1906 to assist the catheter 1900 to track up a blood vessel and remain in the central lumen of the vasculature. The catheter shaft 1910 is configured to have an appropriate stiffness to be pushable without kinking, while also being sufficiently flexible to not damage blood vessels. The catheter shaft 1910 may be constructed of a polymeric material, a metallic material, or a combination of plastic, metal, and composite materials (e.g., fiberglass, carbon fiber, nylon, etc.) to achieve the appropriate stiffness. The catheter shaft 1910 may be approximately five French (5 Fr) or five and twenty-four hundredths millimeters (5.24 mm), but may alternatively be constructed in other sizes as necessary. Similarly, the diameter of the generally circular profile of the atraumatic tip 1906 (discussed below) may also be sized appropriately according to the destination vessel size. The atraumatic tip 1906 is preferably designed and configured similar to the atraumatic tips 450, 550 of the second and third preferred embodiments of the occlusion catheter system 300, 500, as is described above.

Similarly to the occlusion catheter systems 100, 300, 500 of the first, second and third preferred embodiments, the infusion catheter 1900 of the tenth preferred embodiments is intended to be used without a guide wire for rapid insertion. The combination of the atraumatic tip 1906 and catheter shaft 1910 substantially negates the need for a separate guide wire, as is typically utilized in procedures introducing catheters, stents, screws or other devices into the patient. The infusion catheter 1900 preferably has a single lumen 1912 connected to a hub (not shown), e.g., with a standard luer lock fitting (not shown) at the proximal end of the occlusion catheter system 1900. The occlusion catheter system 1900 may alternatively be connected with a hub via any of numerous different connectors/fittings, that are currently known or that later become known.

The catheter shaft 1910 of the tenth preferred embodiment includes a plurality of side ports 1909 (a plurality of ports 1909 in the illustrated embodiment) proximal relative to the atraumatic tip 1906. The plurality of side ports 1909 is in fluid communication with the lumen 1912. A fluid may be injected at the catheter hub and exit into the vasculature at the plurality of side ports 1909. The plurality of side ports 1909 preferably assist in distributing the fluid evenly to prevent the fluid stream from causing damage to the blood vessel. The plurality of side ports 1909 maybe be positioned in a single plane or spiral around the catheter shaft 1910 or may otherwise be arranged and configured to facilitate injection in a manner desired by the medical professional or designer.

As explained above, the catheter shaft 1910 is preferably constructed of a material capable of withstanding the pressures and flow rates of power injection for contrast visualization. The catheter shaft 1910 could be braided or non-braided. The catheter 1900 may also be used for blood pressure monitoring via an external pressure sensor or to withdraw fluids (i.e. blood sampling, blood filtration/oxygenation (extracorporeal membrane oxygenation ("ECMO"), etc.).

The infusion catheter 1900 may be used in combination with an occlusion catheter system, but is not so limited. For example, an occlusion catheter system could be placed in the right femoral artery and advanced to the aorta and the occlusion member inflated to occlude the vessel. The infusion catheter 1900 could be inserted via the left femoral artery and used to infuse fluids (i.e. blood products, hyper-oxygenated perfusate, crystalloids, etc.). The infusion catheter 1900 could also be used with a power/hand injector to inject radiopaque contrast (CO2, Isovue, etc.) to visualize the hemorrhage.

The infusion catheter 1900 may be packaged with a pre-installed "peel-away sheath" that is used to straighten the atraumatic tip 1906 for insertion into the valve of the introducer sheath or directly into the blood vessel. The peel-away sheath is advanced distally to capture and straighten the atraumatic tip 1906 and then can be retracted proximally toward the catheter hub and peeled off the catheter shaft 1910 if necessary.

Decision Support Systems

Intelligent systems are becoming widely accepted and are finding their way into acceptance in medical diagnostics and in the performance and predictive analysis of medical device clinical trials. Articles and presentations have been given related to this subject matter.

An approach based on Bayesian statistics is an approach for learning from evidence as it accumulates. In clinical trials, traditional statistical methods may use information from previous studies only at the design stage. Then, at the data analysis stage, the information from these studies is considered as a complement to, but not part of, the formal analysis. In contrast, the Bayesian approach uses Bayes' Theorem to formally combine prior information with current information on a quantity of interest. The Bayesian idea is to consider the prior information and the trial results as part of a continual data stream, in which inferences are being updated each time new data become available.

The Bayes theorem may be used to calculate the probability of coronary artery disease based upon clinical data and non-invasive test results. Pre-test probabilities of disease are assigned based on clinical data and the equation is used to calculate post-test probabilities after multiple sequential tests. When good prior information on clinical use of a device exists, the Bayesian approach enables this information to be incorporated into the statistical analysis of a given decisional matrix.

Good prior information is often available for medical devices because of their mechanism of action and evolutionary development. The mechanism of action of medical devices is typically physical. As a result, device effects are typically local, not systemic. Local effects can sometimes be predictable from prior information on the previous generations of a device when modifications to the device are minor. Good prior information can also be available from studies of the device overseas.

Bayesian methods are usually less controversial when the prior information is based on empirical evidence such as data from clinical trials. Bayesian methods can, however, be controversial when the prior information is based mainly on personal opinion.

Bayesian analyses are often computationally intense. Recent breakthroughs in computational algorithms and computing speed have, however, made it possible to carry out calculations for very complex and realistic Bayesian models. These advances have resulted in an increase in the popularity of Bayesian methods. A basic computational tool is a method called Markov Chain Monte Carlo ("MCMC") sampling, which is a method for simulating from the distributions of random quantities.

As the Bayesian predictive modeling scheme has become well known, it is useful in conjunction with the various control systems of the present invention, as described above, as predictive analysis profiling during a vascular occlusion procedure.

In connection with the present invention, the various preferred embodiments of the occlusion catheter systems and related components and devices described herein, and the occlusion or the occlusion/perfusion control over the vascular occlusion devices, is well suited to oversight and control using intelligent systems, such as those in which Bayesian probability analysis is applied. In each of the above-described embodiments, including without limitation, the vascular occlusion devices, the occlusion catheter systems, the control systems for controlling apposition of the occlusion member against the vessel wall or for excluding the hemorrhage site, the pre-conditioning systems or the occlusion/perfusion systems, both physical and/or physiological data is either acquired or is capable of being acquired. Acquisition of real-time physical and/or physiological data during an occlusion procedure or during a vascular repair involving a vascular occlusion includes, without limitation, blood pressure, heart rate, flow, chemistry, temperature, oxygenation, imaging or the like. In combination with prior data obtained from clinical practice guides, standard of care protocols, process flowcharts, and other data acquired during prior procedures, intelligent predictive analysis may be applied in software or firmware resident at the computer controllers, e.g., controllers 750, 753, 803, to either automatically control the preferred systems described herein or to output intelligently processed information to the medical practitioner to aid in decision making during the occlusion procedure.

It will be appreciated by those skilled in the art that changes could be made to the embodiments described above without departing from the broad inventive concept thereof. For example, nearly any of the individual components of the various embodiments may be incorporated with other preferred embodiments without departing from the spirit and scope of the preferred inventions. The plurality of proximal and distal side ports may be incorporated in nearly any of the preferred occlusion catheter systems, the atraumatic tips may be mixed and matched with the various embodiments of the occlusion catheter systems, nearly any of the preferred occlusion members, such as the first preferred occlusion balloon system 1200 with the projecting members 1204 may be incorporated with any of the preferred occlusion catheter systems and other similar arrangement of the disclosed features of the preferred systems may be employed without departing from the spirit and scope of the disclosed preferred inventions. It is understood, therefore, that the invention is not limited to the particular embodiments disclosed, but it is intended to cover modifications within the spirit and scope of the present invention, as defined by the appended claims.

We claim:

1. An occlusion catheter system for partial or complete occlusion of the aorta, the occlusion catheter system comprising:

- a proximal hub forming an internal inflation fluid pathway;
- a manually actuated flow valve proximal to an inlet of the proximal hub, whereby an outlet of the flow valve is connected to the inlet of the proximal hub, the flow valve being selectively actuatable into a first position configured to provide bi-directional fluid communication between an inflation device and the inflation fluid pathway of the proximal hub;
- a proximal catheter member extending from the proximal hub;
- a distal catheter member;
- an intervening, compliant occlusion balloon configured to be inflated by a liquid inflation medium when disposed within the aorta, the occlusion balloon being connected to the proximal catheter member and the distal catheter member, the occlusion balloon having a proximal neck, a distal neck and an intervening body portion; and
- a stiffener member having a proximal end and a distal end, the proximal end located within and fixedly coupled to the proximal hub, the stiffener member extending otherwise uncoupled within the proximal catheter member, and the stiffener member further extending into and beyond the body portion of the occlusion balloon.

2. The occlusion catheter system of claim 1, further comprising a lumen originating from the proximal hub, in fluid communication with the inflation fluid pathway, and extending through the proximal catheter member and into communication with the occlusion balloon, and wherein the stiffener member is longitudinally solid throughout an extension thereof within the proximal catheter member, into and beyond the body portion of the occlusion balloon.

3. The occlusion catheter system of claim 1, wherein the stiffener member defines an internal lumen.

4. The occlusion catheter system of claim 1, wherein the proximal end of the stiffener member is bonded to the proximal hub.

5. The occlusion catheter system of claim 4, wherein the proximal end of the stiffener member is adhesively bonded to the proximal hub.

6. The occlusion catheter system of claim 1, wherein the distal end of the stiffener member is fixedly coupled to a proximal section of the distal catheter member.

7. The occlusion catheter system of claim 1, wherein the flow valve is selectively actuatable between the first position and a second position in which fluid communication between the inflation device and the inflation fluid pathway is blocked, with the stiffener member extending within the proximal catheter member.

8. The occlusion catheter system of claim 1, wherein the proximal catheter member, the occlusion balloon and the distal catheter member have a greatest outer diameter of 8 Fr or less in an uninflated configuration.

9. The occlusion catheter system of claim 1, wherein the proximal catheter member, the occlusion balloon and the distal catheter member have a greatest outer diameter of 7 Fr or less in an uninflated configuration.

10. The occlusion catheter system of claim 1, wherein the proximal catheter member, the occlusion balloon and the distal catheter member have a greatest outer diameter of 6 Fr or less in an uninflated configuration.

11. The occlusion catheter system of claim 1, wherein the stiffener member is constructed of a metal.

12. An occlusion catheter assembly comprising:

the occlusion catheter system of claim 1; and the inflation device being configured to fluidly connect with the inflation fluid pathway of the proximal hub via fluid flow through the flow valve located therebetween, and to deliver the liquid inflation medium through the flow valve to inflate the occlusion balloon, when the occlusion balloon is disposed within the aorta, to at least partially occlude the aorta.

13. The occlusion catheter assembly of claim 12, wherein the inflation device is a manually actuated syringe.

14. An occlusion catheter system for partial or complete occlusion of the aorta to preserve blood flow to a heart and brain of a patient, the occlusion catheter system comprising:

a proximal hub having a single inlet and forming an internal inflation fluid pathway;

a manually actuated flow valve;

a proximal catheter member in fluid communication with the inflation fluid pathway;

a distal catheter member;

an intervening, compliant occlusion balloon configured to be inflated by a liquid inflation medium when disposed within the aorta, the occlusion balloon connecting the proximal catheter member with the distal catheter member;

a lumen extending from the proximal hub through the proximal catheter member and into communication with the occlusion balloon; and a stiffener member having a proximal end and a distal end, the proximal end of the stiffener member (i) being located within and bonded to the proximal hub with the stiffener member extending otherwise uncoupled within the lumen, and (ii) being spaced distally from the flow valve, the distal end of the stiffener member extending into the distal catheter member, wherein, in a first position of the flow valve, the flow valve is configured to provide bi-directional fluid communication between an inflation device and the inflation fluid pathway, via the single inlet, for occlusion balloon inflation and deflation, and in a second position of the flow valve, fluid communication between the inflation device and the inflation fluid pathway is blocked, the flow valve being selectively actuatable into each of the first and second positions with the stiffener member extending distally from the proximal catheter member.

15. The occlusion catheter system of claim 14, wherein the proximal end of the stiffener member is adhesively bonded to the proximal hub.

16. The occlusion catheter system of claim 14, wherein the distal end of the stiffener member is fixedly coupled to a lumen of the distal catheter member.

17. The occlusion catheter system of claim 14, wherein the stiffener member is longitudinally solid from the proximal end to the distal end thereof.

18. The occlusion catheter system of claim 14, wherein the stiffener member defines an internal lumen therein.

19. The occlusion catheter system of claim 14, wherein the proximal catheter member is tubular, the distal catheter member is tubular, and the proximal catheter member, the occlusion balloon and the distal catheter member have a greatest outer diameter of 8 Fr or less in an uninflated configuration.

20. The occlusion catheter system of claim 14, wherein the proximal catheter member is tubular, the distal catheter member is tubular, and the proximal catheter member, the occlusion balloon and the distal catheter member have a greatest outer diameter of 6 Fr or less in an uninflated configuration.

21. The occlusion catheter system of claim 14, wherein the proximal catheter member and the distal catheter member are constructed of a polymeric material, the occlusion balloon having a proximal balloon end and a distal balloon end, the proximal balloon end attached to the proximal catheter member and the distal balloon end attached to the distal catheter member.

22. An occlusion catheter assembly comprising:

the occlusion catheter system of claim 14; and the inflation device being configured to fluidly connect with the inflation fluid pathway of the proximal hub via fluid flow through the flow valve located therebetween, and to deliver the liquid inflation medium through the flow valve to inflate the occlusion balloon, when the occlusion balloon is disposed within the aorta, to at least partially occlude the aorta.

23. The occlusion catheter assembly of claim 22, wherein the bonding of the proximal end of the stiffener member with the proximal hub provides stiffness for the occlusion catheter system to resist pressure that builds against the occlusion catheter system during occlusion of the aorta.

24. The occlusion catheter assembly of claim 22, wherein the inflation device is a manually actuated syringe.

25. An occlusion catheter system for partial or complete occlusion of the aorta to occlude non-compressible hemorrhage in emergency or trauma environments where guidance imaging is typically not available, the occlusion catheter system comprising:

a proximal hub forming an internal inflation fluid pathway;

a manually actuated flow valve having an inlet and an outlet, whereby the outlet of the flow valve is connected to an inlet of the proximal hub, the flow valve being selectively actuatable into a first position configured to provide bi-directional fluid communication between a syringe and the inflation fluid pathway of the proximal hub;

a proximal catheter member extending from the proximal hub;

a distal catheter member terminating in an atraumatic tip;

an intervening, compliant occlusion balloon configured to be inflated by a liquid inflation medium when disposed within the aorta, the occlusion balloon connecting the proximal catheter member with the distal catheter member;

a length marking on an exterior of the proximal catheter member to indicate an insertion depth of the occlusion catheter system;

an inflation lumen originating from the proximal hub, in fluid communication with the inflation fluid pathway, and extending through the proximal catheter member and into fluid communication with the occlusion balloon; and a stiffener member having a proximal end and a distal end, the stiffener member being longitudinally solid from the proximal end to the distal end, the stiffener member extending within the inflation lumen, the occlusion balloon and into the distal catheter member, the proximal end of the stiffener member being located within and fixedly coupled to the proximal hub with the stiffener member extending otherwise uncoupled within the inflation lumen, and the distal end of the stiffener member extending into the distal catheter member, wherein the proximal catheter member, the occlusion balloon and the distal catheter member have a greatest outer diameter of 6 Fr or less in an uninflated configuration.

* * * * *